United States Patent

Bohlmann et al.

Patent Number: 5,986,115
Date of Patent: Nov. 16, 1999

[54] 7α-(ξ-AMINOALKYL)-ESTRATRIENES, PROCESS FOR THEIR PRODUCTION, PHARMACEUTICAL PREPARATIONS WHICH CONTAIN THESE 7α-(ξ-AMINOALKYL)-ESTRATRIENES AS WELL AS THEIR USE FOR THE PRODUCTION OF PHARMACEUTICAL AGENTS

[75] Inventors: Rolf Bohlmann; Dieter Bittler; Josef Heindl; Nikolaus Heinrich; Helmut Hofmeister; Hermann Künzer; Gerhard Sauer; Christa Hegele-Hartung; Rosemarie Lichtner; Yukishige Nishino; Karsten Parczyk; Martin Schneider, all of Berlin, Germany

[73] Assignee: Schering AG, Germany

[21] Appl. No.: 09/239,490

[22] Filed: Jan. 28, 1999

Related U.S. Application Data

[62] Division of application No. 08/915,171, Aug. 20, 1997, Pat. No. 5,866,560
[60] Provisional application No. 60/029,948, Nov. 8, 1996.

[30] Foreign Application Priority Data

Aug. 20, 1996 [DE] Germany ............... 196 35 525

[51] Int. Cl.⁶ ............... C07D 315/00; C07J 31/00; C07J 13/00; C07J 53/00; C07J 1/00
[52] U.S. Cl. ............... 549/416; 552/528; 552/529; 552/536; 552/538; 552/510; 552/623; 552/625; 552/626; 552/629; 552/630; 552/642; 552/646; 552/647; 552/648; 552/650
[58] Field of Search ................... 552/528, 529, 552/536, 538, 623, 625, 626, 629, 630, 642, 646, 647, 648, 650; 549/416

[56] References Cited

FOREIGN PATENT DOCUMENTS 0138504  4/1985  European Pat. Off. .
0367576  5/1990  European Pat. Off. .

OTHER PUBLICATIONS

French, Andrew N., et al. "A synthesis of 7 α–substituted estradiols . . . ," Apr. 1993, MA, US, pp. 157–169 (XP–002051815).

"Synthesis of estradiol haptens." May 26, 1986, Columbus, OH (XP–002051816). (chemical abstract).

International Search Report.

*Primary Examiner*—Jose' G. Dees
*Assistant Examiner*—Alton Pryor
*Attorney, Agent, or Firm*—Miller, White, Zelano & Branigan, P.C.

[57] ABSTRACT

This invention describes new, substituted 7α-(ξ-aminoalkyl)-estratrienes of general formula I

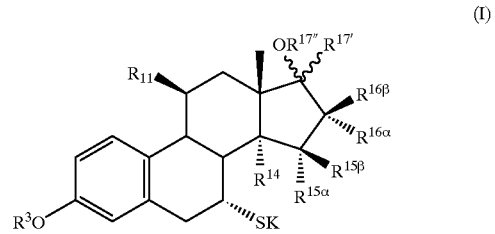

in which side chain SK is a radical of partial formula

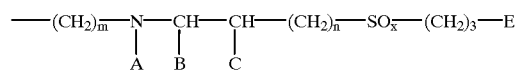

as well as their physiologically compatible addition salts with organic and inorganic acids.

The new compounds represent compounds with very strong antiestrogenic action.

The compounds according to the invention are, on the one hand, pure antiestrogens, or, on the other hand, antiestrogens with estrogenic partial action. Based on this spectrum of action, the new compounds are highly suitable for the production of pharmaceutical agents for tumor therapy and hormone replacement treatment.

11 Claims, 1 Drawing Sheet

7α-(ξ-AMINOALKYL)-ESTRATRIENES, PROCESS FOR THEIR PRODUCTION, PHARMACEUTICAL PREPARATIONS WHICH CONTAIN THESE 7α-(ξ-AMINOALKYL)-ESTRATRIENES AS WELL AS THEIR USE FOR THE PRODUCTION OF PHARMACEUTICAL AGENTS

CROSS-REFERENCE TO RELATED APPLICATION

This application is a a Divisional Application of Ser. No. 08/915,171 filed Aug. 20, 1997 now U.S. Pat. No. 5,866,560 which is related to provisional application Ser. No. 60/029,948, filed Nov. 8, 1996, which is hereby incorporated by reference.

This invention relates to substituted 7α-(ξ-aminoalkyl)-estratrienes of general formula I

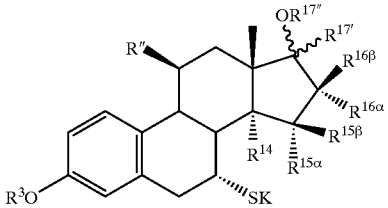

(I)

in which
side chain SK is a radical of partial formula

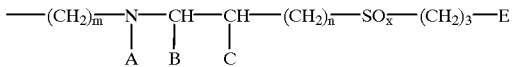

whereby m is 4, 5 or 6,
n is 0, 1 or 2,
x is 0, 1 or 2,
A is a hydrogen atom or a $C_{1-5}$ alkyl group,
B and C each are a hydrogen atom, or
A and C together are an atkylene group $—(CH_2)_p—$ with p=2, 3, 4 or 5, and C is a hydrogen atom or
A and C together are an alkylene group $—(CH_2)_q—$ with q=2, 3 or 4, and B is a hydrogen atom, and
E is an unsubstituted ethyl radical or a 1× to 5× fluorinated ethyl radical, or the terminal substituent $—(CH_2)_3—E$ in the side chain is replaced by an optionally substituted aryl or heteroaryl residue directly adjacent to or linked by up to three methylene groups to the sulfur atom,
$R^3$ is a hydrogen atom, a hydrocarbon radical with up to 8 carbon atoms or
a radical of partial formula $R^{3'}—C(O)—$, in which $R^{3'}$ is a hydrogen atom or
a hydrocarbon radical with up to 8 carbon atoms or a phenyl radical,
$R^{11}$ is a hydrogen atom, a halogen atom or a nitroxy group $—O—NO_2$,
$R^{14}$, $R^{15\alpha}$, $R^{15\beta}$, $R^{16\alpha}$ and $R^{16\beta}$ each are a hydrogen atom or
$R^{14}$ and $R^{15\alpha}$ are an additional bond or a methylene bridge, or
$R^{15\beta}$ is a methyl group and $R^{15\alpha}$ is a hydrogen atom, or
$R^{15\alpha}$ and $R^{15\beta}$ in each case are a methyl group, or
$R^{15\beta}$ and $R^{16\beta}$ together are a methylene bridge or
$R^{16\alpha}$ or $R^{16\beta}$ is a halogen atom or
$R^{16\alpha}$ and $R^{16\beta}$ together are a methylidene group
and the others of substituents $R^{14}$, $R^{15\alpha}$, $R^{15\beta}$, $R^{16\alpha}$ and $R^{16\beta}$ are each a hydrogen atom,
$R^{17'}$ in α- or β-position is a hydrogen atom, a $C_{1-5}$ alkyl, $C_{2-5}$ alkenyl or $C_{2-5}$ alkinyl group or a trifluoromethyl group and
$R^{17''}$ is a hydrogen atom or a radical of partial formula $R^{17''}—C(O)—$, in which $R^{17''}$ is a hydrogen atom or a hydrocarbon radical with up to 8 carbon atoms, or, if $R^{17'}$ is in α-position, $R^{17'}$ together with $R^{14}$ means an ethano bridge,
provided that unless A and B together stand for $—(CH_2)_p—$ or A and D together stand for $—(CH_2)_q—$, at least one of substituents $R^{11}$, $R^{14}$, $R^{15\alpha}$, $R^{15\beta}$, $R^{16\beta}$ and $R^{16\beta}$ is not a hydrogen atom,
as well as their physiologically compatible addition salts with organic and inorganic acids.

In addition, this invention relates to these compounds of general formula I as well as their physiologically compatible addition salts with pharmaceutical preparations that contain organic and inorganic acids as well as their use for the production of pharmaceutical agents.

In the compounds of general formula I, the nitrogen atom in the side chain is preferably separated by 5 methylene groups from carbon atom 7 of the steroid skeleton.

If A stands for an alkyl group with up to 5 carbon atoms, this is a methyl, ethyl, propyl, isopropyl, butyl, isobutyl, tert-butyl, pentyl, isopentyl, or neopentyl group; a methyl group is preferred as A.

Index n can assume the value 0, 1 or 2, whereby if A is a hydrogen atom or an alkyl group with up to 5 carbon atoms, value 1 is preferred for n, so that the nitrogen atom and the sulfur atom are separated by 3 methylene groups.

The nitrogen atom can be a component of a 4- to 7-membered or 5- to 7- membered) heterocycle, which is substituted in 2- or 3-position with the radical of side chain $—(CH_2)_n—SO_x—(CH_2)_3—E$.

Preferably, A and B together are a trimethylene group, i.e., together with the nitrogen atom and its adjacent carbon atom, they form a pyrrolidine ring that is substituted in 2-position.

In the latter case, value 0 is preferred for n and value 0 is preferred for x.

The sulfur atom in the side chain can be present as a simple sulfur bridge (sulfide), as sulfone or sulfoxide. The sulfides are preferred.

As radical E, an unsubstituted ethyl radical or a 1× to 5× fluorinated ethyl radical is suitable; the perfluorine radical is preferred for E.

In case of the terminal substituent $—(CH_2)_3—E$ in the side chain being replaced by an optionally substituted aryl or heteroaryl residue directly adjacent to or linked by up to three methylene groups to the sulfur atom; for the aryl residue a phenyl residue is preferred; in the case of a heteroaryl residue a 2-furyl- or 2-thienyl residue is preferred. As a substituent on this aryl or heteroaryl residue, for example, a pentafluoroethyl or trifluoromethyl group is possible; a trifluoromethyl group is preferred, preferably in the 4-position of a phenyl residue. In the case of a heteroaryl a 2-furyl- or 2-thienyl residue is spaced by one methylene group from the sulfur atom.

Substituent $R^3$ at the 3-oxygen atom is primarily a hydrogen atom. The hydroxy group can also, however, be etherified with a straight-chain or branched-chain, saturated or unsaturated hydrocarbon radical with up to 8 carbon atoms, such as, e.g., a methyl, ethyl, propyl, isopropyl, butyl, isobutyl, tert-butyl, pentyl, isopentyl, neopentyl, heptyl, hexyl or octyl radical or esterified with an acyl radical $R^{3'}$—C(O)—, in which $R^{3'}$ is a hydrogen atom or a hydrocarbon radical with up to 8 carbon atoms or a phenyl radical.

Substituents $R^{11}$ can be a hydrogen atom, a halogen atom (F, Cl, Br, I) or a nitroxy group; a fluorine atom is preferred.

If $R^{11}$ stands for a hydrogen atom or if A and B together do not stand for —$(CH_2)_p$— or if A and D together do not stand for —$(CH_2)_q$—, the D-ring exhibits a substitution from the group 14,15-double bond, 14α,15α-methylene, 15β-methyl, 15,15-dimethyl, 15β,16β-methylene, 16α- or 16β-halogen and of these especially 16α-fluorine, 16-methylidene or 14α, 17α-ethano. A 15β-methyl group or 16α-fluorine atom preferably can be mentioned.

$R^{17'}$ can be in α- or β-position.

In the case of a $C_{1-5}$ alkyl group, this is a methyl, ethyl, propyl, isopropyl, butyl, isobutyl, tert-butyl, pentyl, isopentyl or neopentyl group. As a $C_{2-5}$ alkenyl group, for example, the vinyl or allyl radical can be mentioned. Typical representatives of a $C_{2-5}$ alkinyl group are the ethinyl and 1-propinyl radicals.

If $R^{17'}$ is in α-position, especially a hydrogen atom, a methyl or trifluoromethyl group or an ethano bridge that is formed together with $R^{14}$ stands for this.

For $R^{17'}$ in β-position, primarily a hydrogen atom and a methyl group can be mentioned.

Especially those compounds of general formula I are preferred in which side chain SK is either a radical of partial formula —$(CH_2)_5$—$N(CH_3)$—$(CH_2)_3$—$SO_x$—$(CH_2)_3$—$C_2F_5$ with x=0, 1 or 2 or —$(CH_2)_5$—$N(A)$—$(CHB)$—$CH_2$—S—$(CH_2)_3$—$C_2F_5$ with A+B=—$(CH_2)_3$—. In the latter case, the compounds preferably exhibit a 17α-hydrogen atom.

Inorganic and organic acids, as they are known to one skilled in the art for forming physiologically compatible salts, are suitable for forming acid addition salts. As addition salts with acids, especially hydrochlorides and methanesulfonates can be mentioned.

The compounds below are especially preferred according to the invention:

14,17-Ethano-7α-{5-[N-methyl-N-3-(4,4,5,5,5-pentafluoropentylthio)-propylamino]-pentyl}-estra-1,3,5(10)-triene-3,17β-diol 14,17-ethano-7α-{5-[N-methyl-N-3-(4,4,5,5,5-pentafluoropentanesulfinyl)-propylamino]-pentyl}-estra-1,3,5(10)-triene-3,17β-diol 3,17β-diacetoxy-14α, 17α-ethano-7α-{5-[N-methyl-N-3-(4,4,5,5,5-pentafluoropentylthio)-propylamino]-pentyl}-estra-1,3,5(10)-triene 14,17-ethano-7α-{5-[N-methyl-N-3-(4,4,5,5,5-pentafluoropentanesulfonyl)-propylamino]-pentyl}-estra-1,3,5(10)-triene-3,17β-diol 17α-trifluoromethyl-7α-{5-[N-methyl-N-3-(4,4,5,5,5-pentafluoropentylthio)-propylamino]-pentyl}-estra-1,3,5(10)-triene-3,17β-diol 15β,16β-methano-17α-methyl-7α-{5-[N-methyl-N-3-(4,4,5,5,5-pentafluoropentylthio)-propylamino]-pentyl}-estra-1,3,5(10)-triene-3,17β-diol 15β,16β-methano-17α-methyl-7α-{[5-N-methyl-N-3-(4,4,5,5,5-pentafluoropentanesulfinyl)-propylamino]-pentyl}-estra-1,3,5(10)-triene-3,17β-diol 15β,16β-methano-7α-{5-[N-methyl-N-3-(4,4,5,5,5-pentafluoro-pentylthio)-propylamino]-pentyl}-estra-1,3,5(10)-triene-3,17β-diol 15β,16β-methano-7α-{5-[N-methyl-N-3-(4,4,5,5,5-pentafluoro-pentanesufinyl)-propylamino]-pentyl}-estra-1,3,5(10)-triene-3,17β-diol 15β-methyl-7α-{5-[N-methyl-N-3-(4,4,5,5,5-pentafluoro-pentylthio)-propylamino]-pentyl}-estra-1,3,5(10)-triene-3,17β-diol 15β,17α-dimethyl-7α-{-[N-methyl-N-3-(4,4,5,5,5-pentafluoro-pentylthio)-propylamino]-pentyl}-estra-1,3,5(10)-triene-3,17β-diol 11β-fluoro-7α-{5-[N-methyl-N-3-(4,4,5,5,5-pentafluoropentylthio)-propylamino]-pentyl }-estra-1,3,5(10)-triene-3,17β-diol 11β-fluoro-7α-{5-[N-methyl-N-3-(4,4,5,5,5-pentafluoropentanesulfinyl)-propylamino]-pentyl}-estra-1,3,5(10)-triene-3,17β-diol 11β-fluoro-7α-{5-[N-methyl-N-3-(4,4,5,5,5-pentafluoropentanesulfonyl)-propylamino]-pentyl}-estra-1,3,5(10)-triene-3,17β-diol 16α-fluoro-17α-methyl-7α-{5-[N-methyl-N-3-(4,4,5,5,5-pentafluoropentylthio)-propylamino]-pentyl}-estra-1,3,5(10)-triene-3,17β-diol 16α-fluoro-17β-methyl-7α-{5-[N-methyl-N-3-(4,4,5,5,5-pentafluoropentylthio)-propylamino]-pentyl}-estra-1,3,5(10)-triene-3,17α-diol 16α-fluoro-17α-methyl-7α-{5-[N-methyl-N-3-(4,4,5,5,5-pentafluoropentanesulfinyl)-propylarnino]-pentyl}-estra-1,3,5(10)-triene-3,17β-diol 16α-fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol 16α-fluoro-7α-{5-[N-methyl-N-3-4,4,5,5,5-pentafluoropentylthio)-propylamino]-pentyl}-estra-1,3,5(10)-triene-3,17β-diol 16α-fluoro-7α-{5-[N-methyl-N-3-(4,4,5,5,5-pentafluoropentylthio)-propylamino]-pentyl}-estra-1,3,5(10)-triene-3,17α-diol 16α-fluoro-7α-{5-[N-methyl-N-3-(4,4,5,5,5-pentafluoropentanesulfinyl)-propylamino]-pentyl}-estra-1,3,5(10)-triene-3,17β-diol 16α-fluoro-7α-{5-[N-methyl-N-3-(4,4,5,5,5-pentafluoropentanesulfonyl)-propylamino]-pentyl}-estra-1,3,5(10)-triene-3,17β-diol 7α-{5-[N-methyl-N-3-(4,4,5,5,5-pentafluoropentylthio)-propylamino]-pentyl}-estra-1,3,5(10),14-tetraene-3,17β-diol 7α-{5-[N-methyl-N-3-(4,4,5,5,5-pentafluoropentanesulfinyl)-propylamino]-pentyl}-estra-1,3,5(10),14-tetraene-3,17β-diot 7α-{5-[N-methyl-N-3-(4,4,5,5,5-pentafluoropentanesulfonyl)-propylamino]-pentyl}-estra-1,3,5(10),14-tetraene-3,17β-diol 7α-{5-[(2S)-2-(4,4,5,5,5-pentafluoropentylthiomethyl)-pyrrolidin-1-yl]-pentyl}-estra-1,3,5(10)-triene-3,17β-diol 7α-{5-[(2R)-2-(4,4,5,5,5-pentafluoropentylthiomethyl)-pyrrolidin-1-yl]-pentyl}-estra-1,3,5(10)-triene-3,17β-diol 17α-methyl-7α-{5-[2-(4,4,5,5,5-pentafluoropentylthiomethyl)-pyrrolidin-1-yl]-pentyl}-estra-1,3,5(10)-triene-3,17β-diol 11β-fluoro-7α-{5-[2-(4,4,5,5,5-pentafluoropentylthiomethyl)-pyrrolidin-1-yl]-pentyl}-estra-1,3,5(10)-triene-3,17β-diol 11β-fluoro-17α-methyl-7α-{5-[(2S)-2-(4,4,5,5,5-pentafluoropentylthiomethyl)-pyrrolidin-1-yl]-pentyl}-estra-1,3,5(10)-triene-3,17β-diol 11β-fluoro-17α-methyl-7α-{5-[(2S)-2-(4,4,5,5,5-pentafluoropentanesulfinylmethyl)-pyrrolidin-1-yl]-pentyl}-estra-1,3,5(10)-triene-3,17β-diol 3,17β-diacetoxy-11β-fluoro-17α-methyl-7α-{5-[(2S)-2-(4,4,5,5,5-pentafluoropentanesulfonylmethyl)-pyrrolidin-1-yl]-pentyl}-estra-1,3,5(10)-triene-3,17β-diol 7α-{5-[(2S)-2-(4,4,5,5,5-pentafluoropentanesulfinylmethyl)-pyrrolidin-1-yl]-pentyl-estra-1,3,5(10)-triene-3,17β-diol 7α-{5-[(2S)-2-(4,4,5,5,5-pentafluoropentanesulfonylmethyl)-pyrrolidin-1-yl]-pentyl-estra-1,3,5(10)-triene-3,17β-diol 11β-fluoro-17α-methyl-7α-{5-[N-methyl-N-3-(4,4,5,5,5-pentafluoropentylthio)-propylamino]-pentyl}-estra-1,3,5(10)-triene-3,17β-diol 11β-fluoro-17α-methyl-7α-{5-[N-methyl-N-3-(4,4,5,5,5-pentafluoropentanesulfinyl)-propylamino]-pentyl}-estra-1,3,5(10)-triene-3,17β-diol 11β-fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol 11β-fluoro-7α-{5-[N-methyl-N-2-(4,4,5,5,5-pentafluoropentanesulfonyl)-ethylamino]-pentyl}-estra-1,3,5(10)-triene-3,17β-diol 11β-fluoro-7α-{5-[N-methyl-N-3-(4,4,5,5,5-pentafluoropentylthio)-propylamino]-pentyl}-3-hydroxy-estra-1,3,5(10)-triene-17-one 11β-fluoro-7α-{6-[N-methyl-N-3-(4,4,5,5,5-pentafluoropentylthio)-propylamino]-hexyl}-estra-1,3,5(10)-triene-3,17β-diol 11β-fluoro-7α-{6-[N-methyl-N-3-(4,4,5,5,5-pentafluoropentanesulfinyl)-propylamino]-hexyl}-estra-1,3,5(10)-triene-3,17β-diol 11β-fluoro-7α-(5-{[N-3-(furan-2-ylmethylthio)-propyl]-N-methyl-amino}-pentyl)-estra-1,3,5(10)-triene-3,17β-diol 11β-fluoro-7α-(5-{N-methyl-[N-3-(thiophen-2-ylmethylthio)-propyl]-amino}-pentyl)-estra-1,3,5(10)-triene-3,17β-diol 11β-fluoro-7α-{5-[(2S)-2-(4-trifluoromethylphenylthiomethyl)-pyrrolidin-1-yl]-pentyl}-estra-1,3,5(10)-triene-3,17β-diol 11β-fluoro-17α-methyl-7α-{5-[(2S)-2-(4,4,5,5,5-pentafluoropentanesulfinyl-methyl)-pyrrolidin-1-yl]-pentyl}-estra-1,3,5(10)-triene-3,17β-diol 11β-fluoro-17α-methyl-7α-{5-[(2R)-2-(4,4,5,5,5-pentafluoropentylthiomethyl)-pyrrolidin-1-yl]-pentyl}-estra-1,3,5(10)-triene-3,17β-diol 11β-fluoro-7α-{5-[(2S)-2-(4,4,5,5,5-pentafluoropentylthiomethyl)-pyrrolidin-1-yl]-pentyl}-estra-1,3,5(10)-triene-3,17β-diol 11β-fluoro-7α-{5-[(2S)-2-(4,4,5,5,5-pentafluoropentanesulfinylmethyl)-pyrrolidin-1-yl]-pentyl}-estra-1,3,5(10)-triene-3,17β-diol 11β-fluoro-7α-{5-[(2S)-2-(4,4,5,5,5-pentafluoropentanesulfonylmethyl)-pyrrolidin-1-yl]-pentyl}-estra-1,3,5(10)-triene-3,17β-diol.

The compounds of general formula I represent compounds with very strong antiestrogenic action.

The compounds according to the invention are, on the one hand, pure antiestrogens, or, on the other hand, so-called partial antagonists, i.e., antiestrogens with estrogenic partial action such as tamoxifen or raloxifen. The agonistic, estrogenic action is clearly less pronounced than in tamoxifen, however, in the compounds according to the invention in each case. Unlike tamoxifen, in the case of the partial antagonists of general formula I, their agonistic, estrogenic action occurs in a tissue-selective manner. The agonistic action especially occurs on bones, in the cardiovascular system and in the CNS (central nervous system). No agonistic action occurs especially on the uterus.

Compounds with antiestrogenic properties, i.e., substances with inhibiting actions relative to estrogens, have already been described extensively.

As the compounds that come closest structurally to the compounds in question here of general formula I, on the one hand, the steroid derivatives that are described in EP-A 0138 504 can be considered, and of the latter especially 7α-[9-(4,4,5,5,5-pentafluoropentylsulfinyl)-n-nonyl]-estra-1,3,5(10)-triene-3,17β-diol (EP-A 0 138 504, page 58, penultimate compound). This compound is currently under clinical development for hormone-dependent tumors (breast cancer) and represents the compound that is best known at this time, i.e., the one with the strongest antiestrogenic activity, of these steroid derivatives.

Pharmaceutical compositions that contain sex steroid inhibitors and exhibit a steroidal skeleton, which exhibits a 7α-side chain with the simultaneous presence of at least one other substituent in 14-, 15- or 16-position, are the object of EP-A 0 376 576 and are also to be considered as the closest prior art.

A considerable number of the most varied compounds— i.a., those of steroidal origin and those with a 2-phenylindole skeleton—which act as antiestrogens and/or suppress the estrogen biosynthesis, are disclosed in WO 93/10741.

Other steroidal antiestrogens are described in EP-AS 0 384 842 and 0 629 635, which have an 11β-phenyl radical.

In the compounds according to the invention, there are antiestrogens with stronger, several times better, antiestrogenic action than the already mentioned 7α-[9-(4,4,5,5,5-pentafluoropentylsulfinyl)-n-nonyl]-estra-1,3,5(10)-triene-3,17β-diol.

The compounds of general formula I according to this application are distinguished in comparison to the already known steroid derivatives according to EP-A 0 138 504 and EP-A 0 367 576 by novel side chains on carbon atom 7 of the steroid skeleton. This structural modification results in especially greatly antiestrogenically active compounds, as was demonstrated in a transactivation test.

In addition, relative to the compounds of EP-A 0 138 504, the compounds of general formula I are distinguished with respect to the substitution on carbon atom 11 and/or of the D-ring (except in the case that A and B together stand for —(CH$_2$)$_p$— or A and D together stand for —(CH$_2$)$_q$—). In comparison to the compounds of EP-A 0 367 576, the compounds of general formula I on carbon atom 11 and/or in the D ring can carry the same or other substituents.

By the disclaimer in the definition of general formula I, compounds that are described from their scope in non-prepublished DE P 196 22 457 are excluded.

EXAMPLES

Figure 1:
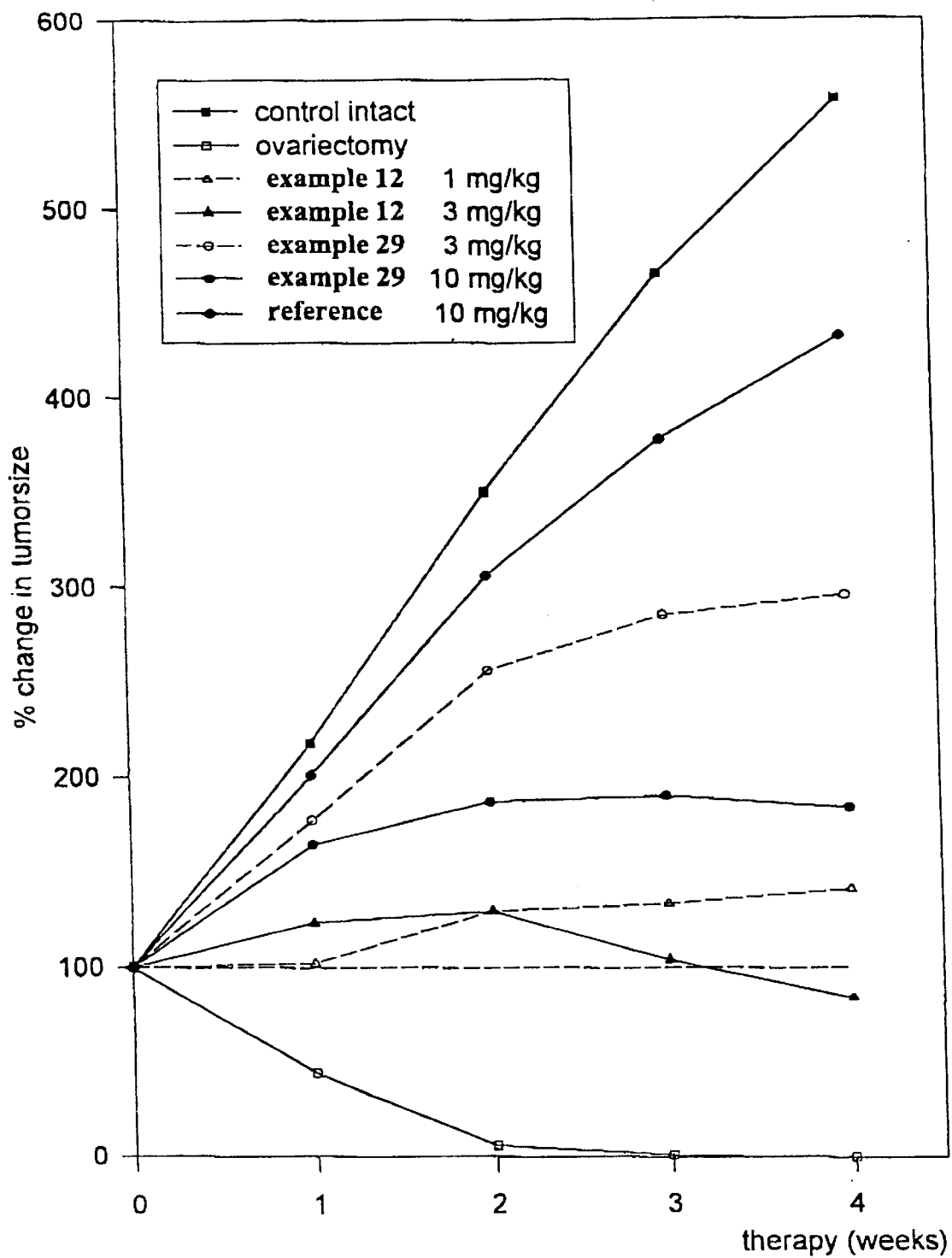
FIG. 1 is a graph of the change in rumor size in rats upon treatment with compounds according to the invention and comparative compounds.

The antiestrogenic action of the compounds according to the invention was determined in transactivation assays [Demirpence, E.; Duchesne M.-J.; Badia, E.; Gagne, D. and Pons, M.: MVLN Cells: A Bioluminescent MCF-b 7-Derived Cell Line to Study the Modulation of Estrogenic Activity; J. Steroid. Molec. Biol. Vol. 46, No. 3, 355–364 (1993) as well as Berry, M.; Metzeger D.; Chambon, P.: Role of the Two Activating Domains of the Estrogen Receptor in the Cell-type and Promoter-context Dependent Agonistic Activity of the Anti-estrogen 4-Hydroxytamoxifen; The EMBO Journal Vol. 9, 2811–28181 (1990)].

The HeLa cells are transiently transfixed with human estrogen receptor-expression vector (HEGO) and Vit-TK-CAT reporter genes, and the MVLN cells are transfixed in a stable manner with reporter gene Vit-TK-LUC. The estrogenic action was determined in the presence of 0.1 Nm of estradiol.

The IC$_{50}$ values for the new compounds lie in the nanomolar range. In the HeLa cell line as well as the MVLN cell line, the following IC$_{50}$ values are produced for the compounds of Examples 12, 15, 18, 25, 29, 31 and 36 as well as for 7α-[9-(4,4,5,5,5-pentafluoropentylsulfinyl)-n-nonyl]-estra-1,3,5(10)-triene-3,17β-diol (execution of test according to the above-indicated bibliographic references):

| Compound | $IC_{50}$ [nM] | |
|---|---|---|
| | HeLa cells | MVLN cells |
| Example 12 | 0.06 | 2.4 |
| Example 15 | 0.06 | 1.4 |
| Example 18 | 0.05 | 0.13 |
| Example 25 | 0.06 | 0.15 |
| Example 29 | 0.13 | 0.2 |
| Example 31 | 0.1 | 0.2 |
| Example 36 | 0.05 | 0.4 |
| Reference: | | |
| 7α[9-(4,4,5,5,5-pentafluoro-pentanesulfinyl)-nonyl]-estra-1,3,5(10)triene-3,17β-diol | 0.5 | 6.0 |

In vivo tests also impressively confirm the superiority of the compounds according to the invention compared to 7α-[9-(4,4,5,5,5-pentafluoropentanesulfinyl)-nonyl]-estra-1,3,5(10)-triene-3,17β-diol. The tests described below were carried out:

1. Uterus growth test in infantile rats, p.o. (test for antiestrogenic action)
2. Tumor tests of anti-tumor effect on hormone-dependent breast cancer)

DMBA*—induced breast cancer in rats

*=dimethylbenzanthracene

1. Uterus Growth Test in Infantile Rats
(Antiestrogenic Action)
Principle of the Method In rodents, the uterus reacts to the administration of estrogens with an increase in weight (both proliferation and water retention). This growth is to be inhibited in a dose-dependent manner by simultaneous administration of compounds with an antiestrogenic action.
Execution of the Test
Animals:

Infantile female rats at a weight of 35–45 g at the beginning of the test, 5-6 animals per dose.
Formulation and Administration of the Substances:

For p.o. administration, the substances are dissolved in 1 part of ethanol (E) and made up with 9 parts of peanut oil (EÖ).
Test Batch Young rats that have just been weaned from their mothers are delivered one day before the beginning of treatment for acclimatization and are immediately supplied with food—still in the animal cage. The treatment is then carried out once a day for 3 days in combination with 0.5 μg of estradiol benzoate (EB). EB is always administered subcutaneously (s.c.), while the test substance is administered or p.o. (perorally). 24 hours after the last administration, the animals are weighed and killed, and the uteri are removed. The wet weights (without contents) are determined from the prepared uteri.
Controls Negative control: vehicle (E/EÖ), 0.2 ml/animal/day Positive control: 0.5 μg of EB/0.1 ml/animal/day
Analysis For each group, the average values with standard deviation (X+SD), as well as the significance of the differences compared to the control group (EB) in the Dunnett Test (p<0.05), are determined from the relative organ weights (mg/100 g of body weight). The calculation of inhibition (in %) compared to the EB control is done with a program. The relative effects of the test substances are determined by covariance and regression analysis.

Antiuterotrophic activity in rats (infantile rats treated with 0.5 μg estradiol benzoate)

| | 0.1 mg/kg p.o. | |
|---|---|---|
| Example | % inhibition | $IC_{50}$ |
| 12 | 91 | 0.01 |
| 15 | 33 | 0.24 |
| 18 | 16 | >0.3 |
| 29 | 80 | 0.01 |
| 31 | 71 | 0.04 |
| 36 | 62 | 0.03 |
| Reference | 8 | 0.39 |

These results demonstrate the much stronger antiestrogenic potency of the compounds of general formula I compared to the reference compound 7α-[9-(4,4,5,5,5-pentafluoropentanesulfinyl)-nonyl]-estra-1,3,5(10)-triene-3, 17β-diol after oral administration. The compounds of the invention exert a better bioavailability after oral administration.

Pure antiestrogens according to the present invention are those compounds of the general formula I which in the in vitro test for the detection of estrogenic activity described thereafter show no or only marginal agonistic activity (preferably, 10% or less estradiol activity).

The partial estrogenic activity was determined in trans-activation assays. HeLa cells were transiently transfixed with human estrogen receptor-expression vector (HEGO) and a reporter gene rPR-TK-CAT. This reporter gene contains the "Estrogen Responsive Element" of the rabbit progesterone receptor gene (+698/+729-region) in front of a TK-CAT gene (Savouret, J. F., Bailly A., Misrahi M., Rauch C., Redeuilh G., Chauchereau A., Milgrom E.; Characterization of the hormone responsive element involved in the regulation of the progesterone receptor gene. EMBO J. 10:1875–1883 (1991)).

The estrogenic potency was determined at a concentration of 1 μM.

| Compound of Example | Activation of rPR-TK-promoter [% of estradiol]* |
|---|---|
| 12 | −11 |
| 15 | −25 |
| 18 | −24 |
| 25 | −21 |
| 29 | 10 |
| 31 | −5 |
| 36 | −6 |
| Reference ZM 182780 | −15 |

*Negative values: suppression of reporter gene activity below levels of the control.

2. Tumor Test
Influencing Tumor Growth in the DMBA * Model in Rats (DMBA Tumor Model)
*b 9,10-Dimethyl-1,2-benanthracene
Biological Principle The growth of the DMBA-induced breast neoplasm of rats is largely dependent on estrogens and prolactin. Active antiestrogens, antigestagens, and aromatase inhibitors result in the inhibition of tumor growth, and substances that have antigonadotropic and androgenic properties also exert a tumor-inhibiting action.

Animal Material

45–47-day-old female rats (Sprague-Dawley, breeder ZiH or Möllegard), 8–10 animals per group.

Test Batch

The animals receive 10 mg of DMBA orally on a one-time basis. Then, the animals are examined weekly by palpation for tumor development. Six to 10 weeks after DMBA treatment, approximately 1 to 10 tumors develop per animal. The tumor size is determined once a week with the aid of a sliding gauge. If at least one tumor has reached a specific size (150 mm$^2$ of tumor surface area), an ovariectomy is performed on the animals, or the treatment of the animals with the test substance begins. The treatment is carried out in most cases daily for a period of about 28 days. The tumor size is subsequently determined once a week.

Analysis

The total tumor size per animal is determined before the beginning of treatment (initial values). For each group, the average values of the percentage changes of the tumor size relative to the initial value are then calculated. In addition, the percentage of animals per group is determined, whose tumors in each case: (1) have totally disappeared (total regression); partially disappeared (partial regression); (3) are unchanged (no change); or (4) are further enlarged (enlargement).

The values that are found are tested for significance in the Dunnett Test and are plotted graphically.

Test Results

At an oral dose of 3 mg/kg/day, 11β-fluoro-7α-{5-[2-(4,4,5,5,5-pentafluoropentylthiomethyl)-pyrrolidin-1-yl]-pentyl}-estra-1,3,5(10)-triene-3,17β-diol (compound of Example 29) inhibits tumor growth more effectively than an oral dose of 10 mg/kg/day. 7α-[9-(4,4,5,5,5-pentafluoropentanesulfinyl)-nonyl]-estra-1,3,5(10)-triene-3,17β-diol exerts only a slight action at this dose compared to the intact control. (FIG. 1).

Oral doses of 1 and 3 mg/kg/day 11β-fluoro-7α-{5-(N-methyl-N-3-(4,4,5,5,5-pentafluoropentylthio)-propylamino]-pentyl}-estra-1,3,5(10)-TRIENE-3,17β-diol (the compound of Example 12) are even more potent than 10 mg of the compound of Example 29. These results clearly demonstrate the superiority of the present invention's compounds over the prior art represented by the reference compound 7α-[9-(4,4,5,5,5-pentafluoropentanesulfinyl)-nonyl]-estra-1,3,5(10)-triene-3,17β-diol (FIG. 1).

The compounds according to the invention, especially if they are pure antiestrogens, thus are suitable for treatment of estrogen-dependent diseases, for example, breast cancer (for example, instead of tamoxifen, or, as a second-line therapy for tamoxifen resistant carcinomas), endometrial carcinoma, prostatic hyperplasia, anovulatory infertility and melanoma. The pure antiestrogens of general formula I can further be used as component in the products described in EP 0 346 014 B1 comprising an estrogen and a pure antiestrogen for simultaneous, sequential or separate use in selective estrogen therapy of peri- or post-menopausal conditions.

The compounds of the general formula I, especially if they are pure antiestrogens, can be used together with antiprogestines (competitive progesterone antagonists) in the treatment of hormone-dependent tumors (EP 0 310 542 B1).

Additional indications for the compounds of general formula I, especially if they are pure antiestrogens, is treatment of male pattern alopecia, diffuse alopecia, chemotherapy-induced alopecia, as well as hitsutism. (Hye-Sun Oh and Robert C. Smart, Proc. Natl. Acad. Sci., USA, 93 (1996), 12525–12530).

Further, the compounds of the invention can be used to produce medicaments for treating endometriosis and ovarial carcinoma.

It is further possible to use the compounds of the invention for the production of pharmaceutical compositions for male and emale fertility control (male FC: DE-A 195 10 862.0).

The compounds of general formula I with tissue-selective estrogenic partial action primarily can be used for prophylaxis and treatment of osteoporosis and for the production of preparations for substitution therapy in pre-, peri- and post-menopause (HRT) (Black, L. J.; Sato, M.; Rowley, E. R.; Magee D. E.; Bekele, A.; Williams, D. C.; Cullinan, G. J.; Bendele, R.; Kauffinan, R. F.; Bensch, W. R.; Frolik, C. A.; Termine, J. D. and Bryant, H. U.: Raloxifene (LY 139481 Hcl] Prevents Bone Loss and Reduces Serum Cholesterol without Causing Uterine Hypertrophy in Ovariectomized Rats; J. Clin. Invest. 93: 63–69, 1994). The estrogenic partial action occurs only on the desired target organ.

The invention also relates to pharmaceutical preparations, which contain at least one compound of general formula I (or physiologically compatible addition salts with organic and inorganic acids of them), and the use of these compounds for the production of pharmaceutical agents, especially for treating estrogen-dependent diseases and tumors and pharmaceutical agents for hormone replacement treatment (HRT).

The compounds according to the invention and the acid addition salts are suitable for the production of pharmaceutical compositions and preparations. The pharmaceutical compositions or pharmaceutical agents contain as active ingredient one or more of the compounds according to the invention or their acid addition salts, optionally in a mixture with other pharmacologically or pharmaceutically active substances. The production of the pharmaceutical agents is carried out in a known way, whereby the known and commonly used pharmaceutical adjuvants as well as other commonly used vehicles and diluents can be used.

As such vehicles and adjuvants, for example, those are suitable which are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pp. 1 to 39; Journal of Pharmaceutical Sciences, Volume 52 (1963), pp. 918 and ff.; H. v. Czetsch-Lindenwald, Hilfsstoffe für Pharmazie und angrenzende Gebiete [Adjuvants for Pharmaceutics and Related Fields; Pharm. Ind. Number 2, 1961, pp. 72 and ff.; Dr. H. P. Fiedler, Lexikon der Hilfsstoffe für Pharmazie, Kosmetik und angrenzende Gebiete [Encyclopedia of Adjuvants for Pharmaceutics, Cosmetics and Related Fields], Cantor KG. Aulendorf in Würtemberg 1971.

The compounds can be administered orally or parenterally, for example, intraperitoneally, intramuscularly, subcutaneously or percutaneously. The compounds can also be implanted in tissue. The amount of the compounds to be administered varies within a wide range and can cover any effective amount. Depending on the condition to be treated and the type of administration, the amount of administered compound is 0.1–25 mg/kg of body weight, preferably 0.5–5 mg/kg of body weight, per day. In humans, this corresponds to a daily dose of 5 to 1250 mg. Preferred daily dose in humans is 50 to 200 mg.

For oral administration, capsules, pills, tablets, coated tablets, etc., are suitable. In addition to the active ingredient, the dosage units can contain a physiologically compatible vehicle, such as, for example, starch, sugar, sorbitol, gelatin, lubricant, silicic acid, talc, etc. The individual dosage units for oral administration can contain, for example, 5 to 500 mg of active ingredient.

To achieve a better bioavailabinfity of the active compounds, the compounds can also be formulated as cyclodextnfin clathrates. In this connection, the compounds with α-, β- or γ-cyclodextrin or their derivatives are reacted (PCT/EP95/02656).

For parenteral administration, the active ingredients can be dissolved or suspended in a physiologically compatible diluent. As a diluent, very frequently oils with or without the addition of a solubilizer, a surfactant, a suspending agent or emulsifier are used. Examples of oils that are used are olive oil, peanut oil, cottonseed oil, soybean oil, castor oil and sesame oil.

The compounds can also be used in the form of a depot injection or an implant preparation, which can be formulated so that a delayed release of acid is made possible.

Implants can contain, as inert materials, for example, biodegradable polymers or synthetic silicones, such as, for example, silicone rubber. In addition, the active ingredients can be added to, for example, a patch.

The compounds according to the invention can be produced as described below. The following examples are used for a more detailed explanation of the invention. By an analogous approach using reagents like those in the data contained in the Examples, all compounds of general formula I can be obtained. The saponification of the ester groupings as well as esterification and etherification of free hydrogen groups is carried out in each case according to established processes of organic chemistry. By observing the differing reactivity of the esterified and free 3- and 17-hydroxy groups, the 3,17-diesters can be cleaved selectively in 3-position, and the 3-hydroxy-17-acyloxy compound can then be additionally functionahized specifically in the 3-position; it is equally possible to esterify or to etherify the 3,17-dihydroxy compound selectively only in the 3-position and then to introduce specifically another radical into the 17-position as already in the 3-position. The acid addition salts of the compounds of general formula I can also be produced according to standard processes from the compounds of general formula I.

EXAMPLE 1

14,17-Ethano-7α-{5-[N-methyl-N-3-(4,4,5,5,5-pentafluoropentylthio)-propylamino]-pentyl}-estra-1,3,5(10)-triene-3,17β-diol a) 7α-(5-tert-Butyldimethylsilyloxypentyl)-estr-4-ene-3,17-dione In 70 ml of absolute tetrahydrofuran, 15.1 g of Mg chips with 175.6 g of 1-bromo-5-tert-butyl-dimethylsilyloxypentane [Tetrahedron Letters 23, 1982, 40, 4147–4150], dissolved in 600 ml of absolute tetrahydrofuran, are reacted to form the Grignard reagent. 59 g of copper(I) iodide is added to this solution, cooled to –20° C, under a nitrogen stream, and then 50 g of estra-4,6-diene-3,17-dione [Steroids Vol. 1, 1963, 233–249], dissolved in 300 ml of absolute THF, is added in drops within one hour. For working-up, 37.5 ml of acetic acid is added in drops, the reaction mixture is diluted with ethyl acetate, washed with saturated ammonium chloride solution, water and sodium bicarbonate solution and dried. The residue that is obtained after the concentration by evaporation is chromatographed on silica gel. 35.4 g of 7α-(5-tert-butyldimethylsilyloxypentyl)-estr-4-ene-3,17-dione is obtained. $[\alpha]_D^{22}=+52.8°$ (c=0.535% in chloroform)

b) 7α-(5-Hydroxypentyl)-estr-4-ene-3,17-dione

A solution of 125.4 g of 7α-(5-tert-butyldimethylsilyloxypentyl)-estr-4-ene-3,17-dione in 625 ml of methanol and 347 ml of water is stirred with 694 ml of glacial acetic acid for 2.5 hours at 50° C. After the concentration by evaporation at 60° C. in a vacuum, 94.1 g of crude 7α-(5-hydroxypentyl)-estr-4-ene-3,17-dione is obtained as oil.

c) 7α-(5-Acetoxypentyl)-estr-4-ene-3,17-dione

A solution of 94 g of crude 7α-(5-hydroxypentyl)-estr4-ene-3,17-dione in 620 ml of pyridine is slowly mixed with 310 ml of acetic anhydride and stirred for 2 hours at 25° C. Then, it is slowly mixed with 116 ml of water while being cooled with ice, diluted with 31 of diethyl ether, the organic phase is dried and concentrated by evaporation after washing with sodium bicarbonate solution. The residue is chromatographed on silica gel, and 84.4 g of 7α-(5-acetoxypentyl)-estr-4-ene-3,17-dione is obtained as oil.

d) 7α-(5-Acetoxypentyl)-3-hydroxy-estra-1,3,5(10)-trien-17-one 17.8 g of lithium bromide and 92.83 g of copper(II) bromide are added to a solution of 82.3 g of 7α-(5-acetoxypentyl)-estr-4-ene-3,17-dione in 936 ml of acetonitrile at a bath temperature of 80° C. After 10 minutes at a bath temperature of 80° C., the reaction solution is cooled, extracted three times with ethyl acetate, washed with water and sodium bicarbonate solution and dried. The residue that is obtained after the concentration by evaporation is chromatographed on silica gel, and 60.4 g of 7α-(5-acetoxypentyl)-3-hydroxy-estra-1,3,5(10)-trien-17-one is obtained as oil.

e) 3-Acetonxy-7α-(5-acetonxypentyl)-estra-1,3,5(10)-trien-10-one

A solution of 60.4 g of 7α-(5-acetoxypentyl)-3-hydroxy-estra-1,3,5(10)-trien-17-one in 300 ml of pyridine is stirred with 150 ml of acetic anhydride for 1 hour at room temperature. Then, it is precipitated with a mixture of ice/water/common salt/hydrochloric acid, taken up with ethyl acetate, washed neutral with sodium bicarbonate and common salt solution, and dried on sodium sulfate and concentrated by evaporation in a vacuum. 63.9 g of 3-acetoxy-7α-(5-acetoxypentyl)-estra-1,3,5(10)-trien-17-one is obtained as oil.

f) 3-Acetoxy-7α-(5-acetoxypentyl)-17,17-ethylenedioxy-estra-1,3,5(10)-triene

A solution of 63.9 g of 3-acetoxy-7α-(5-acetoxypentyl)-estra-1,3,5(10)-trien-17-one in 460 ml of dichloromethane is stirred with 460 ml of ethylene glycol, 155 ml of trimethyl orthoformate and 1.2 g of para-toluenesulfonic acid for 3 hours at a bath temperature of 50° C. Then, it is diluted with dichloromethane, washed with sodium bicarbonate and common salt solution and dried on sodium sulfate, concentrated by evaporation in a vacuum and chromatographed on silica gel with hexane/ethyl acetate. 63.2 g of 3-acetoxy-7α-(5-acetoxypentyl)-17,17-ethylenedioxy-estra-1,3,5(10)-triene is obtained as oil.

g) 3Acetony-7α-(5-acetoxypentyl)-16α-bromo-17,17-ethylenedioxy-estra-1,3,5(10)-triene A solution of 63.2 g of 3-acetoxy-7α-(5-acetoxypentyl)-17,17-ethylenedioxy-estra-1,3,5(10)-triene in 630 ml of tetrahydrofuran is mixed in portions at 0° C. with 61.7 g of pyridine hydrobromide perbromide, and it is stirred for 2 hours at 0° C. Then, a solution of 15 g of sodium sulfide in 70 ml of water is added, diluted with ethyl acetate, washed with sodium bicarbonate and common salt solution and dried on sodium sulfate and concentrated by evaporation in a vacuum. 74.1 g of 3-acetoxy-7α-(5-acetoxypentyl)-16α- bromo-17,17-ethylenedioxy-estra-1,3,5(10)-triene is obtained as oil.

h) 17,17-Ethylenedioxy-7α-(5-hydroxypentyl)-estra-1,3,5(10),15-tetraen-3-ol

A solution of 74.1 g of 3-acetoxy-7α-(5-lacetoxypentyl)-16α-bromo-17,17-ethylenedioxy-estra-1,3,5(10)-triene in 740 ml of dimethyl sulfoxide and 74 ml of methanol is stirred with 74 g of potassium hydroxide for 7.5 hours at a bath temperature of 85° C. Then, it is precipitated with ice/water/common salt, taken up with ethyl acetate, washed neutral, dried on sodium sulfate, concentrated by evaporation in a vacuum and chromatographed on silica gel with hexane/ethyl acetate. 36.12 g of pure 17,17-ethylenedioxy-7α-(5-hydroxypentyl)-estra-1,3,5(10),15-tetraen-3-ol is obtained as foam.

i) 3-Hydroxy-7α-(5-hydroxypentyl)-estra-1,3,5(10),15-tetraen-17-one

A solution of 36.12 g of 17,17-ethylenedioxy-7α-(5-hydroxypentyl)-estra-1,3,5(10),15-tetraen-3-ol in 958 ml of acetone and 111 ml of water is stirred for 2 hours at room temperature with 2.76 g of para-toluenesulfonic acid. Then, it is concentrated by evaporation in a vacuum to ⅓ of the volume, taken up with ethyl acetate, washed neutral, dried on sodium sulfate and concentrated by evaporation in a vacuum. 31.7 g of 3-hydroxy-7α-(5-hydroxypentyl)-estra-1,3,5(10),15-tetraen-17-one is obtained as crystals with a melting point of 194–196° C.

j) 3,17-Diacetoxy-7α-(5-acetoxypentyl)-estra-1,3,5(10),14,16-pentaene

A solution of 15.7 g of 3-hydroxy-7α-(5-hydroxypentyl)-estra-1,3,5(10),15-tetraen-17-one in 330 ml of acetic anhydride is stirred with 4.6 g of para-toluenesulfonic acid for 4 hours at room temperature. Then, it is precipitated with pyridine/water/common salt, taken up in ethyl acetate, washed with sodium bicarbonate and common salt solution, dried on sodium sulfate, concentrated by evaporation in a vacuum and chromatographed on silica gel with hexane/ethyl acetate. 11.1 g of pure 3,17-diacetoxy-7α-(5-acetoxypentyl)-estra-1,3,5(10),14,16-pentaene is obtained as oil.

k) 3,17β-Diacetoxy-7α-(5-acetoxypentyl)-14α,17α-etheno-estra-1,3,5(10)-triene 11.0 g of 3,17-diacetoxy-7α-(5-acetoxypentyl)-estra-1,3,5(10),14,16-pentaene in 120 ml of benzene is treated at 300 bar and 175° C. for 6.5 days with ethene. Then, it is taken up in ethyl acetate, washed with sodium bicarbonate and common salt solution, dried on sodium sulfate, concentrated by evaporation in a vacuum and chromatographed on silica gel with hexane/ethyl acetate. 8.4 g of 3,17β-diacetoxy-7α-(5-acetoxypentyl)-14α, 17α-etheno-estra-1,3,5(10)-triene is obtained as foam.

l) 3,17β-Diacetoxy-7α-(5-acetoxypentyl)-14α,17α-ethano-estra-1,3,5(10)-triene

A solution of 8.4 g of 3,17β-diacetoxy-7α-(5-acetoxypentyl)-14α,17α-etheno-estra-1,3,5(10)-triene in 200 ml of ethyl acetate is shaken with 1.5 g of palladium (10%) on carbon for one hour at room temperature with hydrogen. Then, it is suctioned off on Celite, rewashed with ethyl acetate, concentrated by evaporation in a vacuum and chromatographed on silica gel with hexane/ethyl acetate. 6.0 g of 3,17β-diacetoxy-7α-(5-acetoxypentyl)-14α,17α-ethano-estra-1,3,5(10)-triene is obtained as foam.

m) 14α,17α-Ethano-7α-(5-hydroxypentyl)-estra-1,3,5(10)-triene-3,17α-diol

A solution of 6.0 g of 3,17β-diacetoxy-7α-(5-acetoxypentyl)-14α,17α-ethano-estra-1,3,5(10)-triene in 100 ml of a 1-molar potassium hydroxide solution is allowed to stand for 7.5 hours at room temperature. Then, it is poured onto 1-molar hydrochloric acid, extracted three times with ethyl acetate, washed with sodium bicarbonate and common salt solution, dried on sodium sulfate, concentrated by evaporation in a vacuum and recrystallized from acetone/hexane. 4.57 g of 14α,17α-ethano-7α-(5-hydroxypentyl)-estra-1,3,5(10)-triene-3,17,-diol is obtained as colorless crystals with a melting point of 63–65° C.

n) 3-Benzyloxy-14α,17α-ethano-7α-(5hydroxypentyl)-estra-1,3,5(10)-trien-17β-ol

A solution of 4.5 g of 14α,17α-ethano-7α-(5-hydroxypentyl)-estra-1,3,5(10)-triene-3,17β-diol in 90 ml of acetonitrile is stirred with 1.91 g of potassium carbonate and 1.53 ml of benzyl bromide for 6.5 hours at a bath temperature of 80° C. Then, it is concentrated by evaporation in a vacuum to ⅓ of the volume, added to water, extracted three times with ethyl acetate, washed neutral, dried on sodium sulfate, concentrated by evaporation in a vacuum and chromatographed on silica gel with dichloromethane/acetone. 4.8 g of 3-benzyloxy-14α,17α-ethano-7α-(5-hydroxypentyl)-estra-1,3,5(10)-trien-7β-ol is obtained as foam.

o) 3Benzyloxy-14α,17α-ethano-7α-(5tosyloxypentyl)-estra-1,3,5(10)-trien-17β-ol

A solution of 4.8 g of 3-benzyloxy-14α,17α-enihano-7α-(5-hydroxypentyl)-estra-1,3,5(10)-trien-17β-ol in 50 ml of pyridine is stirred at 0° C. with 3.63 g of toluenesulfonic anhydride for 4 hours. Then, it is diluted with ethyl acetate, extracted with 2-molar hydrochloric acid, washed neutral, dried on sodium sulfate, concentrated by evaporation in a vacuum and chromatographed on silica gel with hexane/ethyl acetate. 4.75 g of 3-benzyloxy-14α,17α-ethano-7α-(5-tosyloxypentyl)-estra-1,3,5(10)-trien-17β-ol is obtained as foam.

p) 3-Benzyloxy-14α,17α-ethano-7α-{5-[N-methyl-N-3-(4,4,5,5,5-pentafluoropentylthio)-propylamino]-pentyl}-estra-1,3,5(10)-trien-17β-ol A solution of 4.7 g of 3-benzyloxy-14α,17α-ethano-7α-(5-tosyloxypentyl)-estra-1,3,5(10)-trien-17β-ol in 100 ml of dimethylformamide is stirred with 2.7 g of methyl-[3-(4,4,5,5,5-pentafluoropentylthio)-propyl]-amine for 4 hours at a bath temperature of 80° C. Then, it is added to water, extracted three times with ethyl acetate, washed with common salt solution, dried on sodium sulfate, concentrated by evaporation in a vacuum and chromatographed on silica gel with dichloromethane/methanol. 3.8 g of 3-benzyloxy-14α,17α-ethano-7α-{5-[N-methyl-N-3-(4,4,5,5,5-pentafluoropentylthio)-propylamino]-pentyl}-estra-1,3,5(10)-trien-17β-ol is obtained as oil.

q) 14α,17α-Ethano-7α-{5-[N-methyl-N-3-(4,4,5,5,5-pentafluoropentylthio)-propylamino]-pentyl}-estra-1,3,5(10)-triene-3,17β-diol A solution of 3.7 g of 3-benzyloxy-14α,17α-ethano-7α-{5-[N-methyl-N-3-(4,4,5,5,5-pentafluoropentanesulfinyl)-propylamnino]-pentyl}-estra-1,3,5(10)-trien-17β-ol in 65 ml of dichloromethane is stirred at 0° C. with 2.1 ml of N,N-dimethylaniline for 5 minutes, mixed with 2.75 g of anhydrous aluminum chloride and stirred for 3.5 hours at 0° C. Then, it is mixed with saturated, aqueous potassium sodium tartrate solution, added to water, extracted three times with dichloromethane, washed neutral, dried on sodium sulfate and concentrated by evaporation in a vacuum. 6.3 g of crude product, which is chromatographed on silica gel with dichloromethanelmethanol, is obtained. 2.85 g of pure 14α,17α-ethano-7α-{5-[N-methyl-N-3-(4,4,5,5,5-pentafluoropentylthio)-propylamino]-pentyl}-estra-1,3,5(10)-triene-3,17β-diol is obtained as crystals with a melting point of 63–67° C., $[\alpha]_D^{22}$=+19.4° (c=0.505% in chloroform).

EXAMPLE 2

14,17-Ethano-7α-{5-[N-methyl-N-3-(4,4,5,5,5-pentafluoropentanesulfinyl)-propylamino]-pentyl}-estra-1,3,5(10)-triene-3,17β-diol A solution of 1.0 g of 14α,17α-ethano-7α-{5-[N-methyl-N-3-(4,4,5,5,5-pentafluoropentylthio)-propylamino]-pentyl}-estra-1,3,5(10)-triene-3,17β-diol in 37.5 ml of methanol and 1.78 ml of water is stirred with 381 mg of sodium periodate for 5 hours at room temperature. Then, it is added to water, extracted three times with dichloromethane, washed neutral, dried on sodium sulfate and concentrated by evaporation in a vacuum. 985 mg of crude product, which is chromatographed on silica gel with dichloromethane/methanol, is obtained. 514.3 mg of pure 14,17-ethano-7α-{5-[N-methyl-N-3-(4,4,5,5,5-pentafluoropentanesulfinyl)-propylamino]-pentyl}-estra-1,3,5(10)-triene-3,17β-diol is obtained as crystals with a melting point of 84–86° C.; $[\alpha]_D^{22}$=+13.0° (c=0.5% in chloroform).

EXAMPLE 3

3,17β-Diacetoxy-14α,17α-ethano-7α-{5-[N-methyl-N-3-(4,4,5,5,5-pentafluoropentylthio)-propylamino]-pentyl}-estra-1,3,5(10)-triene A solution of 600 mg of 14α,17α-ethano-7α-{5-[N-methyl-N-3-(4,4,5,5,5-pentafluoropentylthio)-propylamino]-pentyl}-estra-1,3,5(10)-triene-3,17β-diol in 2 ml of pyridine and 1 ml of acetic anhydride is stirred with 5 mg of dimethylaminopyridine for 4.5 hours at room temperature. Then, it is diluted with ethyl acetate, washed with water and common salt solution, dried on sodium sulfate and concentrated by evaporation in a vacuum. 680 mg of 3,17β-diacetoxy-14α,17α-ethano-7α-{5-[N-methyl-N-3-(4,4,5,5,5-pentafluoropentylthio)-propylamino]-pentyl}-estra-1,3,5(10)-triene is obtained as oil.

EXAMPLE 4

14,17-Ethano-7α-{5[N-methyl-N-3-(4,4,5,5,5-pentafluoropentanesulfonyl)-propylamino]-pentyl}-estra-1,3,5(10)-triene3,17β-diol A solution of 650 mg of 3,17β-diacetoxy-14α,17α-ethano-7α-{5-[N-methyl-N-3-(4,4,5,5,5-pentafluoropentylthio)-propylamino]-pentyl}-estra-1,3,5(10)-triene-in 15 ml of glacial acetic acid is stirred with 1.5 g of sodium perborate tetrahydrate for 3 hours at room temperature. Then, it is added to water, extracted three times with dichloromethane, washed neutral, dried on sodium sulfate, concentrated by evaporation in a vacuum, taken up in 10 ml of 0.2-molar methanolic potassium hydroxide solution, stirred for 24 hours at room temperature, added to water, extracted three times with dichloromethane, washed neutral, dried on sodium sulfate, concentrated by evaporation in a vacuum, suspended in 20 ml of ethyl acetate, mixed with 10 ml of tin(II) chloride solution, stirred for 4 hours at room temperature, diluted with ethyl acetate, washed with common salt solution, dried on sodium sulfate, concentrated by evaporation in a vacuum and chromatographed on silica gel with hexane/ethyl acetate. 300 mg of pure 14,17-ethano-7α-{5-[N-methyl-N-3-(4,4,5,5,5-pentafluoropentanesulfonyl)-propylamino]-pentyl}-estra-1,3,5(10)-triene-3,17β-diol is obtained as crystals with a melting point of 55–58° C.; $[\alpha]_D^{22}$+19.4° (c=0.51% in chloroform).

EXAMPLE 5

17α-Trifluoromethyl-7α-{5-[N-methyl-N-3-(4,4,5,5,5-pentafluoropentylthio)-propylamino]-pentyl}-estra-1,3,5(10)-triene-3,17β-diol a) 17β-Acetoxy-7α-(5-tert-butyl-dimethylsilyloxypentyl)-estr-4-en-3-one In 200 ml of absolute THF, 22.9 g of Mg chips with 261 g of 1-bromo-5-tert-butyldimethylsilyloxypentane [Tetrahedron Letters 23, 1982, 40, 4147–4150], dissolved in 250 ml of absolute THF is reacted to form the Grignard reagent. 92.9 g of copper(I) iodide is added to this solution, cooled to −20° C. under a nitrogen stream, and then 73.5 g of 17β-acetoxyestra-4,6-dien-3-one [J. Am. Chem. Soc. 80, 1958, 2596–2597], dissolved in 300 ml of absolute THF, is added in drops within one hour. For working-up, 61.2 ml of acetic acid is added in drops, the reaction mixture is diluted with ethyl acetate, washed with saturated ammonium chloride solution, water and sodium bicarbonate solution and dried. The residue that is obtained after the concentration by evaporation is chromatographed on silica gel. 48 g of 17β-acetoxy-7α-(5-tert-butyl-dimethylsilyloxypentyl)-estr-4-en-3-one is obtained.

b) 17β-Acetoxy-7α-(5-hydroxypentyl)-estr-4-en-3-one

A solution of 48 g of 17nβ-acetoxy-7α-(5-tert-butyl-dimethylsilyloxypentyl)-estr-4-en-3-one in 350 ml of methanol is allowed to stand with 35 ml of 8 vol % sulfuric acid for 30 minutes at room temperature. The solution is diluted with diethyl ether, washed neutral with water, and dried. After the concentration by evaporation, 37.7 g of 17β-acetoxy-7α-(5-hydroxypentyl)-estr-4-en-3-one is obtained as oil.

c) 17β-Acetoxy-7α-(5-acetoxypentyl)-estr-4-en-3-one

A solution of 37.7 g of 17β-acetoxy-7α-(5-hydroxypentyl)-estr-4-en-3-one in 160 ml of pyridine is slowly mixed with 80 ml of acetic anhydride and stirred for 16 hours at 25° C. Then, it is diluted with ethyl acetate, and the organic phase, after washing with sodium bicarbonate solution, is dried and concentrated by evaporation. The residue is chromatographed on silica gel, and 26.6 g of 17β-acetoxy-7α-(5-acetoxypentyl)-estr-4-en-3-one is obtained as oil. $[\alpha]_D^{22}$=+20.0° (c=0.51% in chloroform)

d) 17 β-Acetoxy-7α-(5-acetoxypentyl)-estra-1,3,5(10)-trien-3-ol

A solution of 5.18 g of lithium bromide and 26.73 g of copper(II) bromide in 260 ml of acetonitrile is added in drops to a solution, heated to 80° C., of 26.6 g of 17β-acetoxy-7α-(5-acetoxypentyl)-estr-4-en-3-one in 260 ml of acetonitrile within 30 minutes while being stirred. After the addition is completed, the reaction solution is cooled, diluted with diethyl ether, washed with water and sodium bicarbonate solution and dried. The residue that is obtained after the concentration by evaporation is chromatographed on silica gel, and 21.3 g of 17β-acetoxy-7α-(5-acetoxypentyl)-1,3,5(10)-estratrien-3-ol is obtained as oil. $[\alpha]_D^{22}$=+28.9° (c=0.535% in chloroform)

e) 17β-Acetoxy-7α-(5-acetoxypentyl)-3-(tetrahydropyran-2-yloxy)-estra-1,3,5(10)-triene A solution of 21.3 g of 17β-acetoxy-7α-(5-acetoxypentyl)-estra-1,3,5(10)-trien-3-ol in 213 ml of tetrahydrofuran is allowed to stand with 21.3 ml of 3,4-dihydro-2H-pyran and 1.065 g of p-toluenesulfonic acid for 8 hours at room temperature. The reaction solution is mixed with 3 ml of pyridine, then diluted with diethyl ether, washed with water and dried. The residue that is obtained after the concentration by evaporation is chromatographed on silica gel, and 24.3 g of 17β-acetoxy-7α-(5-acetoxypentyl)-3-(tetrahydropyran-2-yloxy)-estra-1,3,5(10)-triene is obtained as oil. $[\alpha]_D^{22}$=+31.5° (c=0.535% in chloroform)

f) 17β-Acetoxy-7α-(5-hydroxypentyl)-3-(tetrahydropyran-2-yloxy)-estra-1,3,5(10)-triene A solution of 10.2 g of 17β-acetoxy-7α-(5-acetoxypentyl)-3-(tetrahydropyran-2-yloxy)-estra-1,3,5(10)-triene in 205 ml of methanol is stirred with 33.7 ml of sodium hydroxide solution for 45 minutes at 15° C. Then, it is diluted with diethyl ether, washed with water, dried on sodium sulfate and concentrated by evaporation in a vacuum. 5.6 g of 17β-acetoxy-7α-(5-hydroxypentyl)-3-(tetrahydropyran-2-yloxy)-estra-1,3,5(10)-triene is obtained. $[\alpha]_D^{22}$=+32.2° (c=0.505% in chloroform)

g) 17β-Acetoxy-3-(tetrahydropyran-2-yloxy)-7α-(5-p-toluenesulfonyloxypentyl)-estra-1,3,5(10)-triene A solution of 5.5 g of 17β-acetoxy-7α-(5-hydroxypentyl)-3-(tetrahydropyran-2-yloxy)-estra-1,3,5(10)-triene in 47 ml of pyridine is allowed to stand with 5.5 g of p-toluenesulfonic anhydride for 45 minutes at room temperature. Then, the reaction solution is cooled in an ice bath, mixed with 4 ml of water and stirred for 45 more minutes. It is then diluted with ethyl acetate, washed with water, dried and concentrated by evaporation. 8.2 g of 17β-acetoxy-3-(tetrahydropyran-2-yloxy)-7α-(5-p-toluenesulfonyloxypentyl)-estra-1,3,5(10)-triene is obtained as oil.

h) 17β-Acetoxy-7α-(5-methylaminopentyl)-3-(tetrahydropyran-2-yloxy)-estra-1,3,5(10)-triene 6.3 g of methylamine is condensed in a pressure pipe while being cooled with ice in a solution of 8.2 g of 17β-acetoxy-3-(tetrahydropyran-2-yloxy)-7α-(5-p-toluenesulfonyloxypentyl)-estra-1,3,5(10)-triene in 80 ml of tetrahydrofuran. The closed pressure pipe is then heated for 6 hours to 60° C. After cooling, it is evaporated to dryness in a vacuum, and the residue is chromatographed on silica gel. 5.1 g of 17β-acetoxy-7α-(5-methylanininopentyl)-3-(tetrahydropyran-2-yloxy)-estra-1,3,5(10)-triene is obtained as oil. $[\alpha]_D^{22}$=+29.7° (c=0.535% in chloroform)

i) 17β-Acetoxy-7α-{5-[N-methyl-N-3-(4,4,5,5,5-pentafluoropentyl-thio)-propylamino]-pentyl}-3-(tetrahydropyran-2-yloxy)-estra-1,3,5(10)-triene A solution of 1.64 g of 17β-acetoxy-7α-(5-methylaminopentyl)-3-(tetrahydropyran-2-yloxy)-estra-1,3,5(10)-triene in 25 ml of absolute DMF is stirred with 159 mg of 80% sodium hydride under nitrogen for 2 hours at room temperature. 1.43 g of 3-chloropropyl-4,4,5,5,5-pentafluoropentylsulfide in 7 ml of absolute DnMnF is then added in drops and then stirred for 22 more hours at 80° C. The reaction solution is then diluted with ethyl acetate, washed with water, dried, concentrated by evaporation, and the residue is chromatographed on silica gel. 820 mg of 17β-acetoxy-7α-{5-[N-methyl-N-3-(4,4,5,5,5-pentafluoropentylthio)-propylamino]-pentyl}-3-(tetrahydropyran-2-yloxy-estra-1,3,5(10)-triene is obtained as oil.

$[\alpha]_D^{22}$=+21.5° (c=0.51% in chloroform)

j) 7α-{[N-Methyl-N-3(4,4,5,5,5-pentafluoro-pentylthio)-propylamino]-pentyl}-3-(tetrahydropyran-2-yloxy)-estra-1,3,5(10)-trien-17β-ol A solution of 790 mg of 17β-acetoxy-7α-(5-[N-methyl-N-3-(4,4,5,5,5-pentafluoro-pentylthio)-propylamino]-pentyl}-3-(tetrahydropyran-2-yloxy)-estra-1,3,5(10)-triene in 8 ml of methanol and 3 ml of THF is stirred with 430 mg of potassium carbonate for 18 hours at room temperature. The reaction solution is diluted with diethyl ether, washed with water, dried and concentrated by evaporation. 750 mg of crude 7α-{5-N-methyl-N-3-(4,4,5,5,5-pentafluoropentylthio)-propylamino]-pentyl }-3-(tetrahydropyran-2-yloxy)-estra-1,3,5(10)-trien-17β-ol is obtained.

k) 7α-{5-[N-Methyl-N-3-(4,4,5,5,5-pentafluoro-pentylthio)-propylamino]-pentyl}-estra-1,3,5(10)-triene-3,17β-diol A solution of 750 mg of 7α-{5-[N-methyl-N-3-(4,4,5,5,5-pentafluoro-pentylthio)-propylamino]-pentyl}-3-(tetrahydropyran-2-yloxy)-estra-1,3,5(10)-trien-17β-ol in 28 ml of methanol and 2.8 ml of water is stirred with 350 mg of oxalic acid for 17 hours at room temperature. It is then diluted with ethyl acetate, washed with sodium bicarbonate solution and water, dried and concentrated by evaporation. The residue is chromatographed on silica gel, and 640 mg of 7α-{5-[N-methyl-N-3-(4,4,5,5,5-pentafluoro-pentylthio)-propylamino]-pentyl}-estra-1,3,5(10)-triene-3,17β-diol is obtained as oil. $[\alpha]_D^{22}$=+24.0° (c=0.515% in chloroform)

l) 7α-{5-[N-Methyl-N-3-(4,4,5,5,5-pentafluoro-pentylthio)-propylamino]-pentyl}-3-(tetrahydropyran-2-yloxy)-estra-1,3,5(10)-trien-17-one A solution of 900 mg of 7α-{5-[N-methyl-N-3-(4,4,5,5,5-pentafluoro-pentylthio)-propylamino]-pentyl}-3-(tetrahydropyran-2-yloxy)-estra-1,3,5(10)-trien-17β-ol is mixed in 30 ml of toluene and 9.6 ml of cyclohexanone with a solution of 900 mg of aluminum isopropylate in 16 ml of toluene and heated for 30 minutes while being distilled off slowly. The reaction solution is then diluted with ethyl acetate, washed with 20% potassium sodium tartrate solution, dried and concentrated by evaporation. The residue is chroma)tographed on silica gel with hexane/ethyl acetate. 715 mg of 7α-{5-[N-methyl-N- 3-(4,4,5,5,5-pentafluoro-pentylthio)-propylamino]-pentyl}-3-(tetrahydropyran-2-yloxy)-estra-1,3,5(10)-trien-17-one is obtained as oil.

m) 17α-Trifluoromethyl-3-(tetrahydropyran-2-yloxy)-7α-{5-[N-methyl-N-3-(4,4,5,5,5-pentafluoropentylthio)-propylamino]-pentyl}-estra-1,3,5(10)-trien-17β-ol A solution of 500 mg of 7α-{5-[N-methyl-N-3-(4,4,5,5,5-pentafluoropentylthio)-propylamino]-pentyl}-3-(tetrahydropyran-2-yloxy)-estra-1,3,5(10)-trien-17-one (see Ausw.-Pat Example 2a) in 5 ml of absolute tetrahydrofuran is mixed at a bath temperature of 0° C. with 0.27 ml of (trifluoromethyl)-trimethylsilane. Then, 0.2 ml of a 1.1-molar tetrabutylammonium fluoride solution is slowly added in drops and stirred for 45 minutes, again 1 ml of 1.1-molar tetrabutylammonium fluoride solution is added, and it is stirred for another 30 minutes. Then, it is diluted with ethyl acetate, washed with water, dried on sodium sulfate, concentrated by evaporation in a vacuum and chromatographed on silica gel with dichloromethane/methanol. 285 mg of 17α-trifluoromethyl-3-(tetrahydropyran-2-yloxy)-7α-{5-[N-methyl-N-3-(4,4,5,5,5-pentafluoropentylthio)-propylamino]-pentyl}-estra-1,3,5(10)-trien-17β-ol is obtained as oil.

n) 17α-Trifluoromethyl-7α-{5-[N-methyl-N-3-(4,4,5,5,5-pentafluoropentylthio)-propylamino]-pentyl}-estra-1,3,5(10)-triene-3,17β-diol A solution of 280 mg of 17α-trifluoromethyl-3-(tetrahydropyran-2-yloxy)-7α-{5-[N-methyl-N-3-(4,4,5,5,5-pentafluoropentylthio)-propylamino]-pentyl}-estra-1,3,5(10)-trien-17β-ol in 5.6 ml of methanol and 0.56 ml of water is stirred with 140 mg of oxalic acid for 18 hours at room temperature. Then, it is diluted with ethyl acetate, washed with sodium bicarbonate and water, dried on sodium sulfate, concentrated by evaporation in a vacuum and chromatographed on silica gel with dichloromethanetmethanol. 215 mg of 17α-trifluoromethyl-7α-{5-[N-methyl-N-3-(4,4,5,5,5-pentafluoropentylthio)-propylamino]-pentyl}-estra-1,3,5(10)-triene-3,17β-diol is obtained as oil.

EXAMPLE 6

15β,16β-Methano-17α-methyl-7α-{5-[N-methyl-N-3-(4,4,5,5,5-pentafluoropentylthio)-propylamino]-pentyl}-estra-1,3,5(10)-triene-3,17β-diol a) 3-Benzyloxy-17,17-ethylenedioxy-7α-(5-hydroxypentyl)-estra-1,3,5(10),15-tetraene A solution of 32.7 g of 17,17-ethylenedioxy-7α-(5-hydroxypentyl)-estra-1,3,5(10),15-tetraen-3-ol (see Example 1h) in 327 ml of dimethylformamide is mixed at room temperature with 5.73 g of lithium hydroxide and stirred with 15.1 ml of benzyl bromide for 2 hours at 60° C. Then, it is diluted with ethyl acetate, washed with water, dried on sodium sulfate, concentrated by evaporation in a vacuum and chromatographed on silica gel with dichloromethanenimethanol. 32.8 g of 3-benzyloxy-17,17-ethylenedioxy-7α-(5-hydroxypentyl)-estra-1,3,5(10),15-tetraene is obtained.

b) 3-Benzyloxy-7α-(5-hydroxypentyl)-estra-1,3,5(10),15-tetraen-17-one

A solution of 32.8 g of 3-benzyloxy-17,17-ethylenedioxy-7α-(5-hydroxypentyl)-estra-1,3,5(10),15-tetraene in 328 ml of acetone and 32.8 ml of water is stirred at room temperature with 1.033 g of para-toluenesulfonic acid for 2 hours. Then, it is diluted with diethyl ether, washed with sodium bicarbonate and water, dried on sodium sulfate, concentrated by evaporation in a vacuum and chromatographed on silica gel with dichloromethane acetone. 25.4 g of 3-benzyloxy-7α-(5-hydroxypentyl)-estra-1,3,5(10),15-tetra-en-17-one is obtained.

c) 3-Benzyloxy-7α-(5-hydroxypentyl)-15β,16β-methanol-estra-1,3,5(10),15-tetraen-17-one 2.861 g of trimethylsulfoxonium iodide with 345 mg of 80% sodium hydride is reacted in 65 ml of dimethylsulfoxide over a period of 2 hours at room temperature. 4.44 g of 3-benzyloxy-7α-(5-hydroxypentyl)-estra-1,3,5(10),15-tetraene-17-one is added to this solution, and it is stirred for 45 minutes at room temperature. The settled precipitate is filtered off, and it is washed with water. This precipitate is taken up with ethyl acetate, washed with water, dried on sodium sulfate, concentrated by evaporation in a vacuum and chromatographed on silica gel with hexane/acetone. 2.8 g of 3-benzyloxy-7α-( 5-hydroxypentyl)-15β,16β-methanol-estra-1,3,5(10),15-tetraen-17-one is obtained. $[\alpha]_D^{22}=+13.1°$ (c=0.525% in chloroform).

d) 3-Benzyloxy-15β,16β-methano-7α-(5-tosylonxypentyl)-estra-1,3,5(10),15-tetraen-17-one A solution of 2.5 g of 3-benzyloxy-7α-(5-hydroxypentyl)-15β,16β-methano-estra-1,3,5(10),15-tetraen-17-one in 25 ml of pyridine is mixed at room temperature with 2.5 g of para-toluenesulfonic anhydride and allowed to stand for 30 minutes, mixed with 1 ml of water while being cooled with ice and allowed to stand for another 45 minutes. Then, it is diluted with diethyl ether, washed with water, dried on sodium sulfate and concentrated by evaporation in a vacuum. 3.4 g of crude 3-benzyloxy-15β,16β-methano-7α-(5-tosyloxypentyl)-estra-1,3,5(10),15-tetraen-17-one is obtained.

e) 3-Benzyloxy-15β,16β-methano-7α-{5-[N-methyl-N-3-(4,4,5,5,5-pentafluoropentylthio)-propylamino]-pentyl}-estra-1,3,5(10),15-tetraen-17-one A solution of 2.1 g of methyl-[3-(4,4,5,5,5-pentafluoropentylthio)-propyl]-amine in 1 ml of dimethylformamide is added to a solution of 3.4 g of crude 3-benzyloxy-15β,16β-methano-7α-(5-tosyloxypentyl)-estra-1,3,5(10),15-tetraen-17-one in 34 ml of dimethylformamide, and it is stirred for 3.5 hours at 100° C. Then, it is diluted with ethyl acetate, washed with water, dried on sodium sulfate, concentrated by evaporation in a vacuum and chromatographed on silica gel with dichloromethane/methanol. 2.6 g of 3-benzyloxy-15β,16β-methano-7α-{5-[N-methyl-N-3-(4,4,5,5,5-pentafluoropentylthio)-propylamino]-pentyl]-estra-1,3,5(10),15-tetraen-17-one is obtained as oil.

f) 15β,16β-Methano-7α-{5-[N-methyl-N-3-(4,4,5,5,5-pentafluoro-pentylthio)-propylamino]-pentyl}-3-hydroxy-estra-1,3,5(10),15-tetraen-17-one A solution of 2.3 g of 3-benzyloxy-15β,16β-methano-7α-{5-[N-methyl-N-3-(4,4,5,5,5-pentafluoro-pentylthio)-propylamino]-pentyl}-estra-1,3,5(10),15-tetraen-17-one in 53 ml of dichloromethane is stirred at a bath temperature of 0° C. with 1.12 ml of N,N-dimethylaniline and 1.64 g of aluminum chloride (anhydrous) for 4.5 hours. Then, it is diluted with ethyl acetate, washed with 30% potassium-sodium tartrate solution and water, dried on sodium sulfate, concentrated by evaporation in a vacuum and chromatographed on silica gel with dichloromethane/methanol. 1.52 g of 15β,16β-methano-7α-{5-[N-methyl-N-3-(4,4,5,5,5-pentafluoro-pentylthio)-propylamino]-pentyl}-3-hydroxy-estra-1,3,5(10),15-tetraen-17-one is obtained as oil. $[\alpha]_D^{22}=-2.5°$ (c=0.505% in chloroform).

g) 15β,16β-Methano-17α-methyl-7α-{5-[N-methyl-N-3-(4,4,5,5,5-pentafluoropentylthio)-propylamino]-pentyl}-estra-1,3,5(10)-triene-3,17β-diol 1.8 ml of a 3-molar methylmagnesium bromide solution is added in drops to a solution of 515 mg of 15β,16β-methano-7α-{5-[N-methyl-N-3-(4,4,5,5,5-pentafluoropentylthio)-propylamino]-pentyl}-3-hydroxy-estra-1,3,5(10),15-tetraen-1-one in 10 ml of tetrahydrofnuiran at 0° C., and it is stirred for 2 hours at room temperature. Then, it is diluted with ethyl acetate, washed with saturated ammonium chloride solution and water, dried on sodium sulfate, concentrated by evaporation in a vacuum and chromatographed on silica gel with dichloromethanemethanol. 395 mg of 15β,16β-methano-17α-methyl-7α-{5-[N-methyl-N-3-(4,4,5,5,5-pentafluoro-pentylthio)-propylamino]-pentyl}-estra-1,3,5(10)-triene-3,17β-diol is obtained as oil. $[\alpha]_D^{22}=-5.1°$ (c=0.52% in chloroform)

EXAMPLE 7

15β,16β-Methano-17α-methyl-7α-{5-[N-methyl-N-3-(4,4,5,5,5-pentafluoropentanesulfinyl)-propylamino]-pentyl}-estra-1,3,5(10)-triene-3,17βdiol A solution of 115 mg of 15β,16β-methano-17α-methyl-7α-{5-[N-methyl-N-3-(4,4,5,5,5-pentafluoro-pentylthio)-propylamino]-pentyl}-estra-1,3,5(10)-triene-3,17β-diol (see Example 6) in 5 ml of methanol is stirred with 80 mg of sodium periodate for 3 hours at room temperature. Then, it is diluted with ethyl acetate, washed with water, dried on sodium sulfate, concentrated by evaporation in a vacuum and chromatographed on silica gel with dichloromethanelmethanol. 65 mg of 15β,16β-methano-17α-methyl-7α-{5-[N-methyl-N-3-(4,4,5,5,5-pentafluoro-pentanesulfinyl)-propylanino]-pentyl}-estra-1,3,5(10)-triene-3,17β-diol is obtained as oil. $[\alpha]_D^{22}=-13.3°$ (c=0.27% in chloroform)

EXAMPLE 8

15β,16β-Methano-7α-{5-[N-methyl-N-3-(4,4,5,5,5-pentafluoropentylthio)-propylamino]-pentyl}-estra-1,3,5(10)-triene-3,17β-diol A solution of 500 mg of 15β,16β-methanol-7α-{5-[N-methyl-N-3-(4,4,5,5,5-pentafluoro-pentylthio)- propylamino]-pentyl}-3-hydroxy-estra-1,3,5(10),15-tetraen-17-one (see Example 6f) in 10 ml of methanol and 1 ml of water is stirred with 100 mg of sodium borohydride for 3 hours at room temperature. Then, it is diluted with ethyl acetate, washed with water, dried on sodium sulfate, concentrated by evaporation in a vacuum and chromatographed on silica gel with dichloromethane/methanol. 340 mg of 15β,16β-methano-7α-{5-[N-methyl-N-3-(4,4,5,5,5-pentafluoro-pentylthio)-propylamino]-pentyl}-estra-1,3,5 (10)-triene-3,17β-diol is obtained as oil. $[\alpha]_D^{22}=+11.9°$ (c=0.52% in chloroform)

EXAMPLE 9

15β,16β-Methano-7α-{5-[N-methyl-N-3-(4,4,5,5,5-pentafluoropentanesulfinyl)-propylamino]-pentyl}-estra-1,3,5(10)-triene-3,17β-diol A solution of 100 mg of 15β,16β-methano-7α-{5-[N-methyl-N-3-(4,4,5,5,5-pentafluoro-pentylthio)-propylamino]-pentyl}-estra-1,3,5(10)-triene-3,17β-diol (see Example 8) in 5 ml of methanol is stirred with 80 mg of sodium periodate for 3 hours at room temperature. Then, it is diluted with ethyl acetate, washed with water, dried on sodium sulfate, concentrated by evaporation in a vacuum and chromatographed on silica gel with dichloromethane/methanol. 70 mg of 15β,16β-methanol-7α-{5-[N-methyl-N-3-(4,4,5,5,5-pentafluoro-pentanesulfinyl)-propylamino]-pentyl}-estra-1,3,5(10)-triene-3,17β-diol is obtained as oil. $[\alpha]_D^{22}=+12.2°$ (c=0.515%) in chloroform).

EXAMPLE 10

15β-Methyl-7α-{5[N-methyl-N-3-(4,4,5,5,5-pentafluoropentylthio)-propylamino]-pentyl}-estra-1,3,5(10)-trienne3,17β-diol a) 3-Benzyloxy-7α-(5-hydroxypentyl)-15β-methyl-estra-1,3,5(10)-trien-17-one 5.35 g of copper(I) iodide is added to an ice-cooled solution of 11.9 ml of a 3-molar methylmagnesium bromide solution in 68 ml of tetrahydrofuran under a nitrogen stream. Then, a solution of 4.26 g of 3-benzyloxy-7α-(5-hydroxypentyl)-estra-1,3,5(10),15-tetraen-17-one (see Example 6b) in 50 ml of tetrahydrofuran is added in drops and stirred for 30 minutes at a bath temperature of 0° C. Then, the excess reagent is decomposed with saturated ammonium chloride solution, diluted with ethyl acetate, washed with ammonium chloride solution and water, dried on sodium sulfate, concentrated by evaporation in a vacuum and chromatographed on silica gel with hexane/acetone. 3.6 g of 3-benzyloxy-7α-(5-hydroxypentyl)-15β-methyl-estra-1,3,5(10)-trien-17-one is obtained as oil. $[\alpha]_D^{22}=+66.4°$ (c=0.515% in chloroform).

b) 3-Benzyloxy-15β-methyl-7α-(5-tosyloxypentyl)-estra-1,3,5(10)-trien-17-one

A solution of 3.6 g of 3-benzyloxy-7α-(5-hydroxypentyl)-15β-methyl-estra-1,3,5(10)-trien-17-one is tosylated as described in Example 6d. 4.9 g of crude 3-benzyloxy-15β-methyl-7α-(5-tosyloxypentyl)-estra-1,3,5(10)-trien-17-one is obtained.

c) 3-Benzyloxy-15β-methyl-7α-(5-N-methylaminopentyl)-estra-1,3,5(10)-trien-17-one 3.8 g of methylamine is condensed in a solution of 4.9 g of 3-benzyloxy-15β-methyl-7α-(5-tosyloxypentyl)-estra-1,3,5(10)-trien-17-one in 30 ml of tetrahydrofuran in a pressurized reactor while being cooled, the closed reactor is heated for 5.5 hours to 80° C., cooled and opened. Then, it is diluted with ethyl acetate, washed with water, dried on sodium sulfate, concentrated by evaporation in a vacuum and chromatographed on silica gel with dichloromethane/methanol/1% triethylamine. 3.15 g of 3-benzyloxy-15β-methyl-7α-(5-N-methylaminopentyl)-estra-1,3,5(10)-trien-17-one is obtained as oil.

d) 3-Benzyloxy-15β-methyl-7α-{5-[N-methyl-N-3-(4,4,5,5,5-pentafluoro-pentylthio)-propylamino]-pentyl}-estra-1,3,5(10)-trien-17-one A solution of 3.15 g of 3-benzyloxy-15β-methyl-7α-(5-N-methylaminopentyl)-estra-1,3,5(10)-trien-17-one in 31.5 ml of absolute dimethylformamide is mixed with 228 mg of 80% sodium hydride and stirred for 5 hours at room temperature, mixed with 2.6 g of 3-chloropropyl4,4,5,5,5-pentafluoropentylsulfide in 2 ml of absolute dimethylformamide and stirred for 24 hours at 80° C. Then, it is diluted with ethyl acetate, washed with sodium bicarbonate and water, dried on sodium sulfate, concentrated by evaporation in a vacuum and chromatographed on silica gel with dichloromethane/methanol. 3.1 g of 3-benzyloxy-15β-methyl-7α-{5-[N-methyl-N-3-(4,4,5,5,5-pentafluoro-pentylthio)-propylamino]-pentyl}-estra-1,3,5(10),15-trien-17-one is obtained as oil.

e) 3-Hydroxy-15β-methyl-7α-{5-[N-methyl-N-3-(4,4,5,5,5-pentafluoro-pentylthio)-propylamino]-pentyl}-estra-1,3,5 (10)-trien-17-one A solution of 3.1 g of 3-benzyloxy-15β-methyl-7α-{5-[N-methyl-N-3-(4,4,5,5,5-pentafluoro-pentylthio)-propylamino]-pentyl}-estra-1,3,5(10)-trien-17-one is debenzylated as described in example 6f. 830 mg of 3-hydroxy-15β-methyl-7α-{5-[N-methyl-N-3-(4,4,5,5,5-pentafluoro-pentylthio)-propylamino]-pentyl}-estra-1,3,5 (10)-trien-17-one is obtained as oil.

f) 15β-Methyl-7α-{5-[N-methyl-N-3-(4,4,5,5,5-pentafluoro-pentylthio)-propylamino]-pentyl}-estra-1,3,5 (10)-triene-3,17β-diol A solution of 460 mg of 3-hydroxy-15β-methyl-7α-{5-[N-methyl-N-3-(4,4,5,5,5-pentafluoro-pentylthio)-propylamino]-pentyl}-estra-1,3,5(10)-trien-17-one is reduced as described in Example 8. 200 mg of 15β-methyl-7α-{5-[N-methyl-N-3-(4,4,5,5,5-pentafluoro-pentylthio)-propylamino]-pentyl}-estra-1,3,5(10)-triene-3,17β-diol is obtained as oil. $[\alpha]_D^{22}=+4.5°$ (c=0.51% in chloroform)

EXAMPLE 11

15β,17α-Dimethyl-7α-{5-[N-methyl-N-3-(4,4,5,5,5-pentafluoro-pentylthio)-propylamino]-pentyl}-estra-1,3,5(10)-triene-3,17β-diol 1.44 g of dried cerium(III) chloride is stirred for 2 hours at room temperature in 15 ml of tetrahydrofuran, mixed with 3.75 ml of a 3-molar methylmagnesium bromide solution while being cooled with ice, stirred for 15 minutes while being cooled and for 30 minutes at room temperature, a solution of 650 mg of 3-hydroxy-15β-methyl-7α-{5-[N-methyl-N-3-(4,4,5,5,5-pentafluoro-pentylthio)-propylamino]-pentyl}-estra-1,3,5(10)-trien-17-one (see Example 10e) in 7 ml of tetrahydrofuran is added in drops, stirred for 2 hours at room temperature, and excess reagent is decomposed with saturated ammonium chloride solution. Then, it is diluted with ethyl acetate, washed with saturated ammonium chloride solution and water, dried on sodium sulfate, concentrated by evaporation in a vacuum and chromatographed on silica gel with dichloromethane/methanol. 145 mg of 15β,17α-dimethyl-7α-{5-[N-methyl-N-3-(4,4,5,5,5-pentafluoropentylthio)-propylamino]-pentyl}-estra-1,3,5(10)-triene-3,17β-diol is obtained as oil. $[\alpha]_D^{22}=-7.3°$ (c=0.505% in chloroform).

EXAMPLE 12

11β-Fluoro-7α-{5-[N-methyl-N-3-(4,4,5,5,5-pentafluoropentylthio)-propylamino]-pentyl}-estra-1,3,5(10)-triene-3,17β-diol a) 11β-Fluoro-estr-4-ene-3,17-dione 4.6 ml of perfluorobutane-1-sulfonic acid fluoride is added in drops to 5.0 g of 11α-hydroxy-estr-4-ene-3,17-dione in 100 ml of toluene and 7.3 ml of 1,8-diazabicyclo [5,4,0]undec-7-ene at 0° C. After 30 minutes, the solution is diluted with ethyl acetate, washed with saturated sodium chloride solution, dried and concentrated by evaporation in a vacuum. After the crude product is chromatographed on silica gel with a hexane-ethyl acetate gradient, 3.8 g of 11β-fluoro-estr-4-ene-3,17-dione with a melting point of 173–174° C. is obtained.

b) 11β-Fluoro-3-methoxy-estra-3,5-dien-17-one 7.8 g of 11β-fluoro-estr-4-ene-3,17-dione is stirred in 40 ml of 2,2-dimethoxypropane with 780 mg of pyridinium-toluene-4-sulfonate for 5 hours at 80° C. Then, 1.5 ml of triethylamine is added, it is diluted with ethyl acetate and washed with saturated sodium chloride solution. After crystallization from methanol, 5.3 g of 11β-fluoro-3-methoxy-estra-3,5-dien-17-one with a melting point of 173° C. is obtained.

c) 11β-Fluoro-estra-4,6-diene-3,17-dione 5 ml of a 10% sodium acetate solution and, in portions, 2.5 g of 1,3-dibromo-5,5-dimethylhydantoin are added in succession to 5.0 g of 11β-fluoro-3-methoxy-estra-3,5-dien-17-one in 50 ml of DMF at 0° C. After 30 minutes, 2.3 g of sodium sulfite is added and then 2.5 g of lithium bromide and 2.0 g of lithium carbonate, and it is stirred for 2 hours at 100° C. The reaction mixture is stirred into ice water. The precipitated product is suctioned off, dissolved in ethyl acetate, washed with water, dried and concentrated by evaporation in a vacuum. After recrystallization from ethyl acetate, 3.6 g of 11β-fluoro-estra-4,6-diene-3,17-dione with a melting point of 198° C. is obtained.

d) 11β-Fluoro-7α-(5-tert-butyl-dimethylsilyloxypentyl)-estr-4-ene-3,17-dione 7.9 g of magnesium in 40 ml of THF is reacted to form the Grignard reagent under nitrogen with a solution of 95.3 g of 1-bromo-5-tert-butyl-dimethylsilyloxypentane [Tetrahedron Letters 1982, 4147–4150] in 260 ml of THF. At −30° C., 32 g of copper(I) iodide is added, and then 29 g of 11β-fluoro-estra-4,6-diene-3,17-dione in 290 ml of THF is added in drops. After the reaction is completed, it is mixed with 20.4 ml of glacial acetic acid, and the reaction mixture is stirred into ice water. The precipitated product is suctioned off, dissolved in ethyl acetate, washed neutral with water and dried. After the crude product is chromatographed on silica gel with a hexane-ethyl acetate gradient, 23.9 g of 11β-fluoro-7α-(5-tert-butyl-dimethylsilyloxypentyl)-estr-4-ene-3,17-dione is obtained as foam.

e) 11β-Fluoro-7α-(5-hydroxypentyl)-estr-4-ene-3,17-dione

A solution of 23.1 g of 11β-fluoro-7α-{5-tert-butyl-dimethylsilyloxypentyl)-estr-4-ene-3,17-dione in 115 ml of THF and 64 ml of water are stirred with 128 ml of glacial acetic acid for 2.5 hours at 50° C. The reaction mixture is concentrated by evaporation in a vacuum, taken up in ethyl acetate, washed with water and dried. 20.4 g of 11β-fluoro-7α-(5-hydroxypentyl)-estr-4-ene-3,17-dione is obtained as foam.

f) 7α-(5-Acetoxypentyl)-11β-fluoro-estr-4-ene-3,17-dione 20 g of 11β-fluoro-7α-(5-hydroxypentyl)-estr4-ene-3,17-dione in 100 ml of pyridine can be reacted over a period of 2 hours with 50 ml of acetic anhydride at 25° C. Then, 5 ml of water is added at 0° C., and it is stirred for 45 minutes. It is extracted with diethyl ether, washed with 2N sulfnuiric acid, pyridine-free, and the solution is neutralized in succession with saturated sodium bicarbonate solution and water. After drying and concentration by evaporation in a vacuum, the crude product is chromatographed on silica gel with a hexane-ethyl acetate-gradient. 17 g of 7α-(5-acetoxypentyl)-11β-fluoro-estr-4-ene-3,17-dione with a melting point of 78.4° C. is obtained.

g) 7α-(5-Acetoxypentyl)-11β-fluoro-3-hydroxy-estra-1,3,5 (10)-trien-17-one 18.6 of copper(II) bromide and 3.6 g of lithium bromide are added to 16.5 g of 7α-(5-acetoxypentyl)-11β-fluoro-estr-4-ene-3,17-dione in 190 ml of acetonitrile at 80° C. After 15 minutes, the reaction mixture is stirred into sodium bicarbonate-containing ice water. The precipitated product is suctioned off, dissolved in ethyl acetate, washed with water, dried and concentrated by evaporation in a vacuum. After the crude product is chromatographed on silica gel with a hexane-ethyl acetate gradient, 8.5 g of 7α-(5-acetoxypentyl)-11β-fluoro-3-hydroxy-estra-1,3,5(10)-trien-17-one is obtained as foam.

h) 7α-(5-Acetoxypentyl)-11β-fluoro-3-(tetrahydropyran-2-yloxy)-estra-1,3,5(10)-trien-17-one 8.2 g of 7α-(5-acetoxypentyl)-11β-fluoro-3-hydroxy-estra-1,3,5(10)-trien-17-one in 86 ml of THF is stirred with 8.6 ml of 3,4-dihydro-2H-pyran and 820 mg of p-toluenesulfonic acid hydrate for 2.5 hours at room temperature. Then, 0.5 ml of triethylamine is added, it is diluted with ethyl acetate, washed with saturated sodium chloride solution, dried and concentrated by evaporation in a vacuum. After the crude product is chromatographed on silica gel with a hexane-ethyl acetate gradient, 7.8 g of 7α-(5-acetoxypentyl)-11β-fluoro-3-(tetrahydropyran-2-yloxy)-estra-1,3,5(10)-trien-17-one is obtained as foam.

i) 11β-Fluoro-7α-(5hydroxypentyl)-3-(tetrahydropyran-2-yloxy)-estra-1,3,5(10)-trien-17-one 7.4 g of 7α-(5-acetoxypentyl)-11β-fluoro-3-(tetrahydropyran-2-yloxy)-estra-1,3,5(10)-trien-17-one in 370 ml of methanol and 37 ml of water is stirred at room temperature with 1.8 g of potassium carbonate. After 3 hours, the reaction mixture is added to ice water. The precipitated product is suctioned off, dissolved in ethyl acetate, washed neutral with water, dried and concentrated by evaporation in a vacuum. 7.0 g of 11β-fluoro-7α-(5-hydroxypentyl)-3-(tetrahydropyran-2-yloxy)-estra-1,3,5 (10)-trien-17-one is obtained as foam.

j) 11β-Fluoro-3-(tetrahydropyran-2-yloxy)-7α-(5-p-toluenesulfonylolypentyl)-estra-1,3,5(10)-trien-17-one 6.7 g of 11β-fluoro-7α-(5-hydroxypentyl)-3-(tetrahydropyran-2-yloxy)-estra-1,3,5(10)-trien-17-one in 70 ml of pyridine is stirred at room temperature with 6.0 g of p-toluenesulfonic anhydride for 3 hours. The solution is diluted with ethyl acetate, washed with saturated sodium chloride solution, dried and concentrated by evaporation in a vacuum. The crude product is chromatographed on silica gel with a hexane-ethyl acetate gradient. 5.7 g of 11β-fluoro-3-(tetrahydropny-2-yloxy)-7α-(5-p-toluenesulfonyloxy-pentyl)-estra-1,3,5(10)-trien-17-one is obtained as foam.

k) 11β-Fluoro-7α-{5-[N-methyl-N-3-(4,4,5,5,5-pentafluoropentylthio)-propylamino]-pentyl}-3-(tetrahydrapyran-2-yloxy)-estra-1,3,5(10)-trien-17-one 2.0 g of 11β-fluoro-3-(tetrahydropyran-2-yloxy)-7α-(5-p-toluenesulfonyloxypentyl)-estra-1,3,5(10)-trien-17-one in 44 ml of DMF is stirred at 80° C. with 1.2 g of methyl-[3-(4,4,5,5,5-pentafluoropentyl-thio)-propyl]-amine. After 6.5 hours, the reaction mixture is mixed with water. It is extracted with ethyl acetate, washed with saturated sodium chloride solution and concentrated by evaporation in a vacuum. After the crude product is chromatographed on silica gel with a methylene chloride-methanol gradient, 1.3 g of 11β-fluoro-7α-{5-[N-methyl-N-3-(4,4,5,5,5-pentafluoropentylthio)-propylamino]-pentyl}-3-(tetrahydrapyran-2-yloxy)-estra-1,3,5(10)-trien-17-one is obtained as oil.

l) 11β-Fluoro-7α-{5-[N-methyl-N-3-(4,4,5,5,5-pentafluoropentylthio)-propylamino]-pentyl}-3-(tetrahydrapyran-2-yloxy)-estra-1,3,5(10)-trien-17β-ol 350 mg of sodium borohydride is added in portions to 2.0 g of 11β-fluoro-7α-{5-[N-methyl-N-3-(4,4,5,5,5-pentafluoro-penthylthio)-propylamino]pentyl}-3-(tetrahydrapyran-2-yloxy)-estra-1,3,5(10)-trien-17-one in 17 ml of THF, 10 ml of ethanol and 4.2 ml of water at 0° C. After 30 minutes, the reaction mixture is stirred into ice water, extracted with ethyl acetate, washed with saturated sodium chloride solution and concentrated by evaporation in a vacuum. 1.7 g of crude 11β-fluoro-7α-{5-[N-methyl-N-3-(4,4,5,5,5-pentafluoropentylthio)-propylamino]-pentyl}-3-(tetrahydrapyran-2-yloxy)-estra-1,3,5(10)-trien-17β-ol is obtained as foam.

m) 11β-Fluoro-7α-{5-[N-methyl-N-3-(4,4,5,5,5-pentafluoropentylthio)-propylamino]-pentyl}-estra-1,3,5(10)-triene-3,17β-diol A solution of 1.6 g of 11β-fluoro-7α-{5-[N-methyl-N-3-(4,4,5,5,5-pentafluoropentylthion)-propylamino]-pentyl}-3-(tetrahydrapyran-2-yloxy)-estra-1,3,5(10)-trien-17β-ol in 20 ml of methanol and 2 ml of water is stirred with 1.0 g of oxalic acid. After 3 hours, the reaction mixture is added to ice water. It is extracted with methylene chloride, washed with saturated sodium chloride solution, dried and concentrated by evaporation in a vacuum. After the crude product is chromatographed on silica gel with a methylene chloride-methanol gradient, 1.1 g of 11β-fluoro-7α-{5-[N-methyl-N-3-(4,4,5,5,5-pentafluoropentylthio)-propylamino]-pentyl}-estra-1,3,5(10)-triene-3,17β-diol with a melting point of 95n° C is obtained.

EXAMPLE 13

11β-Fluoro-7α-{5-[N-methyl-N-3-(4,4,5,5,5-pentafluoropentanesulfinyl)-propylaminon]-pentyl}-estra-1,3,5(10)-triene-3,17β-diol 580 mg of 11β-fluoro-7α-{5-[N-methyl-N-3-(4,4,5,5,5-pentafluoropentylthio)-propylamino]-pentyl}-estra-1,3,5(10)-triene-3,17β-diol in 24 ml of methanol and 1.1 ml of water are stirred at room temperature with 350 mg of sodium periodate. After 1.5 hours, it is diluted with methylene chloride, washed with saturated sodium chloride solution, dried and concentrated by evaporation in a vacuum. The crude product is chromatographed on silica gel with a methylene chloride-metlhanol gradient. 287 mg of 11β-fluoro-7α-{5-[N-methyl-N-3-(4,4,5,5,5-pentafluoropentanesulfinyl)-propylamino]-pentyl}-estra-1,3,5(10)-triene-3,17β-diol with a melting point of 87° C. is obtained.

EXAMPLE 14

11β-Fluoro-7α-{5-[N-methyl-N-3-(4,4,5,5,5-pentafluoropentanesulfonyl)-propylamino]-pentyl}-estra-1,3,5(10)-triene-3,17β-diol a) 11β-Fluoro-7α-{5-[N-methyl-N-3-(4,4,5,5,5-pentafluoropentanesulfonyl)-propylamino]-pentyl)-3-(tetrahydrapyran-2-yloxy)-estra-1,3,5(10)-trien-17-one 2.0 g of 11β-fluoro-3-tetrahydropyran-2-yloxy-7α-(5-p-toluenesulfonyloxypentyl)-estra-1,3,5(10)trien-17-one in 40 ml of DMF is stirred with 2.1 g of methyl-[3-(4,4,5,5,5-pentafluoro-pentanesulfonyl)-propyl]-amine at 80° C. After 7 hours, the reaction mixture is added to ice water, extracted with ethyl acetate, washed with saturated sodium chloride solution, dried and concentrated by evaporation in a vacuum. After the crude product is chromatographed on silica gel with a methylene chloride-methanol gradient, 1.1 g of 11β-fluoro-7α-{5-[N-methyl-N-3-(4,4,5,5,5-pentafluoropentanesulfonyl)-propylamino]-pentyl}-3-(tetrahydrapyran-2-yloxy)-estra-1,3,5(10)-trien-17-one is obtained as oil.

b) 11β-Fluoro-7α-{5-[N-methyl-N-3-(4,4,5,5,5-pentafluoropentanesulfonyl)-propylamino]-pentyl}-3-(tetrahydrapyran-2-yloxy)-estra-1,3,5(10)-trien-17β-ol 1.5 g of 11β-fluoro-7α-{5-[N-methyl-N-3-(4,4,5,5,5-pentafluoropentanesulfonyl)-propylamino]-pentyl}-3-(tetrahydrapyran-2-yloxy)-estra-1,3,5(10)-trien-17-one is mixed at 0° C. in a mixture of 13 ml of THF, 7.5 ml of ethanol and 3.2 ml of water in portions with 270 mg of sodium borohydride. After 90 minutes, water is added, extracted with ethyl acetate, washed with saturated sodium chloride solution, dried and concentrated by evaporation in a vacuum. 1.5 g of 11β-fluoro-7α-{5-[N-methyl-N-3-(4,4,5,5,5-pentafluoropentanesulfonyl)-propylamino]-pentyl)-3-(tetrahydrapyran-2-yloxy)-estra-1,3,5(10)-trien-17β-ol is obtained as crude product.

c) 11β-Fluoro-7α-{5[N-methyl-N-3-(4,4,5,5,5-pentafluoropentanesulnfonyl)-propyl-amino]-pentyl}-estra-1,3,5(10)-triene-3,17β-diol 1.4 g of 11β-fluoro-7α-{5-[N-methyl-N-3-(4,4,5,5,5-pentafluoropentanesulfonyl)-propylamino]-pentyl}-3-(tetrahydrapyran-2-yloxy)-estra-1,3,5(10)-trien-17β-ol is stirred in 18 ml of methanol and 1.8 ml of water at room temperature with 900 mg of oxalic acid. After 4 hours, the reaction mixture is stirred into ice water. The precipitated product is taken up in methylene chloride, washed with water, dried and concentrated by evaporation in a vacuum. After the crude product is chromatographed on silica gel with a methylene chloride-methanol gradient, 325 mg of 11β-fluoro-7α-{5-[N-methyl-N-3-(4,4,5,5,5-pentafluoropentanesulfonyl)-propylamnino]-pentyl}-estra-1,3,5(10)-triene-3,17β-diol with a melting point of 70° C. is obtained.

EXAMPLE 15

16α-Fluoro-17α-methyl-7α-{5-[N-methyl-N-3-(4,4,5,5,5-pentafluoro-pentylthio)-propylamino]-pentyl}-estra-1,3,5(10)-triene-3,17β-diol a) 7α-(5-Chloropentyl)estr-4-ene-3,17-dione 11.6 g of magnesium chips is suspended in 150 ml of anhydrous tetrahydrofuran, and the Grignard reagent is prepared with 58.8 ml of 1-bromo-5-chloro-pentane in 40 ml of anhydrous tetrahydrofuran. It is stirred for 30 minutes at room temperature, diluted with another 100 ml of anhydrous tetrahydrofuran and cooled to −70° C. Then, the solution of 3.04 g of copper(I)-bromide-dimethylsulfide complex in 72 ml of 1,3-dimethyltetrahydro-2(1H)-pyrimidinone (DMPU) and 150 ml of tetrahydrofuran are added in drops at an internal temperature of −65 to −70° C. Ultimately, the solution of 50 g of estra-4,6-diene-3,17-dione (Steroids Vol. 1, 1963, 223) and 75 ml of trimethylchlorosilane in 700 ml of anhydrous tetrahydrofuran is added within 2.5 hours. The mixture can be heated slowly to room temperature in a cooling bath while being stirred, acidified the next morning with 48 ml of acetic acid while being cooled with ice and mixed with ethyl acetate after being stirred for 15 minutes. The organic phase is extracted three times with saturated ammonium chloride solution, the aqueous phase is extracted with ethyl acetate, then the combined organic phases are washed with sodium bicarbonate solution, dried with magnesium sulfate and concentrated by evaporation in a vacuum. The residue of 53 g is chromatographed on silica gel with hexane/dichloromethane and ethyl acetate, yield 35 g of 7α-(5-chloropentyl)-estr-4-ene-3,17-dione The same product is obtained from 8.05 g of 7α-(5-hydroxypentyl)-estr-4-ene-3,17-dione (Example 1b) by a 3.5-hour reaction with 8.66 g of triphenylphosphine in 85 ml of carbon tetrachloride and 30 ml of acetonitrile at room temperature. The reaction mixture is diluted with dichloromethane, shaken out with saturated bicarbonate solution and with saturated common salt solution, dried with sodium sulfate and concentrated by evaporation in a vacuum. The residue is chromatographed on silica gel with dichloromethane and ethyl acetate, whereby 4.08 g of 7α-(5-chloropentyl)-estr-4-ene-3,17-dione is obtained, $[\alpha]_D^{22}=+68°$ (c=0.5% in chloroform)

b) 7α-(5-Chloropentyl)-3-hydroxy-estra-1,3,5(10)-trien-17-one 18.96 g of 7α-(5-chloropentyl)-estr-4-ene-3,17-dione is dissolved in 350 ml of anhydrous acetonitrile and mixed under inert gas at 80° C. with a solution of 4.36 g of lithium bromide and 22.5 g of copper(II) bromide in 390 ml of anhydrous acetonitrile. It is stirred for 5 more minutes, the mixture is cooled in an ice bath and mixed with water and ethyl acetate. The organic phase is shaken out with saturated sodium bicarbonate solution, the aqueous phase with ethyl acetate, the combined organic phases with saturated common salt solution, dried with sodium sulfate and concentrated by evaporation in a vacuum. The raw yield of 19.1 g is chromatographed on silica gel in hexane and ethyl acetate, whereby 10.0 g of oily 7α-(5-chloropentyl)-3-hydroxy-estra-1,3,5(10)-trien-17-one is obtained, which can be crystallized from hexane/dichloromethane.

Melting point 143.5° C., $[\alpha]_D^{22}=+112°$ (c=0.5% in chloroform)

c) Bis-3,17-trimethylsilyloxy-7α-(5-chloropentyl)-estra-1,3,5(10)-16-tetraene 5.65 g of 7α-(5-chloropentyl)-estra-1,3,5(10)-trien-3-ol-17-one, 9 ml of triethylamine and 9 ml of trifluoromethanesulfonic acid trimethylsilyl ester are dissolved in 75 ml of benzene, and it is refluxed for 2 hours. After cooling, it is diluted with hexane, the upper phase is shaken out with saturated sodium bicarbonate solution and with saturated common salt solution, dried with sodium sulfate, and concentrated by evaporation in a vacuum and yields bis-3,17-trimethylsilyloxy-7α-(5-chloropentyl)-estra-1,3,5(10),16-tetraene as oil.

d) 7α-(5-Chloropentyl)-16α-fluoro-estra-1,3,5(10)-trien-3-ol-17-one

The product of the test above is dissolved in 150 ml of anhydrous dichloromethane and mixed with 14.2 g of N-fluorobenzenesulfonimide. After 2 hours of stirring at room temperature, 50 ml of 8% sulfnuric acid is added, it is stirred intensively for another 3 hours, and then the phases are separated. The water phase is shaken out twice with dichloromethane, the organic phase is shaken out in succession with saturated sodium bicarbonate and sodium chloride solution, dried with sodium sulfate and concentrated by evaporation in a vacuum. The crude product of 15.3 g is chromatographed on silica gel with dichloromethane/diisopropyl ether, whereby 2.92 g of 7α-(5-chloropentyl)-16α-fluoro-estra-1,3,5(10)-trien-3-ol-17-one is obtained as an oil. The substance can be crystallized from diisopropyl ether, melting point 176° C., $[\alpha]_D^{22}=+114°$ (c=0.5% in chloroform).

e) 7α-(5-Chloropentyl)-16α-fluoro-17α-methyl-estra-1,3,5(10)-triene-3,17βdiol 3.0 g of 7α-(5-chloropentyl)-16α-fluoro-estra-1,3,5(10)-trien-3-ol-17-one is dissolved in 300 ml of anhydrous toluene under inert gas and mixed with 3 portions of 20 ml each of a 1.5-molar solution of methyllithium and lithium bromide in ether at room temperature at an interval of 15 minutes. After another 30 minutes, the reaction mixture is stirred into a semi-saturated ammonium chloride solution while being cooled with ice, acidified with 8% sulfuric acid and extracted with ethyl acetate. The combined organic phases are shaken out with sodium chloride solution, dried with sodium sulfate and concentrated by evaporation in a vacuum. The crude product of 3.2 g is chromatographed on silica gel with hexane and methyl-tert-butyl ether. The polar fraction of 1.21 g is 7α-(5-chloropentyl)-16α-fluoro-17α-methyl-estra-1,3,5(10)-triene-3,17β-diol, which crystallizes from diisopropyl ether/hexane, melting point 70° C., $[\alpha]_D^{22}=+7°$ (c=0.5% in chloroform).

f) 16α-Fluoro-17α-methyl-7α-{5-[N-methyl-N-3-(4,4,5,5,5-pentafluoropentylthio)-propylamino]-pentyl}-estra-1,3,5(10)-triene-3,17β-diol 40.8 mg of 7α-(5-chloropentyl)-16α-fluoro-17α-methyl-estra-1,3,5(10)-triene-3,17β-diol is dissolved in 0.5 ml of dimethylformamide, and the solution of 58 mg of 3-(N-methylamino)-propyl-4,4,5,5,5-pentafluoropentyl-sulfide and 13 mg of lithium iodide is added and heated for 17 hours to 100° C. under inert gas. After cooling, the mixture is mixed with ethyl acetate, shaken out in succession with saturated sodium bicarbonate and common salt solution, dried with sodium sulfate, and the solvent is evaporated in a vacuum. The residue is chromatographed on silica gel with ethyl acetate/methanol, yield 25 mg of 16α-fluoro-17α-methyl-7α-{5-[N-methyl-N-3-(4,5,5,5-pentafluoropentylthio)-propylamino]-pentyl}-estra-1,3,5(10)-triene-3,17β-diol; $[\alpha]_D^{22}=+5.6°$ (c=0.5% in chloroform); melting point 98.2° C.

EXAMPLE 16

16α-Fluoro-17β-methyl-7α-{5-[N-methyl-N-3-(4,4,5,5,5-pentafluoropentylthio)-propylamino]-pentyl}-estra-1,3,5(10)-triene-3,17α-diol As a nonpolar product of the chromatography in Example 15e), 7α-(5-chloropentyl)-16α-fluoro-17β-methyl-estra-1,3,5(10)-triene-3,17α-diol accumulates in an amount of 0.48 g. By crystallization from diisopropyl ether/hexane, crystals with a melting point of 65° C. and $[\alpha]_D^{22}=+5°$ (c=0.5% in chloroform) are obtained.

41 mg of the crystals are reacted as described in Example 15f), whereby 23 mg of 16α-fluoro-17β-methyl-7α-{5-[N-methyl-N-3-(4,4,5,5,5-pentafluoropentylthio)-propylamino]-pentyl}-estra-1,3,5(10)-triene-3,17α-diol is obtained; melting point 103.3° C. and $[\alpha]_D^{22}=+3.1°$ (c=0.5% in chloroform).

EXAMPLE 17

16α-Fluoro-17α-methyl-7α-{5-[N-methyl-N-3-(4,4,5,5,5-pentafluoropentanesulfinyl)-propylamino]-pentyl}-estra-1,3,5(10)-triene-3,17β-diol By oxidation with sodium periodate, as described in Example 2, 38 mg of 16α-fluoro-17α-methyl-7α-{5-[N-methyl-N-3-(4,4,5,5,5-pentafluoropentanesulfinyl)-propylamino]-pentyl}-estra-1,3,5(10)-triene-3,17β-diol is obtained from 72 mg of 16α-fluoro-17α-methyl-7α-{5-[N- methyl-N-3-(4,4,5,5,5-pentafluoropentylthio)-propylamino]-pentyl}-estra-1,3,5(10)-triene-3,17β-diol.

EXAMPLE 18

16α-Fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol As described in Example 15f), 40.8 mg of 7α-(5-chloropentyl)-16α-fluoro-17α-methyl-estra-1,3,5(10)-triene-3,17β-diol in dimethylformamide is reacted with 70 mg of 3-(N-methylamino)-propyl-4,4,5,5,5-pentafluoropentylsulfone. After working-up, 21 mg of 16α-fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol is obtained as oil; $[α]_D^{22}$=+2.4° (c=0.5% in chloroform).

EXAMPLE 19

16α-Fluoro-7α-{5-[N-methyl-N-3-(4,4,5,5,5-pentafluoropentylthio)-propylamino]-pentyl}-estra-1,3,5(10)-triene-3,17β-diol a) 7α-(5-Chloropentyl)-16α-fluoro-estra-1,3,5(10)-triene-3,17β-diol and 7α-(5-chloropentyl)-16α-fluoro-estra-1,3,5(10)-triene-3,17α-diol 392 mg of 7α-(5-chloropentyl)-16α-fluoro-estra-1,3,5(10)-trien-3-ol-17-one, Example 15d), in 2 ml of anhydrous tetrahydrofuran is dissolved, and 1.1 ml of a 1-molar solution of lithium tri-tert-butoxyaluminum hydride in tetrahydrofnaran is added while being cooled in an ice bath. It is allowed to stir for 30 minutes at 0° C., then mixed with water and 8% sulfuric acid until a weakly acidic reaction is achieved, and it is extracted three times with ethyl acetate. The organic phase is washed with saturated sodium chloride solution, dried with sodium sulfate and evaporated to dryness in a vacuum. The crude product is chromatographed on silica gel with hexane/ethyl acetate, whereby 118 mg of 7α-(5-chloropentyl)-16α-fluoro-estra-1,3,5(10)-triene-3,17β-diol and 138 mg of 7α-(5-chloropentyl)-16α-fluoro-estra-1,3,5(10)-triene-3,17α-diol is obtained, both as a solid foam.

b) 16α-Fluoro-7α-{5-[N-methyl-N-3-(4,4,5,5,5-pentafluoropentylthio)-propylamino]-pentyl}-estra-1,3,5(10)-triene-3,17β-diol By reaction of 100 mg of 7α-(5-chloropentyl)-16α-fluoro-estra-1,3,5(10)-triene-3,17β-diol with 3-(N-methylamino)-propyl4,4,5,5,5-pentafluoropentyl sulfide, as described in Example 15f), 83 mg of 16α-fluoro-7α-{5-[N-methyl-N-3-(4,4,5,5,5-pentafluoropentylthio)-propylamino]-pentyl }-estra-1,3,5(10)-triene-3,17β-diol is obtained as solid foam; $[α]_D^{22}$=+15.2° (c=0.5% in chloroform).

EXAMPLE 20

16α-Fluoro-7α-{5-[N-methyl-N-3-(4,4,5,5,5-pentafluoropentylthio)-propylamino]-pentyln}-estra-1,3,5(10)-trienen-3,17α-diol Analogously, 75 mg of 16α-fluoro-7α-(5-[N-methyl-N-3-(4,4,5,5,5-pentafluoropentylthio)-propyl-amino]-pentyl}-estra-1,3,5(10)-triene-3,17α-diol is obtained as foam in the same way from 100 mg of 7α-(5-chloropentyl)-16α-fluoro-estra-1,3,5(10)-triene-3,17α-diol; $[α]_D^{22}$=+6.9° (c=0.5% in chloroform).

EXAMPLE 21

16α-Fluoro-7α-{5-[N-methyl-N-3-(4,4,5,5,5-pentafluoro-pentanesulfinyl)-propylamino]-pentyln)-estra-1,3,5(10)-triene-3,17β-diol By oxidation of 85 mg of 16α-fluoro-7α-{5-[N-methyl-N-3-(4,4,5,5,5-pentafluoropentylthio)-propylamino]-pentyl}-estra-1,3,5(10)-triene-3,17β-diol with sodium periodate, as described in Example 17, 47 mg of 16α-fluoro-7α-{5-[N-methyl-N-3-(4,4,5,5,5-pentafluoropentyl-sulfinyl)-propylamino]-pentyl}-estra-1,3,5(10)-triene-3,17β-diol is obtained as foam.

EXAMPLE 22

16α-Fluoro-7α-{5-[N-methyl-N-3-(4,4,5,5,5-pentafluoropentanesulfonyl)-propylamino]-pentyl}-estra-1,3,5(10)-triene-3,17β-diol As described in Example 15f), 65 mg of 7α-5-(chloropentyl)-16α-fluoro-estra-1,3,5(10)-triene-3,17β-diol is reacted with 90 mg of 3-(N-methylamino)-propyl-4,4,5,5,5-pentafluoropentyl-sulfone, and 53 mg of 16α-fluoro-7α-{5-[N-methyl-N-3-(4,4,5,5,5-pentafluoropentanesulfonyl)-propylamino]-pentyl}-estra-1,3,5(10)-triene-3,17β-diol is obtained as oil.

EXAMPLE 23

7α-{5-[N-Methyl-N-3-(4,4,5,5,5-pentafluoropentylthio)-propylamino]-pentyl}-estra-1,3,5(10),14-tetraene-3,17β-diol a) 7α-(5-tert-Butyl-dimethylsilyloxypentyl)-estr-4-ene-3,17-dione In 34 ml of absolute tetrahydrofuran, 8.9 g of magnesium chips with 103 g of 1-bromo-5-tert-butyldimethylsilyloxypentane, dissolved in 110 ml of tetrahydrofuran, are reacted to form the Grignard reagent. 2.5 g of copper(I) bromide-dimethyl sulfide complex and a mixture of 60 ml of 1,3-dimethyl-3,4,5,6-tetrahydro-2(1H)-pyrimidinone and 70 ml of tetrahydrofuran are added to this solution at −70° C. to −65° C., and the resulting suspension is stirred for 30 more minutes at −70° C. under argon atmosphere.

Then, at −70° C. to −65° C., a solution of 50 g of estra-4,6-diene-3,17-dione [Steroids Vol. 1, 1963, 233–249] in 730 ml of absolute tetrahydrofuran and 62.7 ml of chlorotrimethylsilane is added in drops, and the mixture is stirred overnight at −70° C. For working-up, the reaction mixture is mixed with 48 ml of glacial acetic acid at −15° C., and, after 15 minutes of stirring, it is poured at this temperature into a mixture of saturated ammonium chloride solution and ethyl acetate. The organic phase is separated, and washed neutral in succession with saturated ammonium chloride solution, saturated sodium bicarbonate solution and ultimately with saturated common salt solution, dried on sodium sulfate and concentrated by evaporation.

The residue is chromatographed on silica gel with dichloromethanelacetone. 47 g of 7α-(5-tert-butyl-dimethylsilyloxypentyl)-estr-4-ene-3,17-dione is obtained as yellow oil. $[α]_D^{22}$=+62.2° (c=0.545 in chloroform).

b) 3-Hydroxy-7α-(5-hydroxypentyl)-estra-1,3,5(10),15-tetraen-17-one

According to the procedure indicated in Example 1b–1i, 62.7 g of 7α-(5-tert-butyl-dimethylsilyloxypentyl)-estr-4-ene-3,17-dione is reacted to form 15.8 g of 3-hydroxy-7α-(5-hydroxypentyl)-estra-1,3,5(10),15-tetraen-17-one.

c) 3-Benzyloxy-7α-(5-hydroxypentyl)-estra-1,3,5(10),15-tetraen-17-one

A solution of 2.85 g of 3-hydroxy-7α-(5-hydroxypentyl)-estra-1,3,5(10),15-tetraen-17-one in 57 ml of acetone is mixed with 3.25 g of cesium carbonate and 1.14 ml of benzyl bromide, and the mixture is refluxed for 1 hour. The reaction mixture is concentrated by evaporation, the residue is mixed with water, shaken out with ethyl acetate, the organic phase is dried on sodium sulfate and concentrated by evaporation. The residue is chromatographed on silica gel with hexane/ethyl acetate. 3.12 g of 3-benzyloxy-7α-(5-hydroxypentyl)-estra-1,3,5(10),15-tetraen-17-one is obtained as foam.

d) 17-Acetoxy-7α-{5-acetoxypentyl)-3-benzyloxy-estra-1,3,5(10),14,16-pentaene

A solution of 6.12 g of 3-benzyloxy-7α-(5-hydroxypentyl)-estra-1,3,5(10),15-tetraen-17-one in 717 ml of acetic anhydride is stirred with 920 mg of p-toluenesulfonic acid for 1 hour at room temperature. The reaction mixture is worked up according to the procedure indicated in Example 1j, and the crude product is chromatographed on silica gel with hexane/ethyl acetate. 4.6 g of 17-acetoxy-7α-(5-acetoxypentyl)-3-benzyloxy-estra-1,3,5(10),14,16-pentaene is obtained as oil.

e) 7α-(5-Acetoxypentyl)-3-benzyloxy-estra-1,3,5(10),14-tetraen-17β-ol

A solution of 1.25 g of sodium borohydride in 90 ml of ethanol and 18 ml of water is added in drops to a solution of 4.58 g of 17-acetoxy-7α-(5-acetoxypentyl)-3-benzyloxy-estra-1,3,5(10),14,16-pentaene in 26.8 ml of tetrahydrofnfi-ran and 161 ml of ethanol at room temperature, and the mixture is stirred for 1 hour. The reaction mixture is mixed with 4 ml of glacial acetic acid, concentrated by evaporation, and the residue is taken up in ethyl acetate. The organic phase is washed with sodium bicarbonate, dried on sodium sulfate and concentrated by evaporation. The residue is chromatographed on silica gel with hexane/ethyl acetate. 2.16 g of 7α-(5-acetoxypentyl)-3-benzyloxy-estra-1,3,5(10),14-tetraen-17β-ol is obtained as foam.

f) 3-Benzyloxy-7α-(5-hydroxypentyl)-estra-1,3,5(10),14-tetraen-17βol 2.16 g of 7α-(5-acetoxypentyl)-3-benzyloxy-estra-1,3,5(10),14-tetraen-17β-ol is saponified with 38 ml of 1N methanolic potassium hydroxide solution overnight at room temperature. The reaction mixture is poured into icen-cold saturated common salt solution, the precipitate is suctioned off, taken up in dichloromethane, washed with saturated common salt solution, dried on sodium sulfate and concentrated by evaporation. 1.86 g of 3-benzyloxy-7α-(5-hydroxypentyl)-estra-1,3,5(10),14-tetraen-17β-ol is obtained as foam.

g) 3-Benzyloxy-7α-(5-tosyloxypentyl)-estra-1,3,5(10),14-tetraen-17β-ol

Under the conditions of Example 1o, 3.03 g of 3-benzyloxy-7α-(5-hydroxypentyl)-estra-1,3,5(10),14-tetraen-17β-ol with 2.31 g of p-toluenesulfonic anhydride in 58 ml of pyridine is reacted, worked up and chromatographed on silica gel. 3 g of 3-benzyloxy-7α-(5-tosyloxy-pentyl)-estra-1,3,5(10),14-tetraen-17β-ol is obtained as foam.

h) 3-Benzyloxy-7α-{5-[N-methyl-N-3-(4,4,5,5,5-pentafluoropentylthio)-propyl-amino]-pentyl}-estra-1,3,5(10),14-tetraen17βol A solution of 2 g of 3-benzyloxy-7α-(5-tosyloxypentyl)-estra-1,3,5(10),14-tetraen-17β-ol in 28 ml of ethyl methyl ketone is stirred with 1.77 g of N-methyl-3-(4,4,5,5,5-pentafluoropentylthio)-propylamine in the presence of 950 mg of potassium carbonate and 230 mg of potassium iodide for 5 hours at a bath temperature of 80° C. The reaction mixture is poured into common salt solution, extracted with ethyl acetate, washed with common salt solution, dried on sodium sulfate and concentrated by evaporation. The residue is chromatographed on silica gel with hexane/ethyl acetate. 1.93 g of 3-benzyloxy-7α-{5-[N-methyl-N-3-(4,4,5,5,5-pentafluoropentylthio)-propylamino]-pentyl}-estra-1,3,5 (10),14-tetraen-17β-ol is obtained as resin. $[\alpha]_D^{22}$=+47.3° (c=0.505 in chloroform)

i) 7α-{5-[N-Methyl-N-3-(4,4,5,5,5-pentafluoropentylthio)-propylamino]-pentyl}-estra-1,3,5(10),14-tetraene3,17β-diol 10.2 ml of a 1.2-molar solution of diisobutylaluminum hydride in toluene is added in drops to a solution of 850 mg of 3-benzyloxy-7α-{5-[N-methyl-N-3-(4,4,5,5,5-pentafluoropentylthio)-propylamino]-pentyl}-estra-1,3,5 (10),14-tetraen-17β-ol in 10.2 ml of toluene at room temperature, and the mixture is heated for 5 hours at a bath temperature of 120° C. While being stirred and under argon atmosphere, the reaction mixture is added in drops to a mixture of saturated common salt solution and 2N sulfuric acid, extracted three times with ethyl acetate, the organic phase is washed twice with 2N sulfuric acid and three times with saturated commnon salt solution, dried on sodium sulfate and concentrated by evaporation. The residue is chromatographed on silica gel with hexane/ethyl acetate/ 0–30% methanol. 670 mg of 7α-{5-[N-methyl-N-3-(4,4,5,5,5-pentafluoropentylthio)-propylamino]-pentyl}-estra-1,3,5(10),14-tetraene-3,17β-diol is obtained as foam. $[\alpha]_D^{22}$=+43° (c=0.520 in chloroform/methanol).

EXAMPLE 24

7α-{5-[N-Methyl-N-3-(4,4,5,5,5-pentafluoropentanesulfinyl)-propylamino]-pentyl}-estra-1,3,5(10),14-tetraene-3,17β-diol Under the conditions of Example 2, 400 mg of 7α-{5-[N-methyl-N-3-(4,4,5,5,5-pentafluoropentylthio)-propylamino]-pentyl}-estra-1,3,5(10),14-tetraene-3,17β-diol with 177 mg of sodium periodate is reacted, worked up, and the crude product is chromatographed on silica gel with ethyl acetatelmethanol. 287 mg of the title compound is obtained as foam. $[\alpha]_D^{22}$=+30.70° (c=0.530 in chloroform/methanol).

EXAMPLE 25

7α-{5-[N-Methyl-N-3-(4,4,5,5,5-pentafluoropentanesulfonyl)-propylamino]-pentyl}-estra-1,3,5(10),14-tetraene-3,17β-diol a) 3-Benzyloxy-7α-{5-[N-Methyl-N-3-(4,4,5,5,5-pentafluoropentanesulfonyl)-propylamino]-pentyl}-estra-1,3,5(10),14-tetraen-17β-ol Under the conditions of Example 23h, 1 g of 3-benzyloxy-7α-(5-tosyloxypentyl)-estra-1,3,5(10),14-tetraen-17β-ol is reacted with 990 mg of N-methyl-3-(4,4,5,5,5-pentafluoropentanesulfonyl)-propyl-amine, worked up, and the crude product is chromatographed on silica gel with ethyl acetate/methanol. 960 mg of 3-benzyloxy-7α-{5-[N-methyl-N-3-(4,4,5,5,5-pentafluoropentanesulfonyl)-propylamino]-pentyl}-estra-1,3,5(10),14-tetraen-17β-ol is obtained as oil. $[\alpha]_D^{22}$=+48.5° (c=0.535 in chloroform)

b) 7α-{(5-[N-Methyl-N-3-(4,4,5,5,5-pentafluoropentanesulfonyl)-propylamino]-pentyl}-estra-1,3,5(10),14-tetraene-3,17β-diol A solution of 100 mg of 3-benzyloxy-7α-{5-[N-methyl-N-3-(4,4,5,5,5-pentafluoropentanesulfonyl)-propylamino]-pentyl}-estra-1,3,5(10),14-tetraen-17β-ol in 1 ml of dichnioromethane is mixed with 0.2 ml of dimethylaniline and 73 mg of aluminum chloride while being cooled in an ice bath, and it is stirred for 1 hour at this temperature. The reaction mixture is poured onto 1N hydrochloric acid, shaken out with ethyl acetate, washed with sodium bicarbonate solution and saturated common salt solution, dried on sodium sulfate and concentrated by evaporation. The crude

EXAMPLE 26

7α-{5-[(2S)-2-(4,4,5,5,
5Pentafluoropentylthiomethyl)-pyrrolidin-1-yl]-
pentyl}-estra-1,3,5(10)-triene-3,17β-diol a) 7α-(5-Acetoxypentyl)-3-benzyloxy-estra-1,3,5(10)-trien-17-one A solution of 6.5 g of 7α-(5-acetoxypentyl)-3-hydroxy-estra-1,3,5(10)-trien-17-one (Example 1d) in 65 ml of dimethylformamide is mixed with 3.3 ml of benzyl chloride, 8.7 g of cesium carbonate and 400 mg of sodium iodide, and it is stirred overnight at room temperature. The reaction mixture is poured into water, shaken out with ethyl acetate, the organic phase is washed with saturated common salt solution, dried on sodium sulfate and concentrated by evaporation. The residue is chromatographed on silica gel with hexane/ethyl acetate. 7.26 g of 7α-(5-acetoxypentyl)-3-benzyloxy-estra-1,3,5(10)-trien-17-one is obtained as oil.

b) 3-Benzyloxy-7α-(5-hydroxypentyl)-estra-1,3,5(10)-trien-17-one

A solution of 7.26 g of α-(5-acetoxypentyl)-3-benzyloxy-estra-1,3,5(10)-trien-17-one in 80 ml of methanol and 3 ml of tetrahydrofuran is saponified with 22.2 ml of 2N sodium hydroxide solution overnight at room temperature. The reaction solution is poured into 2N hydrochloric acid, shaken out with ethyl acetate, the organic phase is washed with saturated common salt solution, dried on sodium sulfate and concentrated by evaporation. 6.7 g of 3-benzyloxy-7α-(5-hydroxypentyl)-estra-1,3,5(10)-trien-17-one is obtained as foam.

c) 3-Benzyloxy-7α-(5-tosyloxypentyln)-estra-1,3,5(10)-trien-17-one

Under the conditions of Example 1o, 6.5 g of 3-benzyloxy-7α-(5-hydroxypentyl)-estra-1,3,5(10)-triene is reacted with 7.14 g of p-toluenesulfonic anhydride, worked up and chromatographed on silica gel with hexane/ethyl acetate. 7.45 g of 3-benzyloxy-7α-(5-tosyloxypentyl)-estra-1,3,5(10)-trien-17-one is obtained as foam. $[\alpha]_D^{22}=+80.6°$ (c=0.620 in chloroform).

d) 3-Benzyloxy-7α-{5-[(2S)-2-(4,4,5,5,5-pentafluoropentylthiomethyln)pyrrolidin-1-yl]-pentyl}-estra-1,3,5(10)-trien-17-one Under the conditions of Example 23h, 4.58 g of 3-benzyloxy-7α-(5-tosyloxypentyl)-estra-1,3,5(10)-trien-17-one is reacted with 3.17 g of (2S)-2-(4,4,5,5,5-pentafluoropentylthiomethyl)-pyrrolidine, worked up, and the crude product is chromato-graphed on silica gel with hexane/ethyl acetate. 3.9 g of 3-benzyloxy-7α-{5-[(2S)-2-(4,4,5,5,5-pentafluoropentyl-thiomethyl)-pyrrolidin-1-yl]-pentyl}-estra-1,3,5(10)-trien-17-one is obtained as oil. $[\alpha]_D^{22}=+32.5°$ (c=0.117 in chloroform).

e) 3-Hydroxy-7α-{5-[(2S-2-(4,4,5,5,5-pentafluoropentylthiomethyl)-pyrrolidin-1-yl]-pentyl}-estra-1,3,5(10)-trien-17-one Under the conditions of Example 6f, 2.05 g of 3-benzyloxy-7α-{5-[(2S)-2-(4,4,5,5,5-pentafluoropentylthiomethyl)-pyrrolidin-1yl]-pentyl}-estra-1,3,5(10)-trien-17-one is debenzylated. 1.25 g of 3-hydroxy-7α-{5-[(2S)-2-(4,4,5,5,5-pentafluoropentylthio-methyl)-pyrrolidin-1-yl]-pentyl}-estra-1,3,5(10)-trien-17-one is obtained as oil. $[\alpha]_D^{22}=+22.7°$ (c=0.475 in chloroform).

f) 7α-{5-[(2S)-2-(4,4,5,5,5-Pentafluoropentylthiomethyl)-pyrrolidin-1-yl]-pentyl}-estra-1,3,5(10)-trienne3,17β-diol Under the conditions of Example 8, 500 mg of 3-hydroxy-7α-{5-[(2S)-2-(4,4,5,5,5-pentafluoropentylthiomethyl)-pyrrolidin-1-yl]-pentyl}-estra-1,3,5(10)-trien-17-one is reduced with 100 mg of sodium borohydride. 325 mg of the title compound is obtained as oil. $[\alpha]_D^{22}=-8.7°$ (c=0.510 in methanol).

EXAMPLE 27

7α-{5-[(2R)-2-(4,4,5,5,5-Pentafluoropentylthiomethyl)-pyrrolidin-1-yl]-pentyl}-estra-1,3,5(10)-triene-3,17β-diol As described in Example 26d–f, 612 mg of the title compound is obtained as oil from 2.3 g of 3-benzyloxy-7α-(5-tosyloxypentyl)-estra-1,3,5(10)-trien-17-one (Example 26c) and 1.6 g of (2R)-2-(4,4,5,5,5-pentafluoropentylthiomethyl)-pyrrolidine.

EXAMPLE 28

17α-Methyl-7α-{5[(2S)-2-(4,4,5,5,5-pentafluoropentylthiomethyl)-pyrrolidin-1-yl]-pentyl}-estra-1,3,5(10)-triene-3,17β-diol a) 7α-(5-Chloropentyl)-17α-methyl-estra-1,3,5(10)-triene-3,17βdiol A suspension of 5.21 g of anhydrous cerium(III) chloride in 53.2 ml of tetra-hydrofuran is stirred for 2 hours at room temperature, 7 ml of a methylmagnesium bromide solution (3M in diethyl ether) is added in drops at 0° C., and the mixture is stirred for 30 minutes at 0° C. and for 15 minutes at room temperature. Then, a solution of 1 g of 7α-(5-chloropentyl)-3-hydroxy-estra-1,3,5(10)-trien-17-one (Example 15b) in 24 ml of tetrahydrofnfiran is added, and it is stirred for another 30 minutes at room temperature. The reaction mixture is poured onto ice-cold, saturated ammonium chloride solution, shaken out with ethyl acetate, the organic phase is dried on sodium sulfate and concentrated by evaporation. The residue is chromatographed on silica gel with hexane/ethyl acetate. 753 mg of 7α-(5-chloropentyl)-17α-methyl-estra-1,3,5(10)-triene-3,17β-diol is obtained as foam. $[\alpha]_D^{22}=+27.3°$ (c=0.515 in chloroform).

b) 7α-(5-Iodopentyl)-17α-methyl-estra-1,3,5(10)-triene-3,17β-diol

A solution of 735 mg of 7α-(5-chloropentyl)-17α-methyl-estra-1,3,5(10)-triene-3,17α-diol in 4 ml of ethyl methyl ketone is mixed with 5.6 g of sodium iodide and heated for 17 hours at a bath temperature of 80° C. The reaction mixture is poured into water, shaken out with ethyl acetate, the organic phase is washed with saturated common salt solution, dried on sodium sulfate and concentrated by evaporation. 834 mg of 7α-(5-iodopentyl)-17α-methyl-estra-1,3,5(10)-triene-3,17β-diol is obtained as foam. $[\alpha]_D^{22}=+20.2°$ (c=0.500 in chloroform).

c) 17α-Methyl-7α-{5-[(2S)-2-(4,4,5,5,5-pentafluoropentylthiomethyl)-pyrrolidin-1-yl]-pentyl}-estra-1,3,5(10)-triene-3,17β-diol A solution of 453 mg of 7α-(5-iodopentyl)-17α-methyl-estra-1,3,5(10)-triene-3,17α-diol and 390 mg of (2S)-2-(4,4,5,5,5-pentafluoropentylthiomethyl)-pyrrolidine in 8 ml of N-methyl-2-pyrrolidinone is heated for 4 hours to a bath temperature of 80° C. The cooled reaction mixture is poured into saturated sodium bicarbonate solution, shaken out with ethyl acetate, the organic phase is washed with saturated common salt solution, dried on sodium sulfate and concentrated by evaporation. The residue is chromatographed on silica gel with dichloromethane/ethyl acetate. 413 mg of the title compound is obtained as foam. $[\alpha]_D^{22}$=−25.8° (c=0.500 in chloroform).

EXAMPLE 29

11β-Fluoro-7α-{5-[2-(4,4,5,5,5-pentafluoropentylthiomethyl)-pyrrolidin-1-yl]-pentyl}-estra-1,3,5(10)-triene-3,17β-diol a) 7α-(5-Chloropentyl)-11β-fluoro-estr-4-ene3,17-dione A solution of 78.7 g of 11β-fluoro-7α-(5-hydroxypentyl)-estr-4-ene-3,17-dione (Example 12e) in 1.41 of carbon tetrachloride and 475 ml of acetonitrile is stirred with 71 g of triphenylphosphine for 8.5 hours at room temperature. Then, it is extracted with water, aqueous sodium bicarbonate and common salt solution, dried on sodium sulfate, concentrated by evaporation in a vacuum and chromatographed on silica gel with hexane/ethyl acetate. 48.0 g of 7α-(5-chloropentyl)-11β-fluoro-estr-4-ene-3,17-dione is obtained as crystals with a melting point of 51–53° C. $[\alpha]_D^{22}$=+78.5° (c=0.5% in chloroform).

b) 7α-(5-Chloropentyl)-11β-fluoro-3-hydroxy-estra-1,3,5(10)-trien-17-one

A solution of 10.34 g of lithium bromide and 53.2 g of copper(II) bromide in 280 ml of acetonitrile is added in drops to a solution of 47 g of 7α-(5-chloropentyl)-11β-fluoro-estr-4-ene-3,17-dione in 470 ml of acetonitrile at a bath temperature of 80° C. After 20 ml is added, the bleaching of the solution is awaited, and the remainder of the solution is added in 12 minutes and then stirred for 5 more minutes at a bath temperature of 80° C. Then, it is cooled to 0° C., mixed with sodium bicarbonate solution, added to water, extracted 4 times with ethyl acetate, washed neutral, dried on sodium sulfate, concentrated by evaporation in a vacuum and chromatographed on silica gel with hexane/ethyl acetate. 25.3 g of 7α-(5-chloropentyl)-11β-fluoro-3-hydroxy-estra-1,3,5(10)-trien-17-one is obtained. $[\alpha]_D^{22}$=+115.4° (c=0.5% in chloroform).

c) 11β-Fluoro-3-hydroxy-7α-{5-[2-(4,4,5,5,5-pentafluoropentylthiomethyl)-pyrro-lidin-1-yl]-pentyl}-estra-1,3,5(10)-trien-17-one A solution of 785.9 mg of 7α-(5-chloropentyl)-11β-fluoro-3-hydroxy-estra-1,3,5(10)-trien-17-one in 7 ml of N-methyl-2-pyrrolidinone is mixed with 535.5 mg of lithium iodide and 520 mg of (2S)-2-(4,4,5,5,5-pentafluoropentylthiomethyl)-pyrrolidine, and it is stirred for 2.5 hours at a bath temperature of 100° C. Then, it is poured onto water, extracted 3 times with diethyl ether, washed neutral, dried on sodium sulfate, concentrated by evaporation in a vacuum and chromatographed on silica gel with dichloromethane/methanol. 525 mg of pure 11β-fluoro-3-hydroxy-7α-{5-[2-(4,4,5,5,5-pentafluoropentylthiomethyl)-pyrrolidin-1-yl]-pentyl}-estra-1,3,5(10)-trien-17-one is obtained. $[\alpha]_D^{22}$=+29.3° (c=0.5% in chloroform).

d) 11β-Fluoro-7α-{5-[2-(4,4,5,5,5-pentafluoropentylthiomethyl)-pyrrolidin-1-yl]-pentyl}-estra-1,3,5(10)-triene-3,17-diol 500 mg of 11β-fluoro-3-hydroxy-7α-{5-[2-(4,4,5,5,5-pentafluoropentylthiomethyl)-pyrrolidin-1-yl]-pentyl}-estra-1,3,5(10)-trien-17-one in 5 ml of tetrahydrofuran, 2.75 ml of ethanol and 1.1 ml of water, and 100 mg of sodium borohydride is added at a bath temperature of 0° C., and it is stirred for 0.5 hour at room temperature. Then, it is added to water, extracted 3 times with ethyl acetate, washed neutral with saturated common salt solution, dried on sodium sulfate, concentrated by evaporation in a vacuum and chromatographed on silica gel with dichloromethane/methanol.

441.3 mg of 11β-fluoro-7α-{5-[2-(4,4,5,5,5-pentafluoropentylthiomethyl)-pyrrolidin-1-yl]-pentyl}-estra-1,3,5(10)-triene-3,17β-diol is obtained as crystals with a melting point of 174–176° C. $[\alpha]_D^{22}$=−14.9° (c=0.5% in pyridine).

EXAMPLE 30

11β-Nitrooxy-7α-(9-[4,4,5,5,5-pentafluoropentanesulfonyl]-nonyl)-estra-1,3,5(10)-trienen-3,17β-diol a) 3,17β-Diacetyloxy-7α-(9-[4,4,5,5,5pentafluoropentanesulfonyl]-nonyl)-estra-1,3,5(10)-triene 6.28 g of 7α-(9-[4,4,5,5,5-pentafluoropentanesulfinyl]-nonyl)-estra-1,3,5(10)-triene-3,17α-diol is dissolved in 30 ml of pyridine, mixed with 15 ml of acetic anhydride while being cooled with water and then allowed to stir for 5 hours at room temperature.

For working-up, the reaction solution is poured onto ice water, the diacetate is extracted with ethyl acetate, the organic phase is washed with dilute sulfnuiric acid, water, saturated common salt solution and dried on sodium sulfate. As a crude product, an oil, which is taken up in 100 ml of acetic acid, is obtained, and it is mixed with 15 g of sodium perborate. After five hours of stirring at room temperature, the reaction is complete.

The reaction mixture is poured onto ice water and then extracted with ethyl acetate. The organic phase is freed from acid residues with aqueous bicarbonate solution. After drying on sodium sulfate, it is filtered, concentrated by evaporation and chromatographed on silica gel (hexane/ethyl acetate, 7:3). 6.83 g of product is obtained as foam.

b) 3,17β-Diacetyloxy-11β-nitrooxy-7α-(9-[4,4,5,5,5-pentafluoropentanesulfonyl]-nonyl)-estra-1,3,5(10)-trien-9-ol 18.6 g of cerium ammonium nitrate is added to a solution of 3.0 g of 3,17β-diacetyloxy-7α-(9-[4,4,5,5,5-pentafluoropentanesulfonyl]-nonyl)-estra-1,3,5(10)-triene in 50 ml of aqueous acetic acid (90%), and it is stirred for 4 hours at room temperature.

For working-up, the reaction solution is poured onto ice water, extracted with ethyl acetate, and the organic phase is washed neutral with aqueous bicarbonate solution. Then, it is washed with saturated common salt solution and dried on sodium sulfate.

The crude product is chromatographed on silica gel (hexane/ethyl acetate, 7:3). 2.0 g of product is obtained as yellow-colored foam.

c) 3,17β-Diacetyloxy-11β-nitrooxy-7α-(9-[4,4,5,5,5-pentafluoropentanesulfonyl]-nonyl)-estra-1,3,5(10)-triene For reductive removal of the 9α-hydroxy group in 3,17β-diacetyloxy-11β-nitrooxy-7α-(9-[4,4,5,5,5-pentafluoropentanesulfonyl]-nonyl)-estra-1,3,5(10)-trien-9-ol, 2.0 g of starting material is dissolved in 25 ml of dichloromethane, cooled to −15° C. and mixed successively with 15 ml of triethylsilane and 2.2 ml of boron trifluoride ethorate. After one hour of stirring at −15° C., the cold bath is removed and allowed to thaw to room temperature.

For working-up, it is poured onto ice water, extracted with dichloromethane, the organic phase is washed with aqueous bicarbonate solution, saturated common salt solution and dried on sodium sulfate.

The crude product is chromatographed on silica gel (hexane/ethyl acetate, 9:1), yield 1.3 g of foam.

d) 11β-Nitrooxy-7α-(9-[4,4,5,5,5-pentafluoropentanesulfonyl]-nonyl)-estra-1,3,5(10)-triene-3,17β-diol For saponification, 1.0 g of 3,17β-diacetyloxy-11β-nitrooxy-7α-(9-[4,4,5,5,5-pentafluoropentane-sulfonyl]- nonyl)-estra-1,3,5(10)-triene is dissolved in 50 ml of methanol, mixed with 20 ml of 3% methanolic potassium hydroxide solution and allowed to stand for 4 hours at room temperature.

The reaction mixture is poured into citric acid ice water and then extracted with ethyl acetate. After the organic phase is washed with water and saturated common salt solution, it is dried on sodium sulfate.

The crude product is chromatographed on silica gel (hexane/ethyl acetate, gradient to 3:2), yield 0.53 g as oil.

EXAMPLE 31

11β-Fuoro-17α-methyl-7α-{5-[(2S)-2-(4,4,5,5,5-pentanfluoropentylthiomethyl)-pyrrolidin-1-yl]-pentyln}-estra-1,3,5(10)-triene-3,17β-diol a) 7α-(5-Chloropentyl)-11β-fluoro-17α-methyl-estra-1,3,5(10)-triene-3,17β-diol Under the conditions of Example 28a, 750 mg of 7α-(5-chloropentyl)-11β-fluoro-3-hydroxy-estra-1,3,5(10)-trien-17-one (Example 29b) is reacted with 4.9 ml of methylmagnesium bromide solution (3 M in diethyl ether), worked up and chromatographed. 561 mg of 7α-(5-chloropentyl)-11β-fluoro-17α-methyl-estr-1,3,5(1l0)-triene-3,17,β-diol is obtained as foam. $[\alpha]_D^{22}$=+51.60° (c=0.515 in chloroform).

b) 11β-Fluoro-17α-methyl-7α-{5-[(2S)-2-(4,4,5,5,5pentafluoropentylthiomethyl)-pyrrolidin-1-yl]-pentyln}-estra-1,3,5(10)-triene-3,17β-diol Under the conditions of Example 15f, 408 mg of 7α-(5-chloropentyl)-11β-fluoro-17α-methyl-estra-1,3,5(10)-triene-3,17β-diol in 5 ml of N-methyl-2-pyrrolidinone is reacted in the presence of 130 mg of lithium iodide with 606 mg of (2S)-2-(4,4,5,5,5-pentafluoropentylthiomethyl)-pyrrolidine, worked up and chromatographed. 326 mg of the title compound is obtained as oil.
$[\alpha]_D^{22}$=−5.8° (c=0.535% in chloroform).

EXAMPLE 32

11β-Fluoro-17α-methyl-7α-{5-[(2S)-2-(4,4,5,5,5-pentaluoropentanesulfinylmethyl)-pyrrolidin-1-yl]-pentyl}-estra-1,3,5(10)-triene-3,17β-diol Under the conditions of Example 13, 260 mg of 11β-fluoro-17α-methyl-7α-{(5-[(2S)-2-(4,4,5,5,5-pentafluoropentylthiomethyl)-pyrrolidin-1-yl]-pentyl}-estra-1,3,5(10)-triene-3,17,β-diol (Example 31b) is reacted with 151 mg of sodium periodate, worked up and chromatographed. 129 mg of the title compound is obtained as oil.

EXAMPLE 33

3,17β-Diacetoxy-11β-fluoro-17α-methyl-7α-{5-[(2S)-2-(4,4,5,5,5-pentafluoro-pentanesulfonylmethyl)-pyrrolidin-1-yl]-pentyl}-estra-1,3,5(10)-triene-3,17βdiol Under the conditions of Example 3, 65 mg of 11β-fluoro-17α-methyl-7α-{ 5-[(2S)-2-(4,4,5,5,5-pentafluoropentylthiomethyl)-pyrrolidin-1-yl]-pentyl}-estra-1,3,5(10)-triene-3,17β-diol (Example 31b) is acetylated with acetic anhydride, and the crude product is oxidized with sodium perborate tetrahydrate, as described in Example 4, worked up and chromatographed. 27 mg of the title compound is obtained as oil.

EXAMPLE 34

7α-{5-[(2S)-2-(4,4,5,5,5-Pentafluoropentanesulfinylmethyl)-pyrrolidin-1-yl]-pentyl}-estra-1,3,5(10)-triene-3,17β-diol By oxidation with sodium periodate, 66 mg of the title compound, as described in Example 2, is obtained as oil from 152 mg of 7α-{5-[(2S)-2-(4,4,5,5,5-pentafluoropentylthiomethyl)-pyrrolidin-1-yl]-pentyl}-estra-1,3,5(10)-triene-3,17β-diol (Example 26f). $[\alpha]_D^{22}$=+11.8° (c=0.53 in methanol).

EXAMPLE 35

7α-{5-[(2S)-2-(4,4,5,5,5-Pentafluoropentanesulfonylmethyl)-pyrrolidin-1-yl]-pentyl}-estra-1,3,5(10)-triene-3,17β-diol Under the conditions of Example 3, 76 mg of 7α-{5-[(2S)-2-(4,4,5,5,5-pentafluoropentylthiomethyl)-pyrrolidin-1-yl]-pentyl}-estra-1,3,5(10)-triene-3,17β-diol (Example 26f) is acetylated with acetic anhydride, and the crude product is oxidized, as described in Example 4, with sodium perborate tetrahydrate, worked up and chromatographed. 31 mg of the title compound is obtained as oil. $[\alpha]_D^{22}$=30.6° (c=0.515 in methanol).

EXAMPLE 36

11β-Fluoro-17α-methyl-7α-{5-[N-methyl-N-3-(4,4,5,5,5-pentafluoropentylthio)-propylamino]-pentyl}-estra-1,3,5(10)-triene-3,17β-diol a) 11β-Fluoro-3-hydroxy-17α-methyl-7α-{5-[N-methyl-N-3-(4,4,5,5,5-pentafluoropentylthio)-propylamino]-pentyl}-estra-1,3,5(10)-trien-17-one A solution of 2.0 g of 11β-fluoro-7α-{5-[N-methyl-N-3-(4,4,5,5,5-pentafluoropentylthio)-propylamino]pentyl}-3-(tetrahydrapyran-2-yloxy)-estra-1,3,5(10)-trien-17-one in 20 ml of methanol and 2 ml of water is stirred at room temperature with 1.2 g of oxalic acid. After 2.5 hours, it is added to ice water, extracted with dichloromethane, washed with saturated common salt solution, dried on sodium sulfate, concentrated by evaporation in a vacuum and chromatographed on silica gel with dichloromethane/methanol. 1.2 g of 11β-fluoro-3-hydroxy-17α-methyl-7α-{5-[N-methyl-N-3-(4,4,5,5,5-pentafluoropentylthio)-propylamino]-pentyl}-estra-1,3,5(10)-trien-17-one is obtained as foam. $[\alpha]_D^{22}$=+69° (c=0.5% in chloroform).

b) 11β-Fluoro-17α-methyl-7α-{5-[N-methyl-N-3-(4,4,5,5,5-pentafluoropentylthio)-propylamino]-pentyl}-estra-1,3,5(10)-trienne-3,17β-diol 33 ml of a 1.6-molar ethereal lithium methylate solution is added in drops to 5 g of 11β-fluoro-3-hydroxy-17α-methyl-7α-{5-[N-methyl-N-3-(4,4,5,5,5-pentafluoropentylthio)-propylamino]-pentyl}-estra-1,3,5(10)-trien-17-one in 150 ml of tetrahydrofuran at room temperature. After 2.5 hours, saturated ammonium chloride solution is added while being cooled with ice, extracted with ethyl acetate, washed with saturated common salt solution, dried on sodium sulfate and concentrated by evaporation in a vacuum. After chromatography on silica gel, which contains 2% triethylamine, with dichnioromethane/methanol, 2.0 g of 11β-fluoro-17α-methyl-7α-{5-[N-methyl-N-3-(4,4,5,5,5-pentafluoropentylthio)-propylamino]-pentyl}-estra-1,3,5(10)-triene-3,17β-diol is obtained as crystals with a melting point of 83° C.

EXAMPLE 37

11β-Fluoro-17α-methyl-7α-{5-[N-methyl-N-3-(4,4,5,5,5-pentafluoropentanesulfinyl)-propylamino]-pentyl}-estra-1,3,5(10)-triene-3,17β-diol A solution of 500 mg of 11β-fluoro-17α-methyl-7α-{5-[N-methyl-N-3-(4,4,5,5,5-pentafluoropentylthio)-propylamino]-pentyl}-estra-1,3,5(10)-triene-3,17β-diol in 20 ml of methanol and 0.9 ml of water is stirred at room temperature with 355 mg of sodium periodate for 3 hours. Then, it is poured onto ice water, extracted with dichloromethane, washed with saturated common salt solution, dried on sodium sulfate, concentrated by evaporation in a vacuum and chromatographed on silica gel with dichloromethane/methanol. 216 mg of 11β-fluoro-17α-methyl-7α-{5-[N-methyl-N-3-(4,4,5,5,5-pentafluoropentanesulfinyl)-propylamino]-pentyl}-estra-1,3,5(10)-triene-3,17β-diol is obtained as crystals with a melting point of 83.4° C.

EXAMPLE 38

11β-Fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol a) 11β-Fluoro-3-hydroxy-17α-methyl-7α-{5-[N-methyl-N-3-(4,4,5,5,5-pentafluoropentanesulfonyl)-propylamino]-pentyl}-estra-1,3,5(10)-trien-17-one A solution of 3 g of 7α-(5-chloropentyl)-11β-fluoro-3-hydroxy-estra-1,3,5(10)-trien-17-one in 50 ml of dimethylformamide is stirred with 1.6 g of lithium iodide and 6.2 g of methyl-[3-(4,4,5,5,5-pentafluoropentanesulfonyl)-propyl]-amine for 22 hours at 100° C. Then, it is extracted with ethyl acetate, washed with saturated common salt solution, dried on sodium sulfate, concentrated by evaporation in a vacuum and chromatographed on silica gel with dichloromethane/methanol. 4.5 g of 11β-fluoro-3-hydroxy-17α-methyl-7α-{5-[N-methyl-N-3-(4,4,5,5,5-pentafluoropentanesulfonyl)-propylamino]-pentyl}-estra-1,3,5(10)-trien-17-one is obtained as foam.

b) 11β-Fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol A suspension of 11.4 g of anhydrous cerium(III) chloride in 120 ml of tetrahydrofuran is stirred for 2 hours at room temperature under nitrogen, mixed at 0° C. drop by drop with 17.5 ml of a 3-molar, ethereal methylmagnesium bromide solution, stirred for 30 minutes, a solution of 3.5 g of 11β-fluoro-3-hydroxy-17α-methyl-7α-{5-[N-methyl-N-3-(4,4,5,5,5-pentafluoropentanesulfonyl)-propylamino]-pentyl}-estra-1,3,5(10)-trien-17-one in 24 ml of tetrahydrofuran is added, and it is stirred for another 30 minutes. Then, saturated ammonium chloride solution is added, diluted with ethyl acetate, washed with saturated common salt solution, dried on sodium sulfate, concentrated by evaporation in a vacuum and chromatographed on silica gel with dichloromethane/methanol. 2.2 g of 11β-fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol is obtained as crystals with a melting point of 82.5° C.

EXAMPLE 39

11β-Fluoro-7α-{5-[N-methyl-N-2-(4,4,5,5,5-pentafluoropentanesulfonyl)-ethylamino]-pentyl}-estra-1,3,5(10)-triene-3,17β-diol a) 7α-{5-Bromopentyl}-11β-fluoro-estr-4-ene-3,17-dione A solution of 33 g of 11β-fluoro-7α-(5-hydroxypentyl)-estr-4-ene-3,17-dione in 330 ml of dichloromethane is mixed at −5° C. with 28.9 g of triphenylphosphine and 36.7 g of carbon tetrabromide, and it is stirred for 0.5 hour. Then, dichloromethane is added and washed with water, saturated sodium bicarbonate and common salt solution. The organic phase is dried on sodium sulfate and concentrated by evaporation in a vacuum. Then, the crude product is chromatographed on silica gel with a hexane-ethyl acetate gradient. 28.5 g of 7α-(5-bromopentyl)-11β-fluoro-estr-4-ene-3,17-dione with a melting point of 75–76° C. is obtained.

b) 7α-(5-Bromopentyl)-11β-fluoro-3-hydroxy-estra-1,3,5(10)-trien-17-one 17.0 g of copper(II) bromide is added to 27.8 g of 7α-(5-bromopentyl)-11β-fluoro-estr-4-ene-3,17-dione in 190 ml of acetonitrile at 80° C. After 8 hours, the reaction mixture is stirred into water, extracted three times with ethyl acetate, washed twice with ammonium chloride, with sodium bicarbonate and common salt, dried and concentrated by evaporation in a vacuum. After the crude product is chromatographed on silica gel with a hexane-ethyl acetate gradient, 20.4 g of 7α-(5-bromopentyl)-11β-fluoro-3-hydroxy-estra-1,3,5(10)-trien-17-one is obtained as colorless crystals with a melting point of 178° C.

c) 7α-(5-Bromopentyl)-11β-fluoro-estra-1,3,5(10)-triene-3,17β-diol

A solution of 16.2 g of 7α-(5-bromopentyl)-11β-fluoro-3-hydroxy-estra-1,3,5(10)-trien-17-one in 162 ml of tetrahydrofuran as well as 90 ml of ethanol and 36 ml of water are mixed in portions at 0° C. with 4.7 g of sodium borohydride and stirred for 2 hours at 0° C. Then, it is added to water, extracted four times with ethyl acetate, washed with water and common salt solution, dried on sodium sulfate and concentrated by evaporation in a vacuum. 17.1 g of crude product is obtained. After chromatography on silica gel with hexane/ethyl acetate, 15.6 g of pure 7α-(5-bromopentyl)-11β-fluoro-estra-1,3,5(10)-triene-3,17β-diol is obtained.

d) 11β-Fluoro-7α-[5-(methylamino)-pentyl]-estra-1,3,5(10)-triene-3,17β-diol

A solution of 2 g of 7α-(5-bromopentyl)-11β-fluoro-estra-1,3,5(10)-triene-3,17β-diol in 20 ml of dimethylformamide is stirred with 8 ml of a 40% aqueous methylamine solution for 3.5 hours at 80° C. Then, it is added to water, extracted three times with ethyl acetate, washed with water and common salt solution, dried on sodium sulfate and concentrated by evaporation in a vacuum. 1.77 g of 11β-fluoro-7α-[5-(methylamino)-pentyl]-estra-1,3,5(10)-triene-3,17β-diol is obtained.

e) 11β-Fluoro-7α-[5-N-methyl-N-2-(4,4,5,5,5-pentafluoropentanesulfonyl)-ethyl-amino]-pentyl}-estra-1,3,5(10)-triene-3,17β-diol A solution of 440 mg of 11β-fluoro-7α-[5-(methylamino)-pentyl]-estra-1,3,5(10)-triene-3,17β-diol in 15 ml of methanol is stirred with 500 mg of 4,4,5,5,5-pentafluoropentylvinylsulfone for 1 hour at 90° C. Then, it is added to water, extracted three times with ethyl acetate, washed with water and common salt solution, dried on sodium sulfate, concentrated by evaporation in a vacuum and chromatographed on silica gel with dichloromethane/methanol. 488 mg of 11β-fluoro-7α-{5-[N-methyl-N-2-(4,4,5,5,5-pentafluoropentanesulfonyl)-ethylamino]-pentyl}-estra-1,3,5(10)-triene-3,17β-diol is obtained as crystals with a melting point of 74–76° C.

The reacted intermediate stage 12k) has a strong antiestrogenic action:

EXAMPLE 40

11β-Fluoro-7α-{5-[N-methyl-N-3-(4,4,5,5,5-pentafluoropentylthio)-propylamino]-pentyl}-3-hydroxy-estra-1,3,5(10)-trien-17-one A solution of 1.6 g of 11β-fluoro-7α-{5-[N-methyl-N-3-(4,4,5,5,5-pentafluoropentylthio)-propylamino]-pentyl}-3-(tetrahydropyran-2-yloxy)-estra-1,3,5(10)-trien-17-one in 20 ml of methanol and 2 ml of water is stirred with 1.0 g of oxalic acid. After 3 hours, the reaction mixture is added to ice water. It is extracted with methylene chloride, washed with saturated sodium chloride solution, dried and concentrated by evaporation in a vacuum. After the crude product is chromatographed on silica gel with a methylene chloride-methanol gradient, 1.1 g of 11β-fluoro-7α-{5-[N-methyl-N-3-(4,4,5,5,5-pentafluoropentylthio)-propylamino]-pentyl}-3-hydroxy-estra-1,3,5(10)-trien-17-one is obtained. $[\alpha]_D^{22}=+69°$ (c=0.5% in chloroform)

EXAMPLE 41

11β-Fluoro-7α-{6-[N-methyl-N-3-(4,4,5,5,5-pentafluoropentylthio)-propylamino]-hexyl}-estra-1,3,5(10)-triene-3,17β-dione a) 7α-(6-Chlorohexyl)-11β-fluoro-estr-4-ene-3,17-dione First 30 ml of a solution that consists of 41 ml of 1-bromo-6-chlorohexane in 270 ml of THF is added to a suspension of 6.8 g of magnesium chips in 100 ml of THF. After the reaction starts, the remaining solution is added in drops in such a way that the internal temperature does not exceed 35° C. In a second flask, 48.1 g of lithium bromide is added to a suspension of 26.4 g of copper(I) iodide in 120 ml of THF at 0° C., whereby the internal temperature climbs to 40° C. Without cooling, 46.4 ml of 1,3-dimethyl-3,4,5,6-tetrahydro-(1H)-pynrmidin-2-one is now added and stirred for 30 minutes at 40° C. A clear solution is obtained, which is added in drops to the Grignard solution that is cooled to −40° C. Then, it is stirred for 30 more minutes at −30° C. and mixed drop by drop at −50° C. with a solution of 23.5 g of 11β-fluoro-estra-4,6-diene-3,17-dione in 230 ml of THF, 24.6 ml of 1,3-dimethyl-3,4,5,6-tetrahydro-(1H)-pyrimidin-2-one and 55 ml of trimethylchlorosilane in such a way that the internal temperature does not exceed −40° C. It is stirred for 1 hour cold, then 32 ml of glacial acetic acid is added in drops, the cooling bath is removed and stirred for 1 more hour at room temperature. For working-up, the reaction mixture is added to 1.5l of water, diluted with the same amount of ethyl acetate, the precipitate is separated on Celite, rewashed with ethyl acetate, the aqueous phase is extracted 3 times with ethyl acetate, washed with sodium bicarbonate and common salt solution, dried on magnesium sulfate and concentrated by evaporation in a vacuum. After the crude product is chromatographed on silica gel with a hexane-ethyl acetate gradient, 25.2 g of 7α-(6-chlorohexyl)-11β-fluoro-estr-4-ene-3,17-dione is obtained.

b) 7α-(6-Chlorohexyl)-11β-fluoro-3-hydroxy-estra-1,3,5(10)-trien-17-one 28.1 g of copper(II) bromide and 5.4 g of lithium bromide in 105 ml of anhydrous acetonitrile are added to 25.2 g of 7α-(6-chlorohexyl)-11β-fluoro-estr-4-ene-3,17-dione in 175 ml of anhydrous acetonitrile at 80° C. After 15 minutes, the reaction mixture is cooled to 0° C., and 250 ml of saturated sodium bicarbonate solution is added in drops. Then, the solution is stirred into 1 liter of water, brought to pH=6 with 2N hydrochloric acid, extracted 3 times with ethyl acetate, washed with common salt solution, dried on magnesium sulfate and concentrated by evaporation in a vacuum. Chromatography of the crude product on silica gel with a hexane-ethyl acetate gradient yields 5.7 g of 7α-(6-chlorohexyl)-11β-fluoro-3-hydroxy-estra-1,3,5(10)-trien-17-one as a foam.

c) 11β-Fluoro-3-hydroxy-7α-(6-iodohexyl)-estra-1,3,5(10)-trien-17-one 2.7 g of 7α-(6-chlorohexyl)-11β-fluoro-3-hydroxy-estra-1,3,5(10)-trien-17-one is dissolved in 40 ml of ethyl methyl ketone, mixed with 3.0 g of sodium iodide and stirred overnight at a bath temperature of 90° C. For working-up, the reaction mixture is cooled to room temperature, stirred into water, extracted 3 times with ethyl acetate, washed with common salt solution, dried on magnesium sulfate and concentrated by evaporation in a vacuum. 3.4 g of 11β-fluoro-3-hydroxy-7α-(6-iodohexyl)-estra-1,3,5(10)-trien-17-one is obtained as crude product, which is used without further purification in the next stage.

d) 11β-Fluoro-3-hydroxy-7α-{6-[N-methyl-N-3-(4,4,5,5,5-pentafluoropentylthio)-propylamino]-hexyl}-estra-1,3,5(10)-trien-17-one 2.5 g of 11β-fluoro-3-hydroxy-7α-(6-iodohexyl)-estra-1,3,5(10)-trien-17-one in 20 ml of anhydrous DMF is stirred at a bath temperature of 100° C. with 2.0 g of methyl-[3-(4,4,5,5,5-pentafluoropentylthio)-propyl]-amine. After 2 hours, the reaction solution is poured into semi-saturated sodium bicarbonate solution, extracted 3 times with methylene chloride, dried on magnesium sulfate and concentrated by evaporation in a vacuum. The residue is chromatographed on silica gel with a methylene chloride-methanol gradient. 3.15 g of 11β-fluoro-3-hydroxy-7α-{6-[N-methyl-N-3-(4,4,5,5,5-pentafluoropentylthio)-propylamino]-hexyl}-estra-1,3,5(10)-trien-17-one is obtained as a foam.

e) 11β-Fluoro-7α-{6-[N-methyl-N-3-(4,4,5,5,5-pentafluoropentylthio)-propyl-amino]-hexyl}-estra-1,3,5(10)-triene-3,17-diol 250 mg of 11β-fluoro-3-hydroxy-7α-{6-[N-methyl-N-3-(4,4,5,5,5-pentafluoro-pentylthio)-propyl-amino]-hexyl}-estra-1,3,5(10)-trien-17-one is dissolved in 4.5 ml of methanol and mixed at 0° C. in portions with 60 mg of sodium borohydride. After 3 hours of stirring at room temperature, the solvent is drawn off in a vacuum, the residue is mixed with saturated common salt solution, extracted 3 times with methylene chloride, dried on magnesium sulfate and concentrated by evaporation in a vacuum. After chromatography on silica gel with a methylene chloride-methanol gradient, 165 mg of 11β-fluoro-7α-{6-[N-methyl-N-3-(4,4,5,5,5-pentafluoropentylthio)-propylamino]-hexyl}-estra-1,3,5(10)-triene-3,17-diol is obtained as a foam, $[\alpha]_D^{22}=+37°$ (c=1.01 in chloroform).

EXAMPLE 42

11β-Fluoro-7α-{6-[N-methyl-N-3-(4,4,5,5,5-pentafluoropentanesulfinyl)-propylamino]-hexyl}-estra-1,3,5(10)-triene-3,17-diol a) 11β-Fluoro-3-hydroxy-7α-{6-[N-methyl-N-3-(4,4,5,5,5-pentafluoropentanesulfinyl)-propylamino]-hexyl}-estra-1,3,5(10)-trien-17-one 500 mg of 11β-fluoro-3-hydroxy-7α-{6-[N-methyl-N-3-(4,4,5,5,5-pentafluoropentylthio)-propyl-amino]-hexyl}-estra-1,3,5(10)-trien-17-one is dissolved in 17 ml of methanol and 3.3 ml of water, mixed with 262 mg of sodium periodate and stirred for 2 hours at room temperature. For working-up, the reaction mixture is mixed with semi-saturated common salt solution, extracted 3 times with methylene chloride, dried on magnesium sulfate and concentrated by evaporation in a vacuum. The residue is purified on silica gel with a methylene chloride-methanol gradient. 149 mg of 11β-fluoro- 3-hydroxy-7α-{6-[N-methyl-N-3-(4,4,5,5,5-pentafluoropentanesulfinyl)-propylamino]-hexyl}-estra-1,3,5(10)-trien-17-one is isolated as a foam, $[\alpha]_D=+45°$ (c=1.015 in chloroform).

b) 11β-Fluoro-7α-{6-[N-methyl-N-3-(4,4,5,5,5pentafluoropentanesulfinyl)-propyl-amino]-hexyl}-estra-1,3,5(10)-triene-3,17-diol 149 mg of 11β-fluoro-3-hydroxy-7α-{6-[N-methyl-N-3-(4,4,5,5,5-pentafluoropentanesulfinyl)-propyl-amino]-hexyl}-estra-1,3,5(10)-trien-17-one is dissolved in 3 ml of methanol and mixed in portions with 35 mg of sodium borohydride. After 30 minutes of stirring at room temperature, the solvent is drawn off in a vacuum, the residue is mixed with water, extracted 3 times with methylene chloride, dried on magnesium sulfate and concentrated by evaporation in a vacuum. Preparatinve thin-layer chromatography with methylene chloride/methanol=9/1 as a solvent provides 109 mg of 11β-fluoro-7α-{6-[N-methyl-N-3-(4,4,5,5,5-pentafluoropentanesulfinyl)-propylamino]-hexyl}-estra-1,3,5(10)-triene-3,17-diol as a foam, [α]$_D$=+24° (c=0.51 in chloroform).

Example 43

11β-Fluoro-7α-(5-{[N-3-(furan-2-ylmethylthio)-propyl]-N-methyl-amino}-pentyl)-estra-1,3,5(10)-triene-3,17β-diol a) 7α-(5-Chloropentyl)-11β-fluoro-estr-4-ene-3,17-dione First, 20% of a solution of 39 ml of 1-bromo-5-chloropentane in 300 ml of THF is added to a suspension of 7.2 g of magnesium chips in 100 ml of THF under nitrogen. After the reaction starts, which can be achieved by adding iodine and dibromomethane, the remaining solution is added in drops in such a way that the internal temperature does not exceed 35° C. In a second flask, 51.2 g of lithium bromide is added to a suspension of 28.1 g of copper(I) iodide in 130 ml of THF at 0° C., whereby the internal temperature climbs to 40° C. Without cooling, 49.4 ml of 1,3-dimethyl-3,4,5,6-tetrahydro-1H)-pyrimidin-2-one is now added and stirred for 15 minutes at 40° C. A clear solution is obtained, which is added in drops to the Grignard solution that is cooled to −50° C. Then, it is stirred for 15 more minutes at −30° C. and mixed at −70° C. drop by drop with a solution of 25 g of 11β-fluoro-estra-4,6-diene-3,17-dione in 260 ml of THF, 26 ml of 1,3-dimethyl-3,4,5,6-tetrahydro-(1H)-pyrimidin-2-one and 59 ml of trimethylchlorosilane in such a way that the internal temperature does not exceed −65° C. It is stirred for 30 minutes cold, then 34.7 ml of glacial acetic acid is added in drops, the cooling bath is removed, and it is stirred for 1 more hour at room temperature. For working-up, the reaction mixture is added to 1.5 l of water, diluted with the same amount of ethyl acetate, the precipitate is separated on Celite, rewashed with ethyl acetate, the aqueous phase is extracted 3 times with ethyl acetate, washed with sodium bicarbonate and common salt solution, dried on magnesium sulfate and concentrated by evaporation in a vacuum. After the crude product is chromatographed on silica gel with a hexane-ethyl acetate gradient, 22.1 g of 7α-(5-chloropentyl)-11β-fluoro-estr-4-ene-3,17-dione is obtained.

b) 7α-(5-Chloropentyl)-11β-fluoro-3-hydroxy-estra-1,3,5(10)-trien-17-one 25.4 g of copper(II) bromide and 4.9 g of lithium bromide in 95 ml of anhydrous acetonitrile are added to 22.1 g of 7α-(5-chloropentyl)-11β-fluoro-estr-4-ene-3,17-dione in 160 ml of anhydrous acetonitrile at 80° C. After 20 minutes, the reaction mixture is cooled to 0°C., and 200 ml of saturated sodium bicarbonate solution is added in drops. Then, the solution is stirred into 750 ml of water, brought to pH=6 with 2N hydrochloric acid, extracted 3 times with ethyl acetate, washed with common salt solution, dried on magnesium sulfate and concentrated by evaporation in a vacuum. Chromatography of the crude product on silica gel with a hexane-ethyl acetate gradient yields 14.7 g of 7α-(5-chloropentyl)-11β-fluoro-3-hydroxy-estra-1,3,5(10)-trien-17-one.

c) 11β-Fluoro-3-hydroxy-7α-(5-iodopentyl)-estra-1,3,5(10)-trien-17-one 5.0 g of 7α-(5-chloropentyl)-11β-fluoro-3-hydroxy-estra-1,3,5(10)-trien-17-one is dissolved in 80 ml of ethyl methyl ketone, mixed with 5.7 g of sodium iodide and stirred overnight at a bath temperature of 90° C. For working-up, the reaction mixture is cooled to room temperature, stirred into water, extracted 3 times with ethyl acetate, washed with common salt solution, dried on magnesium sulfate and concentrated by evaporation in a vacuum. 6.8 g of 11β-fluoro-3-hydroxy-7α-(5-iodopentyl)-estra-1,3,5(10)-trien-17-one is obtained as crude product, which is used without further purification in the next stage.

d) 11β-Fluoro-3-hydroxy-7α-[5-(methylamino)-pentyl]-estra-1,3,5(10)-trien-17-one 5.1 g of methylamine is condensed in a solution of 6.8 g of 11β-fluoro-3-hydroxy-7α-(5-iodopentyl)-estra-1,3,5(10)-trien-17-one in 35 ml of anhydrous tetrahydrofiran at −78° C., and it is stirred overnight at room temperature in a pressurized reactor. After the pressurized reactor was opened at −20° C., it was allowed to reach room temperature to be able to evaporate excess methylamine. Then, the reaction solution is added to saturated sodium bicarbonate solution, extracted 3 times with ethyl acetate, dried on magnesium sulfate and concentrated by evaporation in a vacuum. 6.7 g of 11β-fluoro-3-hydroxy-7α-[5-(methylamino)-pentyl]-estra-1,3,5(10)-trien-17-one is obtained as crude product.

e) 11β-Fluoro-7α-(5-{[N-3-(furan-2-ylmethylthio)-propyl]-N-methyl-amino}-pentyl)-3-hydroxy-estra-1,3,5(10)-trien-17-one 526 mg of 11β-fluoro-3-hydroxy-7α-[5-(methylamino)-pentyl]-estra-1,3,5(10)-trien-17-one and 95 mg of 2-(3-chloro-propylthiomethyl)-furan are dissolved in 5 ml of ethyl methyl ketone, mixed with 112 mg of sodium iodide and 104 mg of potassium carbonate and stirred for 3 hours at a bath temperature of 90° C. For working-up, the reaction mixture is added to semi-saturated sodium bicarbonate solution, extracted 3 times with methylene chloride, washed with common salt solution, dried on magnesium sulfate and concentrated by evaporation in a vacuum. Chromatography of the crude product on silica gel with a methylene chloride-methanol gradient yields 22 mg of 11β-fluoro-7α-{5-{[N-3-(furan-2-ylmethylthio)-propyl]-N-methyl-amino}-pentyl)-3-hydroxy-estra-1,3,5(10)-trien-17-one as a foam.

f) 11β-Fluoro-7α-(5-{[N-3-(furan-2-ylmethylthio)-propyl]-N-methyl-amino}-pentyl)-estra-1,3,5(10)-triene-3,17β-diol 217 mg of 11β-fluoro-7α-(5-{[N-3-(furan-2-ylmethylthio)-propyl]-N-methyl-amino}-pentyl)-3-hydroxy-estra-1,3,5(10)-trien-17-one is dissolved in 6 ml of methanol and mixed in portions with 44 mg of sodium borohydride. After 1 hour of stirring at room temperature, the solvent is drawn off in a vacuum, the residue is mixed with common salt solution, extracted 3 times with methylene chloride, dried on magnesium sulfate and concentrated by evaporation in a vacuum. Preparative column chromatography with a methylene chloride/methanol gradient provides 146 mg of 11β-fluoro-7α-(5-{[N-3-(furan-2-ylmethylthio)-propyl]-N-methyl-amino}-pentyl)-estra-1,3,5(10)-triene-3,17β-diol as a foam.

EXAMPLE 44

11β-Fluoro-7α-(5-{N-methyl-[N-3-(thiophen-2-ylmethylthio)-propyl]-amino}-pentyl)-estra-1,3,5(10)-triene-3,17β-diol a) 11β-Fluoro-3-hydroxy-7α-(5-{N-methyl-[N-3-(thiophen-2-ylmethylthio)-propyl]-amino}-pentyl)-estra-1,3,5(10)-trien-17-one 526 mg of 11β-fluoro-3-hydroxy-7α-[5-(methylamino)-pentyl]-estra-1,3,5(10)-trien-17-one and 103 mg of 2-(3-chloropropylthiomethyl)-thiophene are dissolved in 5 ml of ethyl methyl ketone, mixed with 112 mg of sodium iodide and 104 mg of potassium carbonate and stirred for 4.5 hours at a bath temperature of 90° C. For working-up, the reaction mixture is added to semi-saturated sodium bicarbonate solution, extracted 3 times with methylene chloide, washed with common salt solution, dried on magnesium sulfate and concentrated by evaporation in a vacuum. Chromatography of the crude product on silica gel with a methylene chloride-methanol gradient yields 191 mg of 11β-fluoro-3-hydroxy-7α-(5-{N-methyl-[N-3-(thiophen-2-ylmethylthio)-propyl]-amino}-pentyl)-estra-1,3,5(10)-trien-17-one as a foam.

b) 11β-Fluoro-7α-(5-{N-methyl-[N-3-(thiophen-2-ylmethylthio)-propyl]-amino}-pentyl)-estra-1,3,5(10)-triene-3,17β-diol 185 mg of 11β-fluoro-3-hydroxy-7α-(5-{N-methyl-[N-3-(thiophen-2-ylmethylthio)-propyl]-amino}-pentyl)-estra-1,3,5(10)-trien-17-one is dissolved in 5 ml of methanol and mixed in portions with 28 mg of sodium borohydride. After 45 minutes of stirring at room temperature, the solvent is drawn off for the most part in a vacuum, the residue is added to common salt solution, extracted 3 times with methylene chloride, dried on magnesium sulfate and concentrated by evaporation in a vacuum. Preparative column chromatography with a methylene chloride/methanol gradient provides 93 mg of 11β-fluoro-7α-(5-{N-methyl-[N-3-(thiophen-2-ylmethylthio)-propyl]-amino}-pentyl)-estra-1,3,5(10)-triene-3,17β-diol as a foam.

EXAMPLE 45

11β-Fluoro-7α-{5-[(2S)-2-(4-trifluoromethylphenylthiomethyl)-pyrrolidin-1-yl]-pentyl}-estra-1,3,5(10)-triene-3,17β-diol a) 11β-Fluoro-3-hydroxy-7α-{5-[(2S)-2-(4-trifluoromethylphenylthiomethyl)-pyrrolidin-1-yl]-pentyl}-estra-1,3,5(10)-trien-17-one A solution of 0.5 g of 7α-(5-chloropentyl)-11β-fluoro-3-hydroxy-estra-1,3,5(10)-trien-17-one in 4 ml of dimethylformamide is stirred with 0.55 g of (2S)-2-(4-trifluoromethylphenylthiomethyl)-pyrrolidine and 0.32 g of lithium iodide for 2 hours at a bath temperature of 100° C. Then, it is added to sodium bicarbonate solution, extracted three times with ethyl acetate, washed with common salt solution, dried on sodium sulfate, concentrated by evaporation in a vacuum and chromatographed on silica gel with dichloromethane/acetone. 0.45 g of 11β-fluoro-3-hydroxy-7α-{5-[(2S)-2-(4-trifluoromethylphenylthiomethyl)-pyrrolidin-1-yl]-pentyl}-estra-1,3,5(10)-trien-17-one with $[α]_D^{22}=+32.7°$ (c=0.51% in chloroform) is obtained.

b) 11β-Fluoro-7α-{5-[(2S)-2-(4-trifluoromethylphenylthiomethyl)-pyrrolidin-1-yl]-pentyl}-estra-1,3,5(10)-triene-3,17β-diol A solution of 0.43 g of 11β-fluoro-3-hydroxy-7α-{5-[(2S)-2-(4-trifluoromethylphenylthiomethyl)-pyrrolidin-1-yl]-pentyl}-estra-1,3,5(10)-trien-17-one in 4 ml of tetrahydrofuran, 2.3 ml of ethanol and 1 ml of water is mixed in portions at 0° C. with 111 mg of sodium borohydride, and it is stirred for 2 hours. Then, it is added to ice water, extracted three times with ethyl acetate, washed with common salt solution, dried on sodium sulfate, concentrated by evaporation in a vacuum and chromatographed on silica gel with dichloromethane/acetone. 0.32 g of 11β-fluoro-7α-{5-[(2S)-2-(4-trifluoromethylphenylthiomethyl)-pyrrolidin-1-yl]-pentyl}-estra-1,3,5(10)-triene-3,17β-diol with $[α]_D^{22}=+16.2°$ (c=0.51% in methanol) is obtained.

EXAMPLE 46

11β-Fluoro-17α-methyl-7α-{5-[(2S)-2-(4,4,5,5,5-pentafluoropentanesulfinylmethyl)-pyrrolidin-1-yl]-pentyl}-estra-1,3,5(10)-triene-3,17β-diol A solution of 0.2 g of 11β-fluoro-17α-methyl-7α-{5-[(2S)-2-(4,4,5,5,5-pentafluoropentylthiomethyl)-pyrrolidin-1-yl]-pentyl}-estra-1,3,5(10)-triene-3,17β-diol in 5.8 ml of methanol and 2.9 ml of water is stirred with 82 mg of sodium periodate for 5 hours at room temperature. Then, it is added to water, extracted three times with dichloromethane, washed neutral, dried on sodium sulfate and concentrated by evaporation in a vacuum. 210 mg of crude product, which is chromatographed on silica gel with dichloromethane/methanol, is obtained. 105 mg of pure 14,17-ethano-7α-{5-[N-methyl-N-3-(4,4,5,5,5-pentafluoropentanesulfinyl)-propylamino]-pentyl}-estra-1,3,5(10)-triene-3,17β-diol IR 1610 and 1190 [cm$^{-1}$] is obtained.

EXAMPLE 47

11β-Fluoro-17α-methyl-7α-{5-[(2R)-2-(4,4,5,5,5pentafluoropentylthiomethyl)-pyrrolidin-1-yl]-pentyl}-estra-1,3,5(10)-triene-3,17β-diol Analogously to Example 29, 11β-fluoro-17α-methyl-7α-{5-[(2R)-2-(4,4,5,5,5-pentafluoropentylthiomethyl)-pyrrolidin-1-yl]-pentyl}-estra-1,3,5(10)-triene-3,17β-diol with $[α]_D^{22}=+68.7°$ (c=0.74% in chloroform) is obtained.

EXAMPLE 48

11β-Fluoro-17α-methyl-7α-{5-[(2S)-2-(4,4,5,5,5-pentafluoropentanesulfonylmethyl)-pyrrolidin-yl]-pentyl}-estra-1,3,5(10)-triene-3,17β-diol A solution of 100 mg of 3,17β-diacetoxy-11-fluoro-17α-methyl-7α-{5-[(2S)-2-(4,4,5,5,5-pentafluoropentanesulfonylmethyl)-pyrrolidin-1-yl]-pentyl}-estra-1,3,5(10)-triene in 1.3 ml of 0.2 M methanolic potassium hydroxide solution is stirred for 2 hours at room temperature. Then, it is added to water, extracted three times with dichloromethane, washed with common salt solution, dried on sodium sulfate, concentrated by evaporation in a vacuum and chromatographed on silica gel with dichloromethane/acetone. 63 mg of 11β-fluoro-17α-methyl-7α-{5-[(2S)-2-(4,4,5,5,5-pentafluoropentanesulfonylmethyl)-pyrrolidin-1-yl]-pentyl}-estra-1,3,5(10)-triene-3,17β-diol is obtained.

IR: 1710, 1660, 1610 [cm$^{-1}$].

EXAMPLE 49

11β-Fluoro-7α-{5-[(2S)-2-(4,4,5,5,5-pentafluoropentanesulfinylmethyl)-pyrrolidin-1-yl]-pentyl}-estra-1,3,5(10)-triene-3,17β-diol A solution of 300 mg of 11β-fluoro-7α-{5-[(2S)-2-(4,4,5,5,5-pentafluoropentylthiomethyl)-pyrrolidin-1-yl]-pentyl}-estra-1,3,5(10)-triene-3,17β-diol in 4.3 ml of methanol and 2.1 ml of water is stirred with 131 mg of sodium periodate for 4 hours at room temperature. Then, it is added to water, extracted three times with ethyl acetate, washed with common salt solution, dried on sodium sulfate, concentrated by evaporation in a vacuum and chromatographed on silica gel with dichloromethane/ethyl acetate. 203 mg of 11β-fluoro-7α-{5-[(2S)-2-(4,4,5,5,5-pentafluoropentanesulfinylmethyl)-pyrrolidin-1-yl]-pentyl}-estra-1,3,5(10)-triene-3,17β-diol is obtained. $[α]_D^{22}=+11.8°$ (c=0.53% in methanol).

EXAMPLE 50

11β-Fluoro-7α-{5-[(2S)-2-(4,4,5,5,5-pentafluoropentanesulfonylmethyl)-pyrrolidin-1-yl]-pentyl}-estra-1,3,5(10)-triene-3,17β-diol Analogously to what is described in Example 48, 11β-fluoro-7-α-{5-[(2S)-2-(4,4,5,5,5- pentafluoropentanesulfonylmethyl)-pyrrolidin-1-yl]-pentyl}-estra-1,3,5(10)-triene-3,17β-diol is obtained. $[\alpha]_D^{22}=+30.6°$ (c=0.515% in methanol).

Production of Starting Compounds

N-Methyl-[3-(4,4,5,5,5-pentafluoropentylthio)-propyl]-amine
a) 3-Iodopropyl-4,4,5,5,5-pentafluoropentylsulfide A solution of 22.8 g of 3-chloropropyl-4,4,5,5,5-pentafluoropentylsulfide in 500 ml of ethyl methyl ketone is stirred with 40 g of sodium iodide for 5 hours at a bath temperature of 100° C. under nitrogen. Then, it is evaporated to dryness in a vacuum, added to water, extracted three times with ethyl acetate, washed neutral, and dried on sodium sulfate and concentrated by evaporation in a vacuum. 30.6 g of 3-iodopropyl-4,4,5,5,5-pentafluoropentylsulfide is obtained.

b) N-Methyl-[3-(4,4,5,5,5-pentafluoropentylthio)-propyl]-amine

In a solution of 30.6 g of 3-iodopropyl-4,4,5,5,5-pentafluoropentylsulfide in 200 ml of absolute tetrahydrofuran, 45 g of methylanrine is condensed at a bath temperature of –78° C., and it is stirred for 1.5 hours at room temperature and for 4 hours at 60° C. in the pressurized reactor. To open the reactor, it is allowed to cool overnight to room temperature and then to –78° C. Then, it is allowed to reach room temperature, excess methylamine is evaporated, diluted with ethyl acetate, washed neutral, dried on sodium sulfate, concentrated by evaporation in a vacuum and chromatographed on silica gel with dichloromethane/methanol. 15.7 g of N-methyl-[3-(4,4,5,5,5-pentafluoropentylthio)-propyl]-amine is obtained as an oil.

N-Methyl-[3-(4,4,5,5,5pentafluoropentanesulfonyl)-propyl]-amine
a) 3-Chloropropyl-4,4,5,5,5-pentafluoropentanesulfone A solution of 23 g of 3-chloropropyl-4,4,5,5,5-pentafluoropentylsulfide in 230 ml of chloroform is mixed in portions at 0° C. with 41.8 g of 70% m-chloroperbenzoic acid, and it is stirred for 1.5 hours at room temperature. Then, it is diluted with dichloromethane, washed with sodium hydrogen sulfite solution, sodium bicarbonate solution and common salt solution, dried on sodium sulfate and concentrated by evaporation in a vacuum. 23.8 g of pure 3-chloropropyl-4,4,5,5,5-pentafluoropentanesulfone is obtained as crystals with a melting point of 74–76° C.

b) 3-Iodopropyl-4,4,5,5,5-pentafluoropentanesulfone

A solution of 23.5 g of 3-chloropropyl4,4,5,5,5-pentafluoropentanesulfone in 500 ml of ethyl methyl ketone is stirred with 40 g of sodium iodide for 5 hours at a bath temperature of 100° C. under nitrogen. Then, it is evaporated to dryness in a vacuum, added to water, extracted three times with ethyl acetate, washed neutral, and dried on sodium sulfate and concentrated by evaporation in a vacuum. 30.6 g of 3-iodopropyl-4,4,5,5,5-pentafluoropentanesulfone is obtained as crystals with a melting point of 88–89° C.

c) N-Methyl-[3-(4,4,5,5,5-pentafluoropentanesulfonyl)-propyl]-amine

A solution of 23.5 g of 3-iodopropyl-4,4,5,5,5-pentafluoropentanesulfone in 200 ml of absolute tetrahydrofuran is condensed at a bath temperature of –78° C. with 44 g of methylamine, and it is stirred for 1.5 hours at room temperature and for 4 hours at 60° C. in a pressurized reactor. To open the reactor, it is allowed to cool overnight to room temperature and then to –78° C. Then, it is allowed to reach room temperature, excess methylamine is evaporated, diluted with ethyl acetate, washed neutral, dried on sodium sulfate, concentrated by evaporation in a vacuum and chromatographed on silica gel with dichloromethane/methanol. 14.8 g of N-methyl-[3-(4,4,5,5,5-pentafluoropentanesulfonyl)-propyl]-amine is obtained as crystals with a melting point of 55–57° C.

1-Bromo-5-tert-butyldimethylsilyloxypentane
a) 5-Bromo-1-pentanol 50 ml of concentrated sulfuric acid is added in drops to a solution of 50 g of 5-bromopentyl acetate in 1.6 of methanol, and the mixture is stirred for 30 hours at room temperature. The methanol is drawn off in a vacuum, the residue is taken up in diethyl ether, washed neutral with saturated common salt solution, dried on sodium sulfate and concentrated by evaporation. 28 g of 5-bromo-1-pentanol is obtained as crude product.

b) 1-Bromo-5-tert-butyldimethylsilyloxypentane

A solution of 28 g of crude 5-bromo-1-pentanol in 144 ml of tetrahydrofuran is mixed with 24 g of imidazole. Then, a solution of 30.3 g of tert-butyldimethylchlorosilane in 46 ml of tetrahydrofuran is added in drops, and it is stirred for 4 hours at room temperature. The reaction mixture is poured into water, shaken out with diethyl ether, the organic phase is washed 4 times with water, dried on sodium sulfate and concentrated by evaporation. The crude product is chromatographed on silica gel with hexane/diethyl ether. 42 g of the title compound is obtained as a colorless liquid.

(2S)-2-(4,4,5,5,5-Pentafluoropentylthiomethyl)-pyrrolidine
a) N-tert-Butyloxycarbonyl-L-prolinol-p-tosylate 24.2 g of p-toluenesulfonic anhydride is added in portions to a solution of 10 g of N-tert-butyloxycarbonyl-L-prolinol in 170 ml of pyridine at 0°C., and the mixture is stirred for 5 hours at 0° C. The reaction mixture is poured onto 2N hydrochloric acid, extracted with ethyl acetate, the organic phase is washed with saturated common salt solution, dried on sodium sulfate and concentrated by evaporation. 17.7 g of N-tert-butyloxycarbonyl-L-prolinol-p-tosylate is obtained as oily crude product. $[\alpha]_D^{22}=-28.0°$ (c=0.545 in chloroform).

b) N-tert-Butyloxycarbonyl-(2S)-2-(4,4,5,5,5-pentafluoropentylthiomethyl)-pyrrolidine A solution of 3.93 g of 4,4,5,5,5-pentafluoropentylthioacetate in 18 ml of methanol is mixed with 2.94 ml of a sodium methanolate solution (30% in methanol), and it is stirred for 30 minutes at room temperature. This reaction solution is added to a solution of 3.0 g of N-tert-butyloxycarbonyl-L-prolinol-p-tosylate, and the mixture is stirred for 3 hours at room temperature and for 3 hours at 50° C. The reaction mixture is poured into water, extracted with ethyl acetate, washed with saturated sodium chloride solution, dried on sodium sulfate and concentrated by evaporation. The residue is chromatographed on silica gel with hexanelethyl acetate. 2.59 g of N-tert-butyloxycarbonyl-(2S)-2-(4,4,5,5,5-pentafluoropentylthiomethyl)-pyrrolidine is obtained as an oil. $[\alpha]_D^{22}=-41.3°$ (c=0.530 in chloroform).

c) (2S)-2-(4,4,5,5,5-Pentafluoropentylthiomethyl)-pyrrolidine 2.55 g of N-tert-butyloxycarbonyl-(2S)-2-(4,4,5,5,5-pentafluoropentylthiomethyl)-pyrrolidine is added to 5.4 ml of trifluoroacetic acid, cooled to 0°C., and the mixture is stirred for 1.5 hours at 0° C. and for 16 hours at room temperature. The reaction mixture is poured onto 10% sodium bicarbonate solution, extracted with ethyl acetate, washed with saturated common salt solution, dried on sodium sulfate and concentrated by evaporation. 1.8 g of the title compound is obtained as oily crude product.

(2R)-2-(4,4,5,5,5-Pentafluoropentylthiomethyl)-pyrrolidine

Exactly as described in the production of (2S)-2-(4,4,5,5,5-pentafluoropentylthiomethyl)-pyrrolidine, 9.69 g of the title compound is obtained as oily crude product from 10 g of N-tert-butyloxy-carbonyl-D-prolinol.

Production of New Starting Compounds

(4,4,5,5,5-Pentafluoropentyl)-vinyl sulfone a) (4,4,5,5,5-Pentafluoropentyl)-vinyl sulfide A solution of 40 g of 4,4,5,5,5-pentafluoropentylthioacetate in 200 ml of methanol is stirred with 34 ml of a 30% sodium methylate for 1 hour at 25° C., mixed drop by drop with 21 ml of 1,2-dibromoethane, stirred for another 2 hours at room temperature, mixed drop by drop with another 70 ml of 30% sodium methylate and stirred for 3 hours at 25° C. Then, methanol is concentrated by evaporation in a vacuum, added to water, extracted three times with ethyl acetate, washed with water and common salt solution, dried on sodium sulfate and concentrated by evaporation in a vacuum. 34 g of (4,4,5,5,5-pentafluoropentyl)-vinyl sulfide is obtained.

b) (4,4,5,5,5-Pentafluoropentyl)-vinyl sulfone

A solution of 34 g of (4,4,5,5,5-pentafluoropentyl)-vinyl sulfide in 74 ml of glacial acetic acid is mixed drop by drop with 59 ml of 30% hydrogen peroxide in such a way that the reaction temperature does not exceed 70° C. Then, it is stirred for one hour at a bath temperature of 70° C. Then, it is added to water, extracted three times with ethyl acetate, washed with sodium thiosulfate, water and common salt solution, dried on sodium sulfate, concentrated by evaporation in a vacuum and chromatographed on silica gel with hexane/ethyl acetate. 12.3 g of (4,4,5,5,5-pentafluoropentyl)-vinyl sulfone is obtained as an oil.

Production of New Starting Compounds 2

2-(3-Chloro-propylthiomethyl)-furan 3.3 ml of a 30% sodium methylate solution in methanol is added in drops to 1.77 ml of furan-2-yl-methanethiol in 18 ml of anhydrous acetonitrile at 0° C. After 5 minutes, the drop-by-drop addition of 2.6 ml of 1-bromo-3-chloropropane is carried out. Then, the reaction solution is allowed to stir for 5 hours at room temperature. For working-up, the batch is diluted with ethyl acetate, washed with water and common salt solution, dried on magnesium sulfate and concentrated by evaporation in a vacuum. Chromatography of the crude product on silica gel with a hexane-ethyl acetate gradient yields 1.1 g of 2-(3-chloropropylthiomethyl)-furan as an oil.

2-(3-Chloro-propylthiomethyl)-thiophene 1.5 ml of a 30% sodium methylate solution in methanol is added in drops to 1.0 g of thiophen-2-yl-methanethiol in 8 ml of anhydrous acetonitrile at 0° C. After 5 minutes, the drop-by-drop addition of 1.1 ml of 1-bromo-3-chloropropane is carried out. Then, the reaction solution is allowed to stir for 5 hours at room temperature. For working-up, the batch is diluted with ethyl acetate, washed with water and common salt solution, dried on magnesium sulfate and concentrated by evaporation in a vacuum. Chromatography of the crude product on silica gel with a hexane-ethyl acetate gradient yields 1.3 g of 2-(3-chloropropylthiomethyl)-thiophene as an oil.

(2S)-2-(4-Trifluoromethylphenylthiomethyl)-pyrrolidine a) N-tert-Butyloxycarbonyl-(2S)-2-(4-trifluoromethylphenylthiomethyl)-pyrrolidine A solution of 1.65 g of 4-trifluoromethylthiophenol in 18 ml of dimethylformarnide is mixed with 3 g of cesium carbonate and 3 g of N-tert-butyloxycarbonyl-L-prolinol-p-tosylate, and it is stirred for 8 hours at room temperature. The reaction mnixture is poured into water, extracted with ethyl acetate, washed with saturated sodium chloride solution, dried on sodium sulfate and concentrated by evaporation. The residue is chromatographed on silica gel with hexane/ethyl acetate. 2.59 g of N-tert-butyloxycarbonyl-(2S)-2-(4-trifluoromethylphenylthiomethyl)-pyrrolidine is obtained as an oil.

b) (2S)-2-(4-Trifluoromethylphenylthiomethyl)-pyrrolidine

A solution of 2.55 g of N-tert-butyloxycarbonyl-(2S)-2-(4-trifluoromethylphenylthiomethyl)-pyrrolidine in 5.64 ml of trifluoroacetic acid is stirred for 1 hour at 0° C. and then for 3.5 hours at room temperature. The reaction mixture is poured onto 10% sodium bicarbonate solution, extracted with ethyl acetate, washed twice with 2 M hydrochloric acid, the water phase is extracted with ether, made basic with sodium bicarbonate, extracted three times with ethyl acetate, washed with common salt solution, dried on sodium sulfate and concentrated by evaporation. 557 mg of (2S)-2-(4-trifluoromethylphenylthio-methyl)-pyrrolidine is obtained.

We claim:

1. An estratriene intermediate compound of the formula:

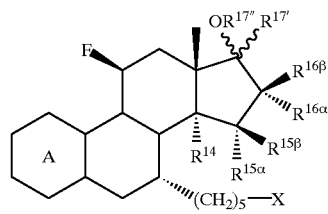

in which

X is halogen, —NHMe, OH or a protected hydroxy group, the A ring is

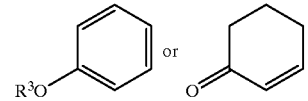

$R^3$ is a hydrogen atom or —$OR^3$ is a protected hydroxy group, $R^{14}$, $R^{15\alpha}$, $R^{15\beta}$, $R^{16\alpha}$ and $R^{16\beta}$ each are a hydrogen atom or $R^{14}$ and $R^{15\alpha}$ are an additional bond or a methylene bridge, or $R^{15\beta}$ is a methyl group and $R^{15\alpha}$ is a hydrogen atom, or $R^{15\alpha}$ and $R^{15\beta}$ in each case are a methyl group, or $R^{15\beta}$ and $R^{16\beta}$ together are a methylene bridge, or $R^{16\alpha}$ or $R^{16\beta}$ is a halogen atom or $R^{16\alpha}$ and $R^{16\beta}$ together are a methylidene group and the others of substituents $R^{14}$, $R^{15\alpha}$, $R^{15\beta}$, $R^{16\alpha}$ and $R^{16\beta}$ are each a hydrogen atom, $R^{17'}$ in α- or β-position is a hydrogen atom, $R^{17''}$ is a hydrogen atom or a radical of partial formula $R^{17'''}$—C(O)—, in which $R^{17'''}$ is a hydrogen atom or a hydrocarbon radical with up to 8 carbon atoms, or $R^{17'}$ and $OR^{17''}$ together are =O, as well as their physiologically compatible addition salts with organic and inorganic acids.

2. A compound according to claim 1, in which the A ring is

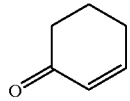

and $R^{17'}$ and $OR^{17''}$ together are =O.

3. A compound according to claim 1, in which X is OH or a protected hydroxy group.

4. A compound according to claim 2, in which X is OH or a protected hydroxy group.

5. A compound according to claim 1, wherein the protected hydroxy groups are ester or ether groups.

6. A compound according to claim 2, in which X is

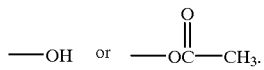

7. A compound according to claim 6, in which $R^{14}$, $R^{15\alpha}$, $R^{15\beta}$, $R^{16\alpha}$ and $R^{1616\beta}$ are all hydrogen.

8. A compound according to claim 1, in which $R^{17'}$ and $OR^{17''}$ together are =O, the A ring is

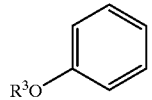

where $R^3$ is tetrahydropyranyl and X is a toluenesulfonyl protected hydroxy group.

9. A compound according to claim 1, in which $R^{17'}$ and $R^{17''}$ together are =O, the A ring is

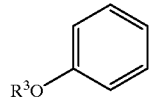

where $R^3$ is hydrogen and X is halogen.

10. A compound according to claim 1, in which $R^{17'}$ and $R^{17''}$ together are =O, the A ring is

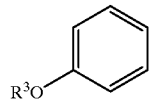

where $R^3$ is hydrogen and X is —NHMe.

11. A compound according to claim 1, which is:

11β-Fluoro-7α-(5-hydroxypentyl)-estr-4-ene-3,17-dione

7α-(5-Acetoxypentyl)-11β-fluoro-estr-4-ene-3,17-dione

7α-(5-Chloropentyl)-11β-fluoro-3-hydroxy-estra-1,3,5(10)-trien-17-one

11β-Fluoro-3-hydroxy-7α-(5-iodopentyl)-estra-1,3,5(10)-trien-17-one.

* * * * *